(12) United States Patent
Yamamoto et al.

(10) Patent No.: US 10,388,903 B2
(45) Date of Patent: *Aug. 20, 2019

(54) CHARGE-TRANSPORTING MATERIAL, ORGANIC ELECTROLUMINESCENT ELEMENT, AND LIGHT-EMITTING DEVICE, DISPLAY DEVICE AND ILLUMINATION DEVICE CHARACTERISED BY USING SAID ELEMENT

(71) Applicant: UDC Ireland Limited, Dublin (IE)

(72) Inventors: Yosuke Yamamoto, Kanagawa (JP); Kousuke Watanabe, Kanagawa (JP); Yuichiro Itai, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 1239 days.

This patent is subject to a terminal disclaimer.

(21) Appl. No.: 14/351,154

(22) PCT Filed: Nov. 14, 2012

(86) PCT No.: PCT/IB2012/002348
§ 371 (c)(1),
(2) Date: Jun. 23, 2014

(87) PCT Pub. No.: WO2013/072740
PCT Pub. Date: May 23, 2013

(65) Prior Publication Data
US 2014/0306205 A1    Oct. 16, 2014

(30) Foreign Application Priority Data

Nov. 15, 2011  (JP) .................................. 2011-250053

(51) Int. Cl.
| | | |
|---|---|---|
| *H01L 51/00* | (2006.01) | |
| *C09K 11/06* | (2006.01) | |
| *H01L 51/50* | (2006.01) | |
| *C07F 15/00* | (2006.01) | |
| *H05B 33/14* | (2006.01) | |

(52) U.S. Cl.
CPC ...... *H01L 51/5056* (2013.01); *C07F 15/0033* (2013.01); *C09K 11/06* (2013.01); *H01L 51/0085* (2013.01); *H01L 51/5016* (2013.01); *H01L 51/5072* (2013.01); *H01L 51/5088* (2013.01); *H01L 51/5092* (2013.01); *H05B 33/14* (2013.01); *C09K 2211/185* (2013.01); *H01L 51/0051* (2013.01); *H01L 51/0054* (2013.01); *H01L 51/0074* (2013.01); *H01L 51/0081* (2013.01)

(58) Field of Classification Search
None
See application file for complete search history.

(56) References Cited

U.S. PATENT DOCUMENTS

| | | | | |
|---|---|---|---|---|
| 2005/0244674 A1* | 11/2005 | Yasuda | .................. | C08G 61/10 428/690 |
| 2008/0210930 A1* | 9/2008 | Kamatani | ........... | C07F 15/0033 257/40 |
| 2010/0133992 A1* | 6/2010 | Yang | .................... | C07D 265/38 313/504 |

FOREIGN PATENT DOCUMENTS

| | | | | |
|---|---|---|---|---|
| CN | 101875674 | | 11/2010 | |
| JP | 2006298999 A | * | 11/2006 | |
| JP | WO 2012133042 A1 | * | 10/2012 | ........... C07C 255/50 |
| WO | 2010028151 | | 3/2010 | |
| WO | 2010111175 | | 9/2010 | |

OTHER PUBLICATIONS

International Preliminary Report on Patentability for International Patent Application No. PCT/IB2012/002348, dated May 20, 2014, 7 pages.
International Search Report for International Patent Application No. PCT/IB2012/002348, dated May 27, 2013, 2 pages.
Publication for International Patent Application No. PCT/IB2012/002348, dated May 23, 2013, 111 pages.
Written Opinion for International Patent Application No. PCT/IB2012/002348, dated May 27, 2013, 5 pages.

* cited by examiner

*Primary Examiner* — Emily A Bernhardt
*Assistant Examiner* — Laura M Daniel
(74) *Attorney, Agent, or Firm* — Riverside Law LLP

(57) ABSTRACT

An organic electroluminescent element having high durability can be provided by using a compound represented by the following general formula (1), wherein: $Z^1$ to $Z^4$ each represent a carbon atom or a nitrogen atom; $A^1$ represents an atomic group which is combined with $Z^1$ and a nitrogen atom to form a 5- or 6-membered hetero ring; $B^1$ represents an atomic group which is combined with $Z^2$ and a carbon atom to form a 5- or 6-membered ring; $C^1$ represents an atomic group which is combined with $Z^3$ and a nitrogen atom to form a 5- or 6-membered hetero ring; $D^1$ represents an atomic group which is combined with $Z^4$ and a carbon atom to form a 5- or 6-membered ring; n represents 1 or 2; L represents a single bond or a linking group; and G represents a fused ring with 3 or more rings.

General Formula (1)

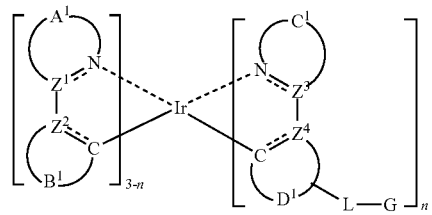

8 Claims, 2 Drawing Sheets

CHARGE-TRANSPORTING MATERIAL, ORGANIC ELECTROLUMINESCENT ELEMENT, AND LIGHT-EMITTING DEVICE, DISPLAY DEVICE AND ILLUMINATION DEVICE CHARACTERISED BY USING SAID ELEMENT

CROSS-REFERENCE TO RELATED APPLICATIONS

This application is a national stage entry of International Patent Application No. PCT/IB2012/002348, filed 14 Nov. 2012, which in turn claims priority to, and the benefit of, Japanese Patent Application No. 2011-250053, filed 15 Nov. 2011, all of which are incorporated herein by reference in their entireties.

TECHNICAL FIELD

The present invention relates to a charge transporting material, an organic electroluminescent element, and a light emitting device, a display device, and an illumination device each using the element.

BACKGROUND ART

Since organic electroluminescent elements (which may hereinafter also be referred to as "elements" or "organic EL elements") are capable of high-luminance light emitting with driving at a low voltage, they have been actively researched and developed. The organic electroluminescent elements have organic layers between a pair of electrodes, and utilize, for light emitting, energy of the exciton generated as a result of recombination of electrons injected from a cathode and holes injected from an anode in the organic layer.

Recently, by using a phosphorescent light emitting material such as an iridium complex and a platinum complex, an increase in the efficiency of elements have been developed. Further, doped elements using a light emitting layer doped in a host material, using a light emitting material as a guest material, have been widely adopted and used. Such an iridium complex, an iridium complex having a structure having divalent ligands, containing two 5- or 6-membered rings connected via a single bond, coordinated at a total of 3 sites on iridium atoms, in which carbon atoms or nitrogen atoms constituting each of the 5- or 6-membered rings are coordinated on iridium atoms, have been widely known. For example, PTL 1 describes that by using an iridium complex exhibiting green phosphorescent light emission, in which one or two of each of a ligand having a benzene ring substituted with a phenyl group and a pyridine ring connected via a single bond, and a ligand having a benzene ring and a pyridine ring connected via a single bond, an organic electroluminescent element having excellent luminous efficiency and durability is obtained. Further, PTL 2 describes that by using an iridium complex exhibiting phosphorescent light emission, in which one or two of each of a ligand having a benzene ring substituted with a phenyl group, a hetero ring group of a 5- or 6-membered ring, a bicyclic fused ring group or the like, and a pyridine ring connected via a single bond, and a ligand having a benzene ring and a pyridine ring connected via a single bond are used, an organic electroluminescent element having excellent color, luminous efficiency, and durability is obtained.

On the other hand, an iridium complex having a ligand, in which one of two 5- or 6-membered rings in the ligand is fused with another ring via a single bond, has been known. For example, PTL 3 describes that by using an iridium complex exhibiting phosphorescent light emission, in which one ligand having a fused ring containing three rings and a pyridine ring connected via a single bond, and two ligands having a benzene ring and a pyridine ring connected via a single bond are used, an organic electroluminescent element having excellent luminous efficiency and durability is obtained.

In addition, PTL 4 describes an iridium complex having ligands with various structures, and also describes that by using the iridium complex described in the same literature in an organic layer formed by a wet type film-forming method, an organic electroluminescent element having high durability and high efficiency can be provided.

CITATION LIST

Patent Literature

[PTL 1] WO2009/073245
[PTL 2] WO2010/028151
[PTL 3] WO2010/111175
[PTL 4] JP-A-2010-229121

SUMMARY OF INVENTION

Technical Problem

Under these circumstance, the present inventors have investigated the features of organic electroluminescent elements using the compounds described in PTLs 1 to 4, and as a result, it could be found that even though these literatures include a description of excellent durability, complaints from the viewpoint of practical use remain, and accordingly, there is a demand of additional improvement in durability. It could also be seen that with regard to driving voltage, an additional decrease in voltage is demanded from the viewpoint of practical use.

To solve the aforementioned problems, the present invention is to provide a compound capable of providing an organic electroluminescent element having excellent durability and driving voltage.

Solution to Problem

The present inventors have conducted extensive investigations, and as a result, they have found that an iridium complex having a structure having divalent ligands, containing two 5- or 6-membered rings connected via a single bond, coordinated at a total of 3 sites on iridium atoms, in which carbon atoms or nitrogen atoms constituting each of the 5- or 6-membered rings are coordinated on iridium atoms, can remarkably increase the durability of an organic electroluminescent element and lower the driving voltage, when used for the element, by 1 or 2 ligands having 3 or more fused rings as an additional substituent in the 5- or 6-membered ring.

That is, the present invention can be attained by the following means.

[1] A compound represented by the following general formula (1).

[Chem. 1]

General Formula (1)

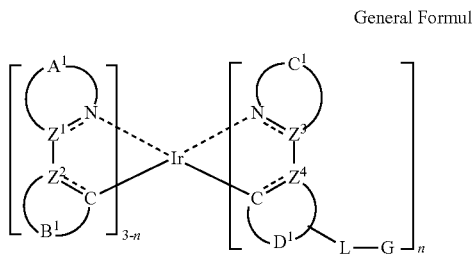

(In the general formula (1), $Z^1$ to $Z^4$ each independently represent a carbon atom or a nitrogen atom. $A^1$ represents an atomic group which is combined with $Z^1$ and a nitrogen atom to form a 5- or 6-membered hetero ring, $B^1$ represents an atomic group which is combined with $Z^2$ and a carbon atom to form a 5- or 6-membered ring, $C^1$ represents an atomic group which is combined with $Z^3$ and a nitrogen atom to form a 5- or 6-membered hetero ring, and $D^1$ represents an atomic group which is combined with $Z^4$ and a carbon atom to form a 5- or 6-membered ring. n represents 1 or 2. L represents a single bond or a linking group. G represents a fused ring with 3 or more rings. However, the ring formed of $A^1$ to $C^1$ does not include a fused ring with 3 or more rings.)

[2] In the compound as described in [1], the compound represented by the general formula (1) is preferably a compound represented by the following general formula (2).

[Chem. 2]

General Formula (2)

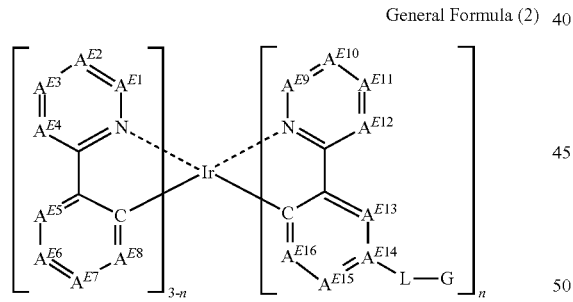

(In the general formula (2), $A^{E1}$ to $A^{E13}$, $A^{E15}$, and $A^{E16}$ each independently represent a nitrogen atom or C—$R^E$. A plurality of $R^E$s each independently represent a hydrogen atom or a substituent. $A^{E14}$ represents a carbon atom. n represents 1 or 2. L represents a single bond or a linking group. G represents a fused ring with 3 or more rings. However, $R^E$ does not include a fused ring with 3 or more rings.)

[3] In the compound as described in [1] or [2], the compound represented by the general formula (1) is preferably a compound represented by the following general formula (3).

[Chem. 3]

General Formula (3)

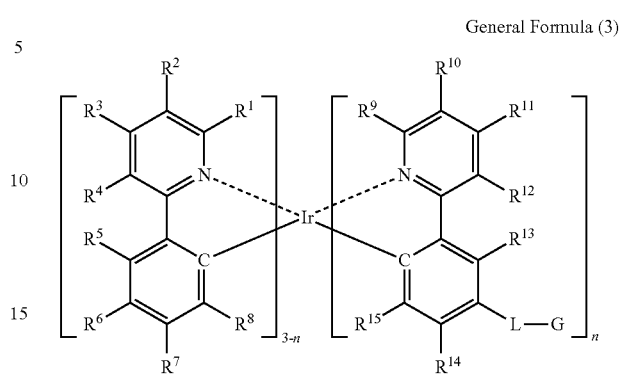

(In the general formula (3), $R^1$ to $R^{15}$ each independently represent a hydrogen atom, an alkyl group, an aryl group, or a heteroaryl group. n represents 1 or 2. L represents a single bond or a linking group. G represents a fused ring with 3 or more rings. However, $R^1$ to $R^{15}$ does not include a fused ring with 3 or more rings.)

[4] In the compound as described in any one of [1] to [3], L of the compound represented by the general formula (1) is preferably a single bond or a group selected from the following group $L^1$ of linking groups.

[Chem. 4]

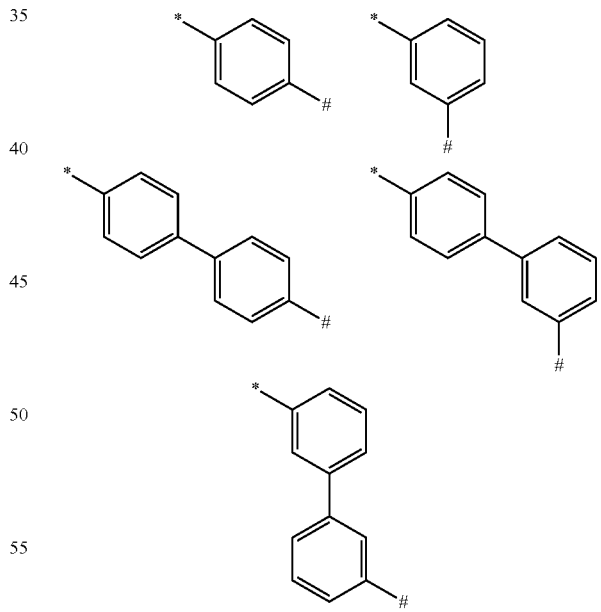

(In the formula, * represents a binding position with a 5- or 6-membered ring formed of $D^1$, $Z^4$, and a carbon atom, and # represents a binding position with G.)

[5] In the compound as described in any one of [1] to [4], G of the compound represented by the general formula (1) is preferably represented by the following general formula $G^A$.

[Chem. 5]

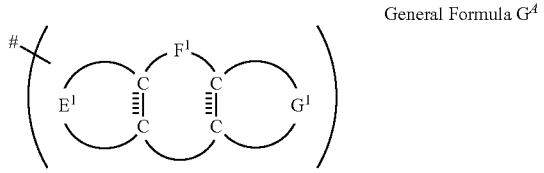

General Formula $G^A$ (In the formula, $E^1$ to $G^1$ rings each represent an atomic group which is combined with a carbon atom to form a 5- to 7-membered ring. # represents a binding position with L.)

[6] In the compound as described in any one of [1] to [5], G of the compound represented by the general formula (1) is preferably selected from the following Substituent Group $G^B$.

Substituent Group $G^B$

[Chem. 6]

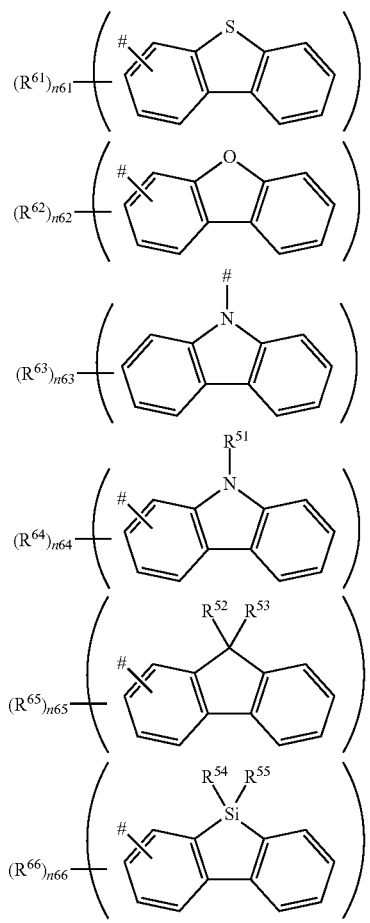

(In the formula, $R^{51}$ to $R^{55}$ each independently represent an alkyl group or an aryl group, and # represents a binding position with L. $R^{61}$ to $R^{66}$ each independently represent a hydrogen atom or a substituent, and n61 to n66 each independently represent an integer of 0 to 8.)

[7] An organic electroluminescent element including a substrate, a pair of electrodes including an anode and a cathode, disposed on the substrate, and at least one organic layer including a light emitting layer, disposed between the electrodes, in which the at least one organic layer contains a compound represented by the following general formula (1).

[Chem. 7]

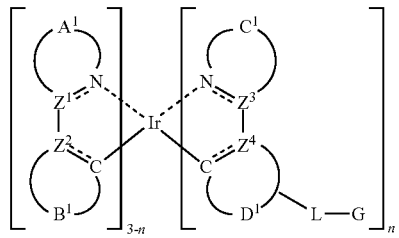

General Formula (1)

(In the general formula (1), $Z^1$ to $Z^4$ each independently represent a carbon atom or a nitrogen atom. $A^1$ represents an atomic group which is combined with $Z^1$ and a nitrogen atom to form a 5- or 6-membered hetero ring, $B^1$ represents an atomic group which is combined with $Z^2$ and a carbon atom to form a 5- or 6-membered ring, $C^1$ represents an atomic group which is combined with $Z^3$ and a nitrogen atom to form a 5- or 6-membered hetero ring, and $D^1$ represents an atomic group which is combined with $Z^4$ and a carbon atom to form a 5- or 6-membered ring. n represents 1 or 2. L represents a single bond or a linking group. G represents a fused ring with 3 or more rings. However, the ring formed of $A^1$ to $C^1$ does not include a fused ring with 3 or more rings.)

[8] In the organic electroluminescent element as described in [7], the compound represented by the general formula (1) is preferably a compound represented by the following general formula (2).

[Chem. 8]

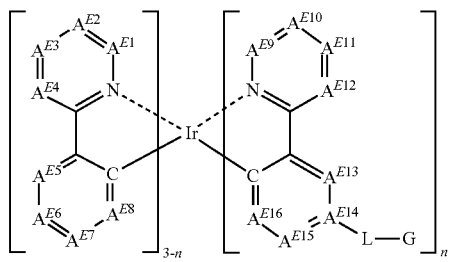

General Formula (2)

(In the general formula (2), $A^{E1}$ to $A^{E13}$, $A^{E15}$, and $A^{E16}$ each independently represent a nitrogen atom or C—$R^E$. A plurality of $R^E$s each independently represent a hydrogen atom or a substituent. $A^{E14}$ represents a carbon atom. n represents 1 or 2. L represents a single bond or a linking group. G represents a fused ring with 3 or more rings. However, $R^E$ does not include a fused ring with 3 or more rings.)

[9] In the organic electroluminescent element as described in [7] or [8], the compound represented by the general formula (1) is preferably a compound represented by the following general formula (3).

[Chem. 9]

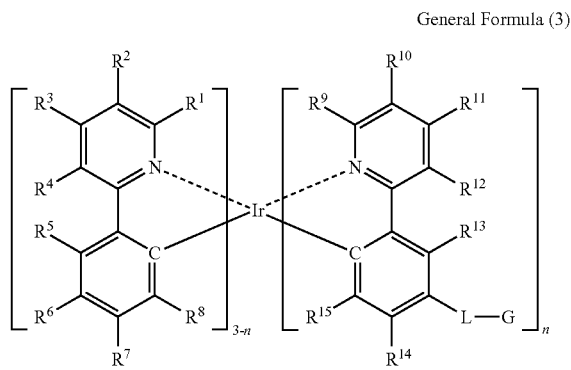

General Formula (3)

(In the general formula (3), $R^1$ to $R^{15}$ each independently represent a hydrogen atom, an alkyl group, an aryl group, or a heteroaryl group. n represents 1 or 2. L represents a single bond or a linking group. G represents a fused ring with 3 or more rings. However, $R^1$ to $R^{15}$ does not include a fused ring with 3 or more rings.)

[10] In the organic electroluminescent element as described in any one of [7] to [9], L of the compound represented by the general formula (1) is preferably a single bond or a group selected from the following group $L^1$ of linking groups.

Group $L^1$ of Linking Groups

[Chem. 10]

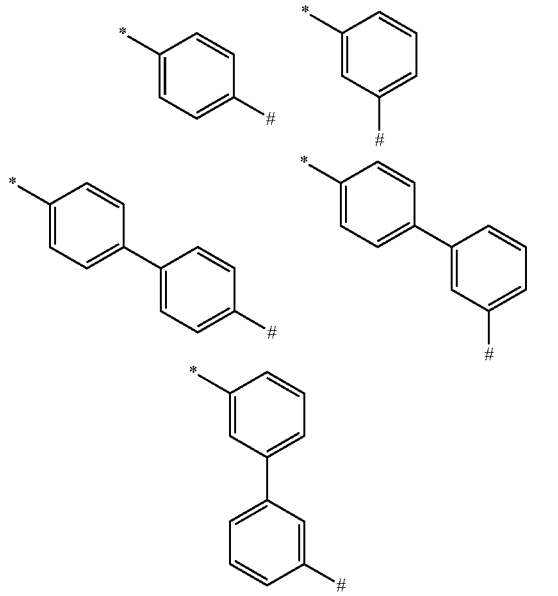

(In the formula, * represents a binding position with a 5- or 6-membered ring formed of $D^1$, $Z^4$, and a carbon atom, and # represents a binding position with G.)

[11] In the organic electroluminescent element as described in any one of [7] to [10], G of the compound represented by the general formula (1) is preferably represented by the following general formula $G^4$.

[Chem. 11]

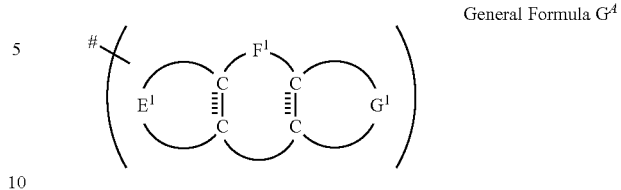

General Formula $G^4$ (In the formula, $E^1$ to $G^1$ rings each represent an atomic group which is combined with a carbon atom to form a 5- to 7-membered ring. # represents a binding position with L.)

[12] In the organic electroluminescent element as described in any one of [7] to [11], G of the compound represented by the general formula (1) is preferably selected from the following Substituent Group $G^B$.

[Chem. 12]

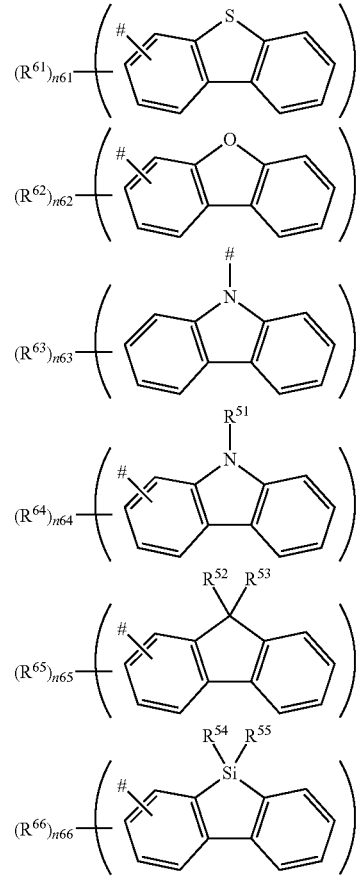

(In the formula, $R^{51}$ to $R^{55}$ each independently represent an alkyl group or an aryl group, and # represents a binding position with L. $R^{61}$ to $R^{66}$ each independently represent a hydrogen atom or a substituent, and n61 to n66 each independently represent an integer of 0 to 8.)

[13] In the organic electroluminescent element as described in any one of [7] to [12], the compound represented by the general formula (1) is preferably contained in the light emitting layer in the organic layer(s).

[14] A light emitting device using the organic electroluminescent element as described in any one of [7] to [13].

[15] A display device using the organic electroluminescent element as described in any one of [7] to [13].

[16] An illumination device using the organic electroluminescent element as described in any one of [7] to [13].

Advantageous Effects of Invention

By using the compound of the present invention, an organic electroluminescent element having high durability and excellent element driving voltage can be provided.

DESCRIPTION OF EMBODIMENTS

Figure 1:
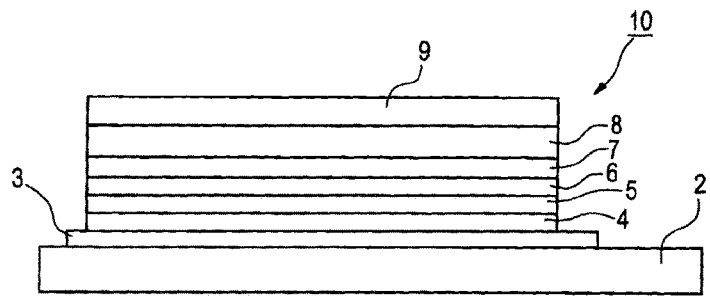
FIG. 1 is a schematic view showing one example of a configuration of an organic electroluminescent element according to the present invention.

Hereinafter, the disclosure of the present invention will be described in detail. The description of the requirements of the configuration as described below is based on representative embodiments of the present invention in some cases, but the present invention is not limited to these embodiments. Incidentally, in the present specification, the numerical range expressed with "to" means a range including the numerical values before and after "to" as the lower limit and the upper limit, respectively.

[Compounds]

The compound of the present invention is represented by the following general formula (1).

[Chem. 13]

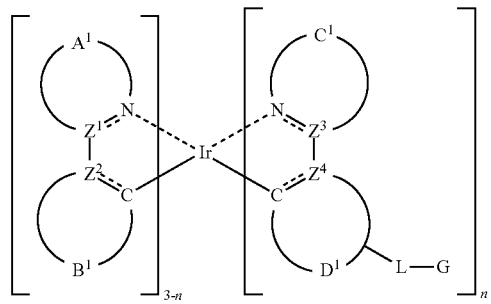

General Formula (1)

(In the general formula (1), $Z^1$ to $Z^4$ each independently represent a carbon atom or a nitrogen atom. $A^1$ represents an atomic group which is combined with $Z^1$ and a nitrogen atom to form a 5- or 6-membered hetero ring, $B^1$ represents an atomic group which is combined with $Z^2$ and a carbon atom to form a 5- or 6-membered ring, $C^1$ represents an atomic group which is combined with $Z^3$ and a nitrogen atom to form a 5- or 6-membered hetero ring, and $D^1$ represents an atomic group which is combined with $Z^4$ and a carbon atom to form a 5- or 6-membered ring. n represents 1 or 2. L represents a single bond or a linking group. G represents a fused ring with 3 or more rings. However, the ring formed of $A^1$ to $C^1$ does not include a fused ring with 3 or more rings.)

Not wishing to be restricted to any theory, when the compound of the present invention has such a structure, the use of an extended π conjugation system having 3 or more fused rings makes it possible to improve the charge transporting property (hole and electron transporting properties) or improve the stability for charges (holes and electrons) by stabilization of a radical cation state and a radical anion state, and thus to improve the durability and driving voltage for use in an organic electroluminescent element.

Hereinafter, the preferred range of the compound represented by the general formula (1) will be described.

Furthermore, in the present invention, the hydrogen atom in the description of the general formula (1) also includes isotopes (a deuterium atom and the like), and the atoms additionally constituting the substituent are also intended to include isotopes of the atoms.

In the present invention, the "substituent" at each occurrence may be further substituted with a substituent. For example, the "alkyl group" in the present invention includes an alkyl group substituted with a fluorine atom (for example, a trifluoromethyl group) and an alkyl group substituted with an aryl group (for example, a triphenylmethyl group).

In the general formula (1), $Z^1$ to $Z^4$ each independently represent a carbon atom or a nitrogen atom, and preferably a carbon atom.

In the general formula (1), $A^1$ represents an atomic group which is combined with $Z^1$ and a nitrogen atom to form a 5- or 6-membered hetero ring, and examples of the 5- or 6-membered hetero ring containing $A^1$, $Z^1$, and a nitrogen atom (hereinafter also referred to as a ring formed with $A^1$) include a pyridine ring, a pyrimidine ring, a pyrazine ring, a triazine ring, an imidazole ring, a pyrazole ring, an oxazole ring, a triazole ring, a triazole ring, an oxadiazole ring, and a thiadiazole ring. The ring formed of $A^1$ may be an aromatic hetero ring or a non-aromatic hetero ring, but it is preferably an aromatic hetero ring. Examples of the hetero atom contained in ring formed of $A^1$ include a sulfur atom, a nitrogen atom, an oxygen atom, and a silicon atom, and a ring formed of $A^1$ more preferably contains only a nitrogen atom.

From the viewpoint of stability of a complex, control of light emitting wavelength, and light emitting quantum yield, the 5- or 6-membered hetero ring formed of $A^1$, $Z^1$, and a nitrogen atom is preferably a pyridine ring, a pyrazine ring, an imidazole ring, or a pyrazole ring, more preferably a pyridine ring, an imidazole ring, or a pyrazine ring, particularly preferably a pyridine ring or an imidazole ring, and more particularly preferably a pyridine ring.

The 5- or 6-membered hetero ring formed of $A^1$, $Z^1$, and a nitrogen atom may have a substituent, and as the substituent on a carbon atom and the substituent on a nitrogen atom, the following Substituent Group A and the following Substituent Group B can be applied, respectively. However, the ring formed of $A^1$ does not include a fused ring with 3 or more rings. In addition, in the case where the nitrogen atom constitutes an aromatic hetero ring, the nitrogen atom has no substituent.

<<Substituent Group A>>

An alkyl group (preferably having 1 to 30 carbon atoms, more preferably having 1 to 20 carbon atoms, and particularly preferably having 1 to 10 carbon atoms; for example, methyl, ethyl, n-propyl, isopropyl, t-butyl, n-hexyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 10 carbon atoms, and more preferably having 6 carbon atoms; for example, phenyl, p-methylphenyl, and naphthyl), an amino group (preferably having 0 to 30 carbon atoms, more preferably 0 to 20 carbon atoms, and particularly preferably 0 to 10 carbon atoms; for example, amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms; for example, methoxy, ethoxy, butoxy, and 2-ethylhexyloxy), an aryloxy group (preferably having 6 to 10 carbon atoms, and more preferably having 6 carbon atoms; for example, phenyloxy, 1-naphthyloxy, and 2-naphthyloxy), a hetero ring oxy group (preferably having 1 to 10 carbon atoms, more preferably having 1 to 6 carbon atoms, and particularly preferably having 5 or 6 carbon atoms; for example, pyridyloxy, pyrazyloxy, pyrimidyloxy, and quinolyloxy), an acyl group (preferably having 2 to 30 carbon atoms, more preferably having 2 to 20 carbon atoms, and particularly preferably having 2 to 12 carbon atoms; for example, acetyl, benzoyl, formyl, and pivaloyl), an alkoxycarbonyl group (preferably having 2 to 30 carbon atoms, more preferably having 2 to 20 carbon atoms, and particularly preferably having 2 to 12 carbon atoms; for example, methoxycarbonyl and ethoxycarbonyl), an aryloxycarbonyl group (preferably having 7 to 11 carbon atoms, and more preferably having 7 carbon atoms; for example, phenyloxycarbonyl), an acyloxy group (preferably having 2 to 30 carbon atoms, more preferably having 2 to 20 carbon atoms, and particularly preferably having 2 to 10 carbon atoms; for example, acetoxy and benzoyloxy), an acylamino group (preferably having 2 to 30 carbon atoms, more preferably having 2 to 20 carbon atoms, and particularly preferably having 2 to 10 carbon atoms; for example, acetylamino and benzoylamino), an alkoxycarbonylamino group (preferably having 2 to 30 carbon atoms, more preferably having 2 to 20 carbon atoms, and particularly preferably having 2 to 12 carbon atoms; for example, methoxycarbonylamino), an aryloxycarbonylamino group (preferably having 7 to 11 carbon atoms, and more preferably having 7 carbon atoms; for example, phenyloxycarbonylamino), a sulfonylamino group (preferably having 1 to 30 carbon atoms, more preferably having 1 to 20 carbon atoms, and particularly preferably having 1 to 12 carbon atoms; for example, methanesulfonylamino and benzenesulfonylamino), a sulfamoyl group (preferably having 0 to 30 carbon atoms, more preferably having 0 to 20 carbon atoms, and particularly preferably having 0 to 12 carbon atoms; for example, sulfamoyl, methylsulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms; for example, carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms; for example, methylthio and ethylthio), an arylthio group (preferably having 6 to 10 carbon atoms, and more preferably having 6 carbon atoms; for example, phenylthio), a hetero ring thio group (preferably having 1 to 10 carbon atoms, more preferably having 1 to 6 carbon atoms, and particularly preferably having 5 or 6 carbon atoms; for example, pyridylthio, 2-benzoimizolylthio, 2-benzoxazolylthio, and 2-benzothiazolylthio), a sulfonyl group (preferably having 1 to 30 carbon atoms, more preferably having 1 to 20 carbon atoms, and particularly preferably having 1 to 12 carbon atoms; for example, mesyl and tosyl), a sulfinyl group (preferably having 1 to 30 carbon atoms, more preferably having 1 to 20 carbon atoms, and particularly preferably having 5 or 6 carbon atoms; for example, methanesulfinyl and benzenesulfinyl), a ureido group (preferably having 1 to 30 carbon atoms, more preferably having 1 to 20 carbon atoms, and particularly preferably having 1 to 12 carbon atoms; for example, ureido, methylureido, and phenylureido), a phosphoramide group (preferably having 1 to 30 carbon atoms, more preferably having 1 to 20 carbon atoms, and particularly preferably having 1 to 12 carbon atoms; for example, diethyl phosphoramide and phenyl phosphoramide), a hydroxyl group, a mercapto group, a halogen atom (for example, a fluorine atom, a chlorine atom, a bromine atom, and an iodine atom), a cyano group, a sulfo group, a carboxyl group, a nitro group, a hydroxamic group, a sulfino group, a hydrazino group, an imino group, a hetero ring group (inclusive of an aromatic hetero ring group, which preferably has 1 to 10 carbon atoms, and more preferably 5 or 6 carbon atoms; and examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, and benzothiazolyl), a silyl group (preferably having 3 to 40 carbon atoms, more preferably 3 to 30 carbon atoms, and particularly preferably 3 to 24 carbon atoms; for example, trimethylsilyl and triphenylsilyl), a silyloxy group (preferably having 3 to 40 carbon atoms, more preferably having 3 to 30 carbon atoms, and particularly preferably having 3 to 24 carbon atoms; for example, trimethylsilyloxy and triphenylsilyloxy), and a phosphoryl group (for example, a diphenylphosphoryl group and a dimethylphosphoryl group). These substituents may be further substituted, and examples of the additional substituent include the groups selected from the Substituent Group A as described above. Further, the substituent substituted with a substituent may be further substituted, and examples of the additional substituent include the groups selected from the Substituent Group A as described above. In addition, the substituent substituted with the substituent which has been substituted with a substituent may be further substituted, and examples of the additional substituent include the groups selected from the Substituent Group A as described above.

<<Substituent Group B>>

An alkyl group (preferably having 1 to 30 carbon atoms, more preferably having 1 to 20 carbon atoms, and particularly preferably having 1 to 10 carbon atoms; for example, methyl, ethyl, n-propyl, isopropyl, t-butyl, n-hexyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 10 carbon atoms, and more preferably having 6 carbon atoms; for example, phenyl, p-methylphenyl, and naphthyl), a cyano group, and a hetero ring group (inclusive of an aromatic hetero ring group, which preferably has 1 to 10 carbon atoms, and more preferably 5 or 6 carbon atoms; and examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, and benzothiazolyl). These substituents may be further substituted, and examples of the additional substituent include the groups selected from the Substituent Group B. Further, the substituent substituted with a substituent may be further substituted, and examples of the additional substituent include the groups selected from the Substituent Group B as described above. In addition, the substituent substituted with the substituent which has been substituted with a substituent may be further substituted, and examples of the additional substituent include the groups selected from the Substituent Group B as described above.

The substituent on carbon contained in the ring formed of $A^1$ is preferably an alkyl group, a perfluoroalkyl group, an aryl group, an aromatic hetero ring group (heteroaryl group), a dialkylamino group, a diarylamino group, an alkoxy group, a cyano group, or a fluorine atom in the Substituent Group A.

The substituent on nitrogen contained in the ring formed of $A^1$ is preferably an alkyl group, an aryl group, or an aromatic hetero ring group in the Substituent Group B, and from the viewpoint of the stability of a complex, it is preferably an alkyl group or an aryl group.

The substituent contained in the ring formed of $A^1$ is appropriately selected to control light emitting wavelength and potentials, but in the case of decreasing the wavelength, an electron donating group, a fluorine atom, and an aromatic ring group are preferred, and for example, an alkyl group, a dialkylamino group, an alkoxy group, a fluorine atom, an aryl group, an aromatic hetero ring group, and the like are selected. Further, in the case of increasing the wavelength, an electron withdrawing group is preferred, and for example, a cyano group, a perfluoroalkyl group, and the like are selected.

The substituents contained in the rings formed of $A^1$ may be connected with each other to form a fused ring, and examples of the ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring. However, the ring formed of $A^1$ does not include a fused ring with 3 or more rings. These rings thus formed may have a substituent and examples of the substituent include the substituents on carbon atoms or the substituents on nitrogen atoms as described above.

In the present invention, for the compound represented by the general formula (1), the ring formed of $A^1$ preferably has 0 to 4 substituents, more preferably has 0 to 2 substituents, particularly preferably has zero or one substituent, and more particularly preferably has one substituent.

In the present invention, for the compound represented by the general formula (1), preferably, the ring formed of $A^1$ is unsubstituted or has an alkyl group, an aryl group, or a heteroaryl group. Preferably, the ring is unsubstituted or has an alkyl group, a phenyl group, or a heteroaryl group in the range of the Substituent Group A and Substituent Group B as described above; more preferably, the ring is unsubstituted or has an alkyl group having 1 to 6 carbon atoms, or a phenyl group; particularly preferably, the ring is unsubstituted or has a methyl group, an ethyl group, an isopropyl group, or a 2-methyl-propyl group; more particularly preferably, the ring is unsubstituted or has a methyl group; and still more particularly preferably a methyl group.

In the general formula (1), $B^1$ represents an atomic group which is combined with $Z^2$ and a carbon atom to form a 5- or 6-membered ring, and examples of the 5- or 6-membered ring formed of $B^1$, $Z^2$, and a carbon atom (hereinafter also referred to as a ring formed of $B^1$) include a benzene ring, a pyridine ring, a pyrimidine ring, a pyrazine ring, a pyridazine ring, a triazine ring, an imidazole ring, a pyrazole ring, an oxazole ring, a triazole ring, a triazole ring, an oxadiazole ring, a thiadiazole ring, a thiophene ring, and a furan ring. The ring formed of $B^1$ may be any one of an aromatic hydrocarbon ring, an aromatic hetero ring, an aliphatic hydrocarbon ring, and a non-aromatic hetero ring; and preferably an aromatic hydrocarbon ring. Further, examples of the hetero atom contained in the ring formed of $B^1$ include a sulfur atom, a nitrogen atom, an oxygen atom, and a silicon atom.

From the viewpoint of the stability of a complex, the control of light emitting wavelength, and the light emitting quantum yield, the 5- or 6-membered ring formed of $B^1$, $Z^2$, and a carbon atom is preferably a benzene ring, a pyridine ring, a pyrazine ring, an imidazole ring, a pyrazole ring, or a thiophene ring, more preferably a benzene ring, a pyridine ring, or a pyrazole ring, particularly preferably a benzene ring or a pyridine ring, and more particularly preferably a benzene ring.

The 5- or 6-membered ring formed of $B^1$, $Z^2$, and a carbon atom may have a substituent, and as the substituent on a carbon atom and the substituent on a nitrogen atom, the Substituent Group A and the Substituent Group B can be applied, respectively. However, the ring formed of $B^1$ does not include a fused ring with 3 or more rings. In addition, in the case where the nitrogen atom constitutes an aromatic hetero ring, the nitrogen atom has no substituent.

The substituent on carbon contained in the ring formed of $B^1$ is preferably an alkyl group, a perfluoroalkyl group, an aryl group, an aromatic hetero ring group (heteroaryl group), a dialkylamino group, a diarylamino group, an alkoxy group, a cyano group, or a fluorine atom.

The substituent on nitrogen contained in the ring formed of $B^1$ is preferably an alkyl group, an aryl group, or an aromatic hetero ring group, and from the viewpoint of the stability of a complex, it is preferably an alkyl group or an aryl group.

The substituent contained in the ring formed of $B^1$ is appropriately selected to control light emitting wavelength and potentials, but in the case of increasing the wavelength, an electron donating group and an aromatic ring group are preferred, and for example, an alkyl group, a dialkylamino group, an alkoxy group, an aryl group, an aromatic hetero ring group, and the like are selected. Further, in the case of decreasing the wavelength, an electron withdrawing group is preferred, and for example, a fluorine atom, a cyano group, a perfluoroalkyl group, and the like are selected.

The substituents contained in the rings formed of $B^1$ may be connected with each other to form a ring, and examples of the ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring. However, the ring formed of $B^1$ does not include a fused ring with 3 or more rings. These rings thus formed may have a substituent and examples of the substituent include the substituents on carbon atoms or the substituents on nitrogen atoms as described above.

In the present invention, for the compound represented by the general formula (1), it is preferable that the substituents contained in the rings formed of $B^1$ be not connected with each other to form a ring.

Moreover, the substituent of the 5- or 6-membered hetero ring formed of $A^1$, $Z^1$, and a nitrogen atom and the substituent of the 5- or 6-membered hetero ring formed of $B^1$, $Z^2$, and a carbon atom may be connected with each other to form the same fused ring as above, but in the present invention, it is preferable that the compound represented by the general formula (1) do not form such a fused ring.

In the present invention, for the compound represented by the general formula (1), the ring formed of $B^1$ preferably has 0 to 4 substituents, more preferably has 0 to 2 substituents, particularly preferably has zero or one substituent, and more particularly preferably has zero substituents.

In the present invention, for the compound represented by the general formula (1), preferably, the ring formed of $B^1$ is unsubstituted or has an alkyl group, an aryl group, or a heteroaryl group. Preferably, the ring is unsubstituted or has an alkyl group, a phenyl group, or a heteroaryl group in the range of the Substituent Group A and Substituent Group B as described above; more preferably, the ring is unsubstituted or has an alkyl group having 1 to 6 carbon atoms, or a phenyl group; more particularly preferably, the ring is unsubstituted or has a methyl group; and still more particularly preferably, the ring is unsubstituted.

In the general formula (1), $C^1$ represents an atomic group which is combined with $Z^3$ and a nitrogen atom to form a 5- or 6-membered hetero ring, and examples of the 5- or 6-membered hetero ring formed of $C^1$, $Z^3$, and a nitrogen atom (hereinafter also referred to as a ring formed of $C^1$) include hetero rings such as the same rings formed of $A^1$ above. The ring formed of $C^1$ may be either an aromatic hetero ring or a non-aromatic hetero ring; and preferably an aromatic hetero ring. Further, examples of the hetero atom contained in the ring formed of $C^1$ include a sulfur atom, a nitrogen atom, an oxygen atom, and a silicon atom, with only a nitrogen atom being preferably contained.

From the viewpoint of the stability of a complex, the control of light emitting wavelength, and the light emitting quantum yield, the 5- or 6-membered hetero ring formed of $C^1$, $Z^3$, and a nitrogen atom is preferably a pyridine ring, a pyrazine ring, an imidazole ring, or a pyrazole ring, more preferably a pyridine ring, an imidazole ring, or a pyrazine ring, particularly preferably a pyridine ring or an imidazole ring, and more particularly preferably a pyridine ring.

The 5- or 6-membered hetero ring formed of $C^1$, $Z^3$, and a nitrogen atom may have a substituent, and as the substituent on a carbon atom and the substituent on a nitrogen atom, the Substituent Group A and the Substituent Group B can be applied, respectively. However, the ring formed of $C^1$ does not include a fused ring with 3 or more rings. In addition, in the case where the nitrogen atom constitutes an aromatic hetero ring, the nitrogen atom has no substituent.

The substituent on carbon contained in the ring formed of $C^1$ is preferably an alkyl group, a perfluoroalkyl group, an aryl group, an aromatic hetero ring group (heteroaryl group), a dialkylamino group, a diarylamino group, an alkoxy group, a cyano group, or a fluorine atom in the Substituent Group A.

The substituent on nitrogen contained in the ring formed of $C^1$ is preferably an alkyl group, an aryl group, or an aromatic hetero ring group in the Substituent Group B, and from the viewpoint of the stability of a complex, it is preferably an alkyl group or an aryl group.

The substituent contained in the ring formed of $C^1$ is appropriately selected to control light emitting wavelength and potentials, but in the case of decreasing the wavelength, an electron donating group, a fluorine atom, and aromatic ring group are preferred, and for example, an alkyl group, a dialkylamino group, an alkoxy group, a fluorine atom, an aryl group, an aromatic hetero ring group, and the like are selected. Further, in the case of increasing the wavelength, an electron withdrawing group is preferred, and for example, a fluorine atom, a cyano group, a perfluoroalkyl group, and the like are selected.

The substituents contained in the rings formed of $C^1$ may be connected with each other to form a fused ring, and examples of the ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring. However, the ring formed of $C^1$ does not include a fused ring with 3 or more rings. These rings thus formed may have a substituent and examples of the substituent include the substituents on carbon atoms or the substituents on nitrogen atoms as described above.

In the present invention, for the compound represented by the general formula (1), the ring formed of $C^1$ preferably has 0 to 4 substituents, more preferably has 0 to 2 substituents, particularly preferably has zero or one substituent, and more particularly preferably has zero substituents.

In the present invention, for the compound represented by the general formula (1), preferably, the ring formed of $C^1$ is unsubstituted or has an alkyl group, an aryl group, or a heteroaryl group. Preferably, the ring is unsubstituted or has an alkyl group, a phenyl group, or a heteroaryl group in the range of the Substituent Group A and Substituent Group B as described above; more preferably, the ring is unsubstituted or has an alkyl group having 1 to 6 carbon atoms, or a phenyl group; particularly preferably, the ring is unsubstituted or has a methyl group or an ethyl group; more particularly preferably, the ring is unsubstituted or has a methyl group; and still more particularly preferably, the ring is unsubstituted.

In the general formula (1), $D^1$ represents an atomic group which is combined with $Z^4$ and a carbon atom to form a 5- or 6-membered ring, and examples of the 5- or 6-membered ring formed of $D^1$, $Z^4$, and a carbon atom (hereinafter also referred to as a ring formed of $D^1$) include a benzene ring, a pyridine ring, a pyrimidine ring, a pyrazine ring, a pyridazine ring, a triazine ring, an imidazole ring, a pyrazole ring, an oxazole ring, a triazole ring, a triazole ring, an oxadiazole ring, a thiadiazole ring, a thiophene ring, a furan ring. The ring formed of $D^1$ may be any one of an aromatic hydrocarbon ring, an aromatic hetero ring, an aliphatic hydrocarbon ring, and a non-aromatic hetero ring; and preferably an aromatic hydrocarbon ring. Further, examples of the hetero atom contained in the ring formed of $D^1$ include a sulfur atom, a nitrogen atom, an oxygen atom, and a silicon atom.

From the viewpoint of the stability of a complex, the control of light emitting wavelength, and the light emitting quantum yield, the 5- or 6-membered ring formed of $D^1$, $Z^4$, and a carbon atom is preferably a benzene ring, a pyridine ring, a pyrazine ring, an imidazole ring, a pyrazole ring, or a thiophene ring, more preferably a benzene ring, a pyridine ring, or a pyrazole ring, particularly preferably a benzene ring or a pyridine ring, and more particularly preferably a benzene ring.

The 5- or 6-membered ring formed of $D^1$, $Z^4$, and a carbon atom may further have a substituent represented by -L-G, and may have a substituent other than the substituent represented by -L-G. As the substituent on a carbon atom and the substituent on a nitrogen atom of the 5- or 6-membered ring formed of $D^1$, $Z^4$, and a carbon atom, the substituent represented by -L-G or the Substituent Group A, and the substituent represented by -L-G or the Substituent Group B can be applied, respectively. In addition, in the case where the nitrogen atom constitutes an aromatic hetero ring, the nitrogen atom has no substituent.

The substituent on carbon contained in the ring formed of $D^1$ is preferably a substituent represented by -L-G, or the substituent other than the substituent represented by -L-G is preferably an alkyl group, a perfluoroalkyl group, an aryl group, an aromatic hetero ring group, a dialkylamino group, a diarylamino group, an alkoxy group, a cyano group, or a fluorine atom.

The substituent on nitrogen contained in the ring formed of $D^1$ is preferably a substituent represented by -L-G, and the substituent other than the substituent represented by -L-G is preferably an alkyl group, an aryl group, or an aromatic hetero ring group, and from the viewpoint of the stability of a complex, it is preferably an alkyl group or an aryl group.

The substituent contained in the ring formed of $D^1$ is appropriately selected to control light emitting wavelength and potentials, but in the case of increasing the wavelength, an electron donating group and an aromatic ring group are preferred, and in addition to the substituent represented by -L-G, for example, an alkyl group, a dialkylamino group, an alkoxy group, an aryl group, an aromatic hetero ring group, and the like are selected. Further, in the case of increasing the wavelength, an electron withdrawing group is preferred, and for example, a cyano group, a perfluoroalkyl group, and the like are selected.

The substituents contained in the rings formed of $D^1$ may be connected with each other to form a fused ring, and examples of the ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring. These rings thus formed may have a substituent and examples of the substituent include the substituents on carbon atoms or the substituents on nitrogen atoms as described above. However, there is no case where the substituent represented by -L-G, contained in the ring formed of $D^1$, is connected with another substituent contained in the ring formed of $D^1$ to form a fused ring.

In the present invention, for the compound represented by the general formula (1), it is preferable that the substituents contained in the rings formed of $D^1$ be not connected with each other to form a fused ring.

Moreover, the substituent of the 5- or 6-membered hetero ring formed of $C^1$, $Z^3$ and a nitrogen atom, and the substituent of the 5- or 6-membered ring formed of $D^1$, $Z^4$ and a carbon atom may be connected with each other to form the same fused ring as above, but in the present invention, it is preferable that the compound represented by the general formula (1) do not form such a fused ring.

In the present invention, for the compound represented by the general formula (1), the ring formed of $D^1$ preferably has 0 to 2 substituents other than the substituent represented by -L-G, particularly preferably has zero or one substituent other than the substituent represented by -L-G, and more particularly preferably has zero substituents other than the substituent represented by -L-G.

In the present invention, for the compound represented by the general formula (1), preferably, the ring formed of $D^1$ preferably has an alkyl group as a substituent other than the substituent represented by -L-G, in addition to the substituent represented by -L-G. In the case where the ring formed of $D^1$ has an alkyl group as a substituent other than the substituent represented by -L-G, the alkyl group contained in the ring is preferably an alkyl group in the range of the Substituent Group A and Substituent Group B as described above; more preferably an alkyl group having 1 to 6 carbon atoms, still more preferably an alkyl group having 1 to 4 carbon atoms, and even still more preferably a methyl group.

In the general formula (1), the L represents a single bond or a linking group, preferably a divalent linking group formed by the binding of a single bond, an arylene group, or 2 or more arylene groups, more preferably a divalent linking group formed by the binding of a single bond, an arylene group having 6 to 10 carbon atoms, or 2 or more arylene groups having 6 to 10 carbon atoms, and particularly preferably a single bond, a phenylene group, or a biphenylene group.

The phenylene group represented by the L is preferably a 1,4-phenylene group or a 1,3-phenylene group. The biphenylene group represented by the L is preferably a 4,4'-biphenylene group, a 4,3'-biphenylene group, or a 3,3'-biphenylene group.

In the present invention, L of the compound represented by the general formula (1) is preferably selected from a single bond or a group selected from the following group $L^1$ of linking groups.

Group $L^1$ of Linking Groups

[Chem. 14]

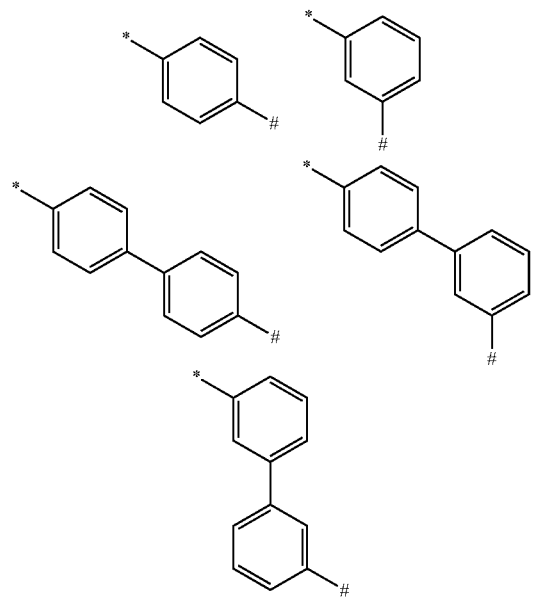

(In the formula, * represents a binding position with a 5- or 6-membered ring formed of $D^1$, $Z^4$, and a carbon atom, and # represents a binding position with G.)

L of the compound represented by the general formula (1) is more preferably a single bond or a phenylene group, and particularly preferably a single bond.

In the general formula (1), G represents a fused ring with 3 or more rings, preferably a fused ring with 3 to 5 rings, and more preferably a fused ring with 3 or 4 rings.

G may be any one of an aromatic hydrocarbon ring, an aromatic hetero ring, an aliphatic hydrocarbon ring, and a non-aromatic hetero ring; and preferably an aromatic hydrocarbon ring or an aromatic hetero ring.

Examples of the hetero atom in the case where G constitutes a fused hetero ring with 3 or more rings include a sulfur atom, a nitrogen atom, an oxygen atom, and a silicon atom, more preferably a sulfur atom, an oxygen atom, and a nitrogen atom, and still more preferably a sulfur atom.

The fused ring with 3 or more rings represented by G may have a substituent, and as the substituent on a carbon atom and the substituent on a silicon atom, the Substituent Group A and following Substituent Group B can be applied, respectively. However, the ring formed of $B^1$ does not include a fused ring with 3 or more rings.

Preferred examples of G include dibenzothiophene, dibenzofuran, carbazole, fluorene, silafluorene, phenanthrene, triphenylene, and indolocarbazole.

Above all, in the present invention, G of the compound represented by the general formula (1) is preferably represented by the following general formula $G^A$.

[Chem. 15]

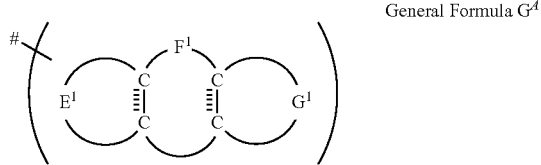

General Formula $G^A$ (In the formula, $E^1$ to $G^1$ rings each represent an atomic group which is combined with a carbon atom to form a 5- to 7-membered ring. # represents a binding position with L.)

Hereinafter, the preferred range of the compound represented by the general formula $G^A$ will be described.

Furthermore, in the present invention, the hydrogen atom in the description of the general formula $G^A$ also includes isotopes (a deuterium atom and the like), and the atoms additionally constituting the substituent are also intended to include isotopes of the atoms.

In the present invention, the "substituent" may be further substituted with a substituent. For example, the "alkyl group" in the present invention includes an alkyl group substituted with a fluorine atom (for example, a trifluoromethyl group) and an alkyl group substituted with an aryl group (for example, a triphenylmethyl group).

In the general formula $G^A$, $E^1$ represents an atomic group which is combined with a carbon atom to form a 5-, 6-, or 7-membered hydrocarbon ring or hetero ring, and examples of the 5-, 6-, or 7-membered hydrocarbon ring or hetero ring containing $E^1$ and a carbon atom (hereinafter also referred to as a ring formed of $E^1$) include a cyclopentane ring, a cyclohexane ring, a cycloheptane ring, a benzene ring, a naphthalene ring, a pyridine ring, a pyrimidine ring, a pyrazine ring, a pyridazine ring, a triazine ring, a thiophene ring, a furan ring, a pyrrole ring, an imidazole ring, a pyrazole ring, an oxazole ring, a triazole ring, a triazole ring, an oxadiazole ring, a thiadiazole ring, a morpholine ring, and a thiomorpholine ring. The ring formed of $E^1$ may be either an aromatic hydrocarbon ring, an aromatic hetero ring, and a non-aromatic hydrocarbon ring or hetero ring, but it is preferably an aromatic hydrocarbon ring. Examples of the hetero atom contained in the ring formed of $E^1$ include a sulfur atom, a nitrogen atom, an oxygen atom, and a silicon atom.

The 5-, 6-, or 7-membered hydrocarbon ring or hetero ring formed of $E^1$ and a carbon atom may have a substituent, and as the substituent on a carbon atom and the substituent on a nitrogen atom, the Substituent Group A and the Substituent Group B can be applied, respectively. In addition, in the case where the nitrogen atom constitutes an aromatic hetero ring, the nitrogen atom has no substituent.

The substituent on carbon contained in the ring formed of $E^1$ is preferably an alkyl group, an aryl group, an aromatic hetero ring group (heteroaryl group), a cyano group, or a fluorine atom in the Substituent Group A.

The substituent on nitrogen contained in the ring formed of $E^1$ is preferably an alkyl group, an aryl group, or an aromatic hetero ring group in the Substituent Group B, and more preferably an alkyl group or an aryl group.

The substituents contained in the rings formed of $E^1$ may be connected with each other to form a fused ring, and examples of the ring thus formed include a cyclopentane ring, a cyclohexane ring, a cycloheptane ring, a benzene ring, a naphthalene ring, a pyridine ring, a pyrimidine ring, a pyrazine ring, a pyridazine ring, a triazine ring, a thiophene ring, a furan ring, a pyrrole ring, an imidazole ring, a pyrazole ring, an oxazole ring, a triazole ring, a triazole ring, an oxadiazole ring, a thiadiazole, a benzothiophene ring, a benzofuran ring, an indole ring, a morpholine ring, and a thiomorpholine ring. These rings thus formed may have a substituent and examples of the substituent include the substituents on carbon atoms or the substituents on nitrogen atoms as described above.

In the present invention, for the compound represented by the general formula $G^A$, preferably, the ring formed of $E^1$ is unsubstituted or has an alkyl group, an aryl group, or a heteroaryl group. Preferably, the ring is unsubstituted or has an alkyl group, a phenyl group, or a heteroaryl group in the range of the Substituent Group A and Substituent Group B as described above; more preferably, the ring is unsubstituted or has a phenyl group; and particularly preferably, the ring is unsubstituted.

The preferred ranges of the ring formed of $G^1$ are the same as the preferred ranges of the $E^1$ ring.

In the general formula $G^A$, $F^1$ represents an atomic group which is combined with a carbon atom to form a 5-, 6-, or 7-membered hydrocarbon ring or hetero ring, and examples of the 5-, 6-, or 7-membered hydrocarbon ring or hetero ring containing $F^1$ and a carbon atom (hereinafter also referred to as a ring formed of $F^1$) include a cyclopentane ring, a cyclohexane ring, a cycloheptane ring, a benzene ring, a naphthalene ring, a pyridine ring, a pyrimidine ring, a pyrazine ring, a pyridazine ring, a triazine ring, a thiophene ring, a furan ring, a pyrrole ring, an imidazole ring, a pyrazole ring, an oxazole ring, a triazole ring, a triazole ring, an oxadiazole ring, a thiadiazole ring, a morpholine ring, and a thiomorpholine ring. The ring formed of $F^1$ may be any of an aromatic hydrocarbon ring, an aromatic hetero ring, and a non-aromatic hydrocarbon ring or hetero ring, but it is preferably a hetero ring, and more preferably a hetero ring including 5 members. Examples of the hetero atom contained in ring formed of $F^1$ include a sulfur atom, a nitrogen atom, an oxygen atom, and a silicon atom.

The 5-, 6-, or 7-membered hydrocarbon ring or hetero ring formed of $F^1$ and a carbon atom may have a substituent, and as the substituent on a carbon atom and the substituent on a nitrogen atom, the Substituent Group A and the Substituent Group B can be applied, respectively. In addition, in the case where the nitrogen atom constitutes an aromatic hetero ring, the nitrogen atom has no substituent.

The substituent on carbon contained in the ring formed of $F^1$ is preferably an alkyl group, an aryl group, an aromatic hetero ring group (heteroaryl group), a cyano group, or a fluorine atom in the Substituent Group A.

The substituent on nitrogen contained in the ring formed of $F^1$ is preferably an alkyl group, an aryl group, or an aromatic hetero ring group in the Substituent Group B, and more preferably an alkyl group or an aryl group.

The substituents contained in the rings formed of $F^1$ may be connected with each other to form fused a ring, and examples of the ring thus formed include a cyclopentane ring, a cyclohexane ring, a cycloheptane ring, a benzene ring, a naphthalene ring, a pyridine ring, a pyrimidine ring, a pyrazine ring, a pyridazine ring, a triazine ring, a thiophene ring, a furan ring, a pyrrole ring, an imidazole ring, a pyrazole ring, an oxazole ring, a triazole ring, a triazole ring, an oxadiazole ring, a thiadiazole ring, a morpholine ring, and a thiomorpholine ring. These rings thus formed may have a substituent and examples of the substituent include the substituents on carbon atoms or the substituents on nitrogen atoms as described above.

In the present invention, for the compound represented by the general formula $G^A$, preferably, the ring formed of $F^1$ is unsubstituted or has an alkyl group, an aryl group, or a heteroaryl group. Preferably, the ring is unsubstituted or has an alkyl group, a phenyl group, or a heteroaryl group in the range of the Substituent Group A and Substituent Group B as described above; more preferably, the ring is unsubstituted or has a phenyl group; and particularly preferably, the ring is unsubstituted.

Furthermore, in the present invention, G of the compound represented by the general formula (1) is preferably selected from the following Substituent Group $G^B$.

Substituent Group $G^B$

[Chem. 16]

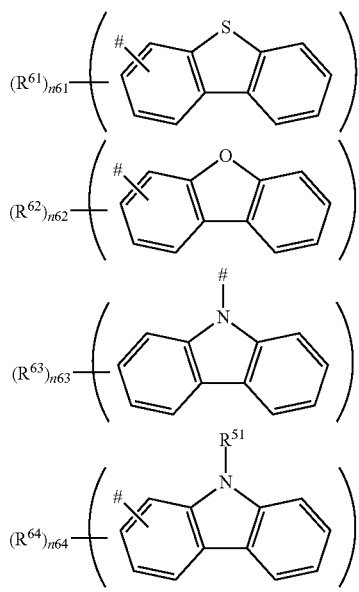

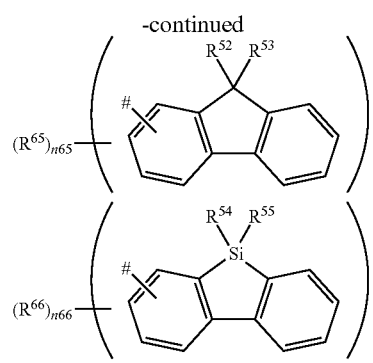

(In the formula, $R^{51}$ to $R^{55}$ each independently represent an alkyl group or an aryl group, and # represents a binding position with L. $R^{61}$ to $R^{66}$ each independently represent a hydrogen atom or a substituent, and n61 to n66 each independently represent an integer of 0 to 8.)

The preferred range of $R^{51}$ is the preferred range of the alkyl group or the aryl group described in the Substituent Group B. Above all, $R^{51}$ is preferably an aryl group, and more preferably a phenyl group.

The preferred ranges of $R^{52}$ to $R^{55}$ are the preferred range of the alkyl group or the aryl group described in the Substituent Group A. Above all, $R^{52}$ to $R^{53}$ are each independently preferably a methyl group or a phenyl group. Both $R^{52}$ and $R^{53}$ are particularly preferably an unsubstituted methyl group or an unsubstituted phenyl group. Further, the substituents represented by $R^{52}$ and $R^{53}$ may be bonded to each other to form a fused ring. Both $R^{54}$ and $R^{55}$ are particularly preferably an unsubstituted methyl group or an unsubstituted phenyl group. In addition, the substituents represented by $R^{54}$ and $R^{55}$ may be bonded to each other to form a fused ring.

The substituents $R^{61}$ to $R^{66}$ each independently represent a hydrogen atom or a substituent, and examples of the substituents represented by $R^{61}$ to $R^{66}$ include, in addition to the Substituent Group A, fused rings with 3 or more rings (a dibenzothiophenyl group, a dibenzofuranyl group, a carbazolyl group, a fluorenyl group, and a silafluorenyl group).

Preferably, the Substituent Group $G^B$ is unsubstituted or has an alkyl group, an aryl group, or a heteroaryl group; more preferably, the Substituent Group $G^B$ is unsubstituted or has an alkyl group having 1 to 6 carbon atoms, or an aryl group; still more preferably, the Substituent Group $G^B$ is unsubstituted or has a methyl group or a phenyl group; and particularly preferably, the Substituent Group $G^B$ is unsubstituted.

n61 to n66 each independently represent an integer of 0 to 8, preferably 0 to 4, more preferably 0 to 2, and still more preferably 0.

Above all, the compound represented by the general formula (1) is more preferably unsubstituted dibenzothiophene, unsubstituted dibenzofuran, carbazole, or fluorene, still more preferably unsubstituted dibenzothiophene, unsubstituted dibenzofuran, or carbazole, and particularly preferably unsubstituted dibenzothiophene.

In the general formula (1), n represents 1 or 2. n is preferably 1.

The kinds of the ligands in the compound represented by the general formula (1) (complex) are preferably classified to two kinds of ligands, from the viewpoint of easiness of synthesis. That is, in the case where n is 1, two kinds of ligands containing $Z^1$, $Z^2$, $A^1$, and $B^1$ exist, but the two existing ligands may be the same as or different from one another, and are preferably the same as one another. In the case where n is 2, two kinds of ligands containing $Z^3$, $Z^4$, $C^1$, $D^1$, L, and G exist, but the two existing ligands may be the same as or different from one another, and are preferably the same as one another.

In the present invention, the compound represented by the general formula (1) is preferably a compound represented by the following general formula (2).

[Chem. 17]

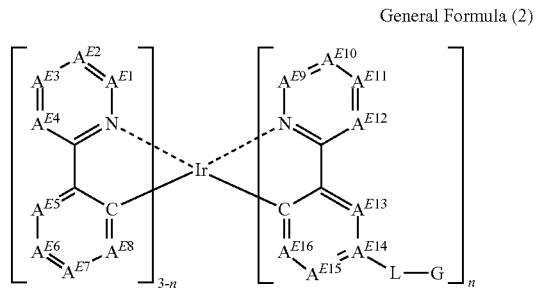

General Formula (2)

In the general formula (2), $A^{E1}$ to $A^{E13}$, $A^{E15}$, and $A^{E16}$ each independently represent a nitrogen atom or $C—R^E$. A plurality of $R^E$s each independently represent a hydrogen atom or a substituent. $A^{E14}$ represents a carbon atom. n represents 1 or 2. L represents a single bond or a linking group. G represents a fused ring with 3 or more rings. However, $R^E$ does not include a fused ring with 3 or more rings.

The preferred ranges of n, L, and G in the general formula (2) are each the same as the preferred ranges of n, L, and G in the general formula (1).

In the general formula (2), $A^{E1}$ to $A^{E13}$, $A^{E15}$, and $A^{E16}$ each independently represent a nitrogen atom or $C—R^E$, and $R^E$s may be connected with each other to form a ring. However, $R^E$ does not include a fused ring with 3 or more rings. Examples of the ring formed by the connection of $R^E$s include a ring in which substituents contained in the rings formed of $A^1$ as mentioned above in the general formula (1) are connected and fused with one another, a ring in which substituents contained in the rings formed of $B^1$ are connected and fused with one another, a ring in which substituents contained in the rings formed of $C^1$ are connected and fused with one another, and a ring in which substituents contained in the rings formed of $D^1$ are connected and fused with one another.

Examples of the substituent represented by $R^E$ include those mentioned as the Substituent Group A.

In the general formula (2), $A^{E1}$ to $A^{E4}$ each independently preferably represent $C—R^E$, and the preferred ranges of $R^E$ are each independently the same as the preferred ranges of the substituent on carbon contained in the ring formed of $A^1$ in the general formula (1).

In the general formula (2), $A^{E5}$ to $A^{E8}$ each independently preferably represent $C—R^E$, and the preferred ranges of $R^E$ are each independently the same as the preferred ranges of the substituent on carbon contained in the ring formed of $B^1$ in the general formula (1).

In the general formula (2), $A^{E9}$ to $A^{E12}$ each independently preferably represent $C—R^E$, and the preferred ranges of $R^E$ are each independently the same as the preferred ranges of the substituent on carbon contained in the ring formed of $C^1$ in the general formula (1).

In the general formula (2), $A^{E13}$, $A^{E15}$, and $A^{E16}$ each independently preferably represent $C—R^E$, and the preferred ranges of $R^E$ are each independently the same as the preferred ranges of the substituent on carbon contained in the ring formed of $D^1$ in the general formula (1).

In the present invention, the compound represented by the general formula (1) is preferably a compound represented by the following general formula (3).

[Chem. 18]

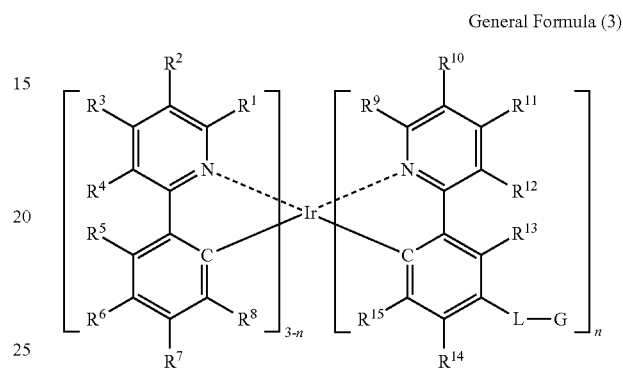

General Formula (3)

In the general formula (3), $R^1$ to $R^{15}$ each independently represent a hydrogen atom, an alkyl group, an aryl group or a heteroaryl group. n represents 1 or 2. L represents a single bond or a linking group. G represents a fused ring with 3 or more rings. However, $R^1$ to $R^{15}$ does not include a fused ring with 3 or more rings.

The preferred ranges of n, L, and G in the general formula (3) are each the same as the preferred ranges of n, L, and G in the general formula (1).

In the general formula (3), $R^1$ to $R^4$ each independently represent a hydrogen atom, an alkyl group, an aryl group, or a heteroaryl group. The alkyl group represented by each of $R^1$ to $R^4$ in the general formula (3) is preferably an alkyl group having 1 to 6 carbon atoms, more preferably an alkyl group having 1 to 4 carbon atoms, and particularly preferably a methyl group. The aryl group represented by each of $R^1$ to $R^4$ in the general formula (3) is preferably an aryl group having 6 to 10 carbon atoms, more preferably a phenyl group, a tolyl group, or a xylyl group, and particularly preferably a phenyl group.

Above all, $R^1$ to $R^4$ are each independently preferably a hydrogen atom or an alkyl group.

The number of substituents in $R^1$ to $R^4$ in the general formula (3) is the same as the preferred range of the number of substituents contained in the ring formed of $A^1$ in the general formula (1).

Out of $R^1$ to $R^4$ in the general formula (3), $R^1$ or $R^4$ preferably has a substituent, and $R^1$ more preferably has a substituent.

In the general formula (3), $R^5$ to $R^8$ each independently represent a hydrogen atom, an alkyl group, an aryl group, or a heteroaryl group. The alkyl group represented by each of $R^5$ to $R^8$ in the general formula (3) is preferably an alkyl group having 1 to 6 carbon atoms, more preferably an alkyl group having 1 to 4 carbon atoms, and particularly preferably a methyl group. The aryl group represented by each of $R^5$ to $R^8$ in the general formula (3) is preferably an aryl group having 6 to 10 carbon atoms, more preferably a phenyl group, a tolyl group, or a xylyl group, and particularly preferably a phenyl group.

Above all, $R^5$ to $R^8$ are each independently preferably a hydrogen atom or an alkyl group.

The number of substituents in $R^5$ to $R^8$ in the general formula (3) is the same as the preferred range of the number of substituents contained in the ring formed of $B^1$ in the general formula (1). Out of $R^5$ to $R^8$ in the general formula (3), it is preferable that $R^5$ or $R^6$ have a substituent. However, it is more preferable that $R^5$ to $R^8$ have no substituent and be all hydrogen atoms.

In the general formula (3), $R^9$ to $R^{12}$ each independently represent a hydrogen atom, an alkyl group, an aryl group, or a heteroaryl group. The alkyl group represented by each of $R^9$ to $R^{12}$ in the general formula (3) is preferably an alkyl group having 1 to 6 carbon atoms, more preferably an alkyl group having 1 to 4 carbon atoms, and particularly preferably a methyl group. The aryl group represented by each of $R^9$ to $R^{12}$ in the general formula (3) is preferably an aryl group having 6 to 10 carbon atoms, more preferably a phenyl group, a tolyl group, or a xylyl group, and particularly preferably a phenyl group.

Above all, $R^9$ to $R^{12}$ each independently represent a hydrogen atom or an alkyl group.

The number of substituents in $R^9$ to $R^{12}$ in the general formula (3) is the same as the preferred range of the number of substituents contained in the ring formed of $C^1$ in the general formula (1). Out of $R^9$ to $R^{12}$ in the general formula (3), it is preferable that $R^9$, $R^{10}$, or $R^{12}$ have a substituent. However, it is more preferable that $R^9$ to $R^{12}$ have no substituent and be all hydrogen atoms.

In the general formula (3), $R^{13}$ to $R^{15}$ each independently represent a hydrogen atom, an alkyl group, an aryl group, or a heteroaryl group. The alkyl group represented by each of $R^{13}$ to $R^{15}$ in the general formula (3) is preferably an alkyl group having 1 to 6 carbon atoms, more preferably an alkyl group having 1 to 4 carbon atoms, and particularly preferably a methyl group. The aryl group represented by each of $R^{13}$ to $R^{15}$ in the general formula (3) is preferably an aryl group having 6 to 10 carbon atoms, more preferably a phenyl group, a tolyl group, or a xylyl group, and particularly preferably a phenyl group.

Above all, $R^{13}$ to $R^{15}$ each independently represent a hydrogen atom or an alkyl group.

The number of substituents in $R^{13}$ to $R^{15}$ in the general formula (3) is the same as the preferred range of the number of substituents contained in the ring formed of $D^1$ in the general formula (1). Out of $R^{13}$ to $R^{15}$ in the general formula (3), it is preferable that $R^{14}$ have a substituent. However, it is more preferable that $R^{13}$ to $R^{15}$ have no substituent and be all hydrogen atoms.

Preferred specific examples of the compound represented by the general formula (1) are listed below, but the present invention is not limited to the following compounds.

[Chem. 19]

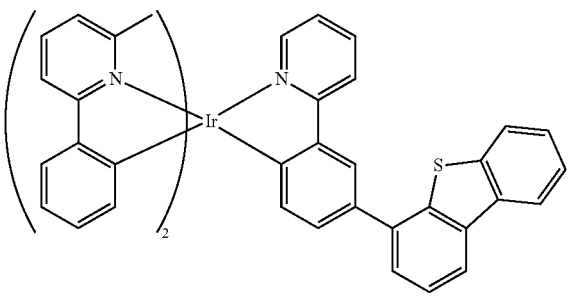

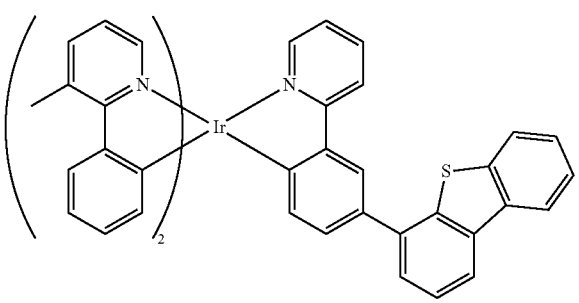

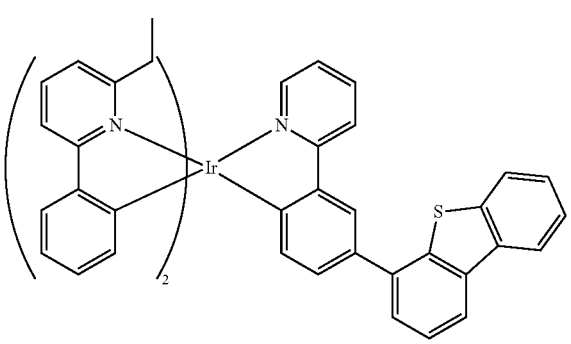

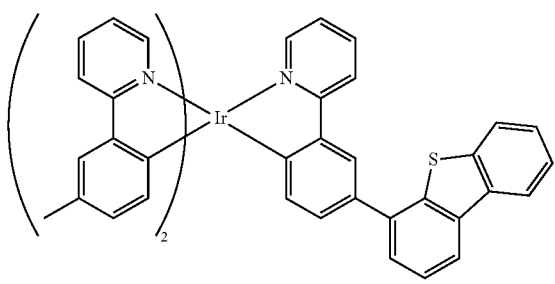

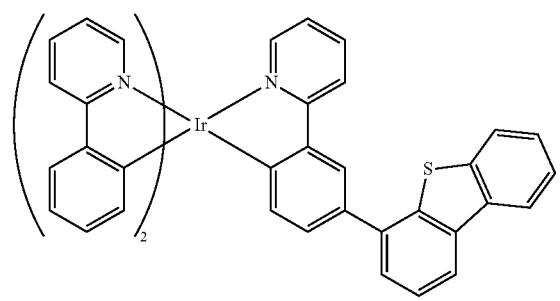

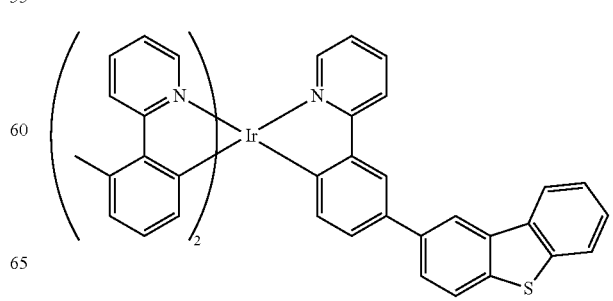

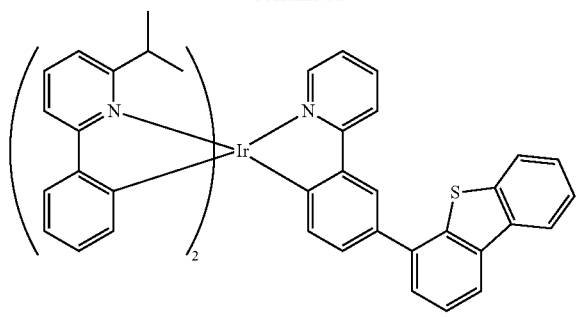
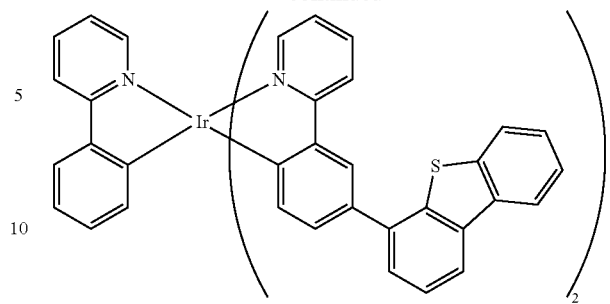
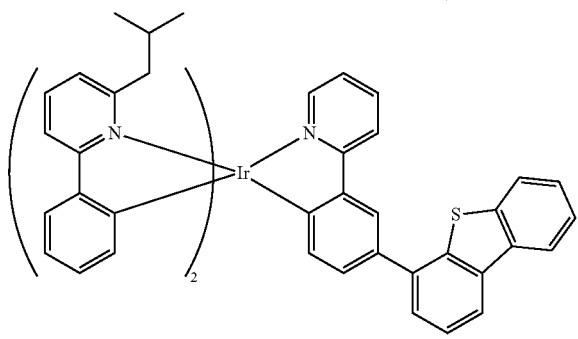
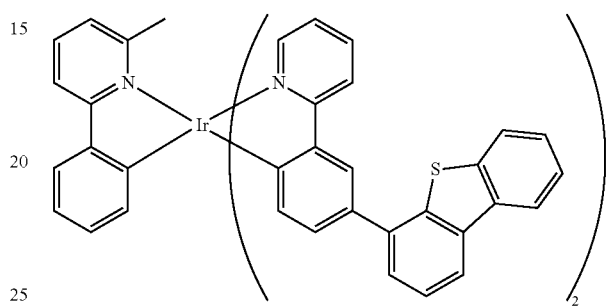
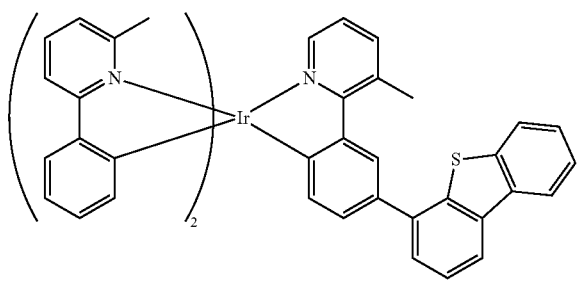
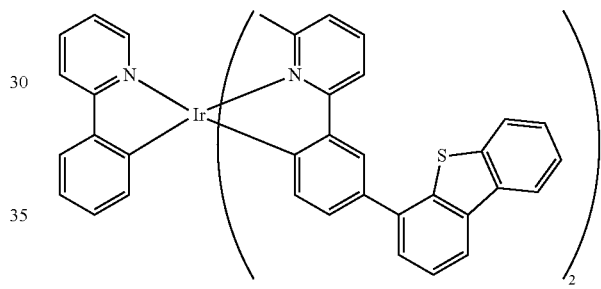
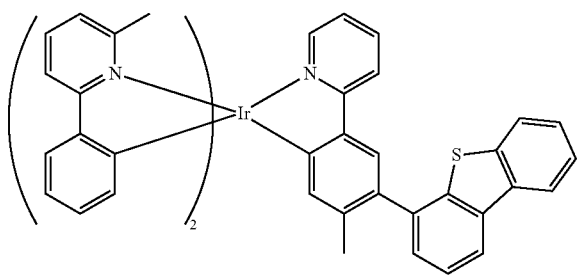
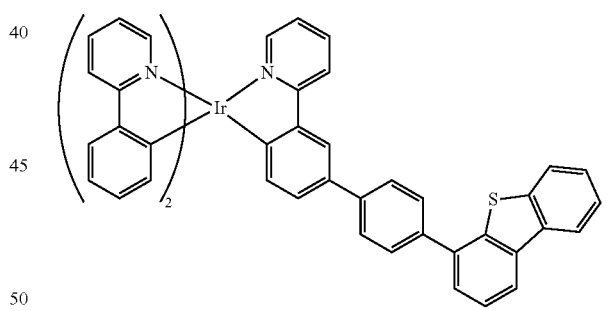
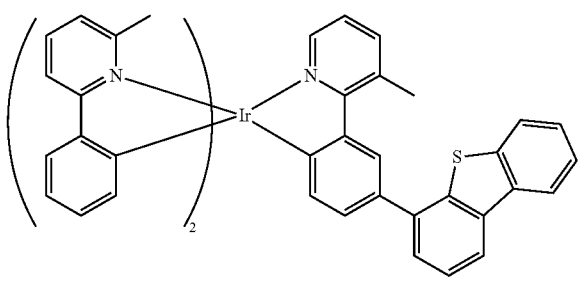
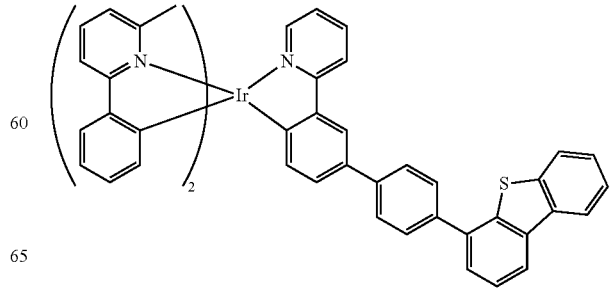

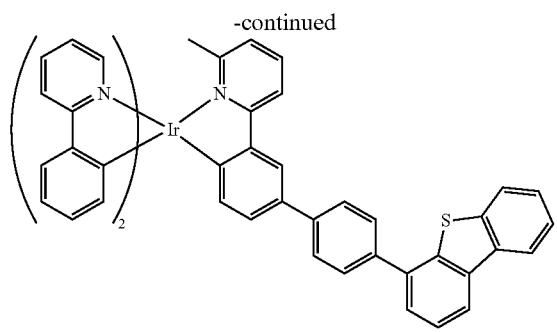
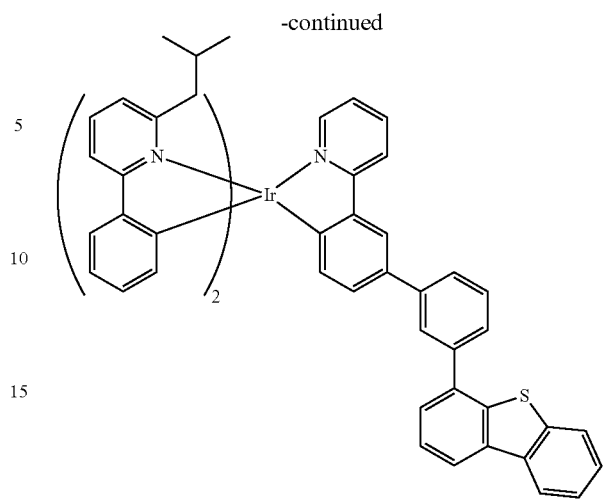
[Chem. 20]
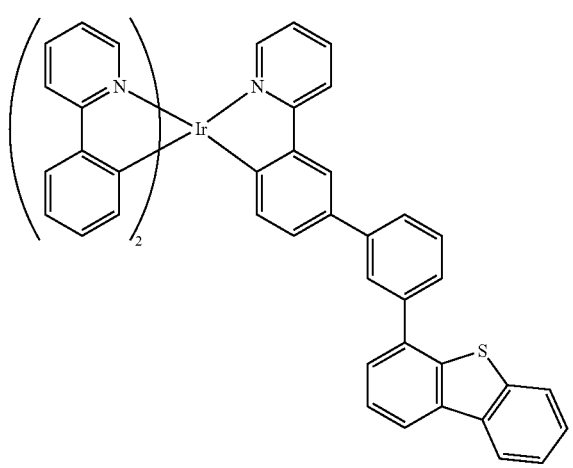
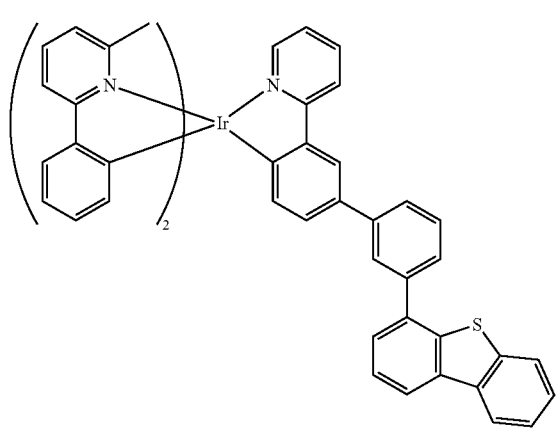

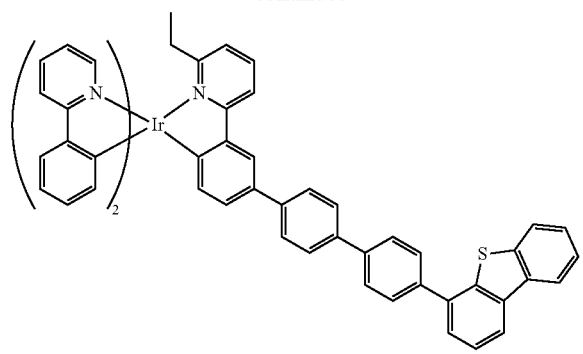
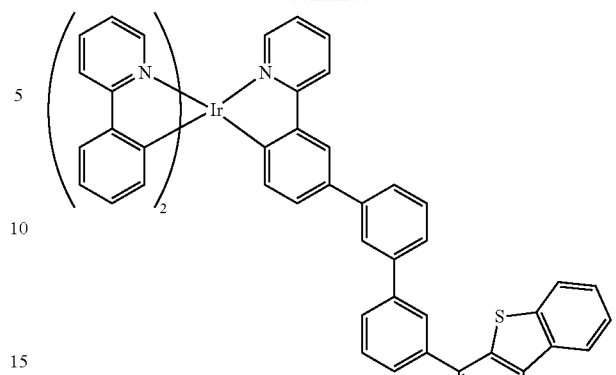
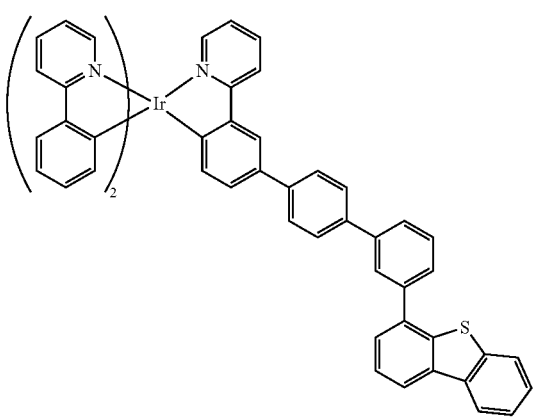
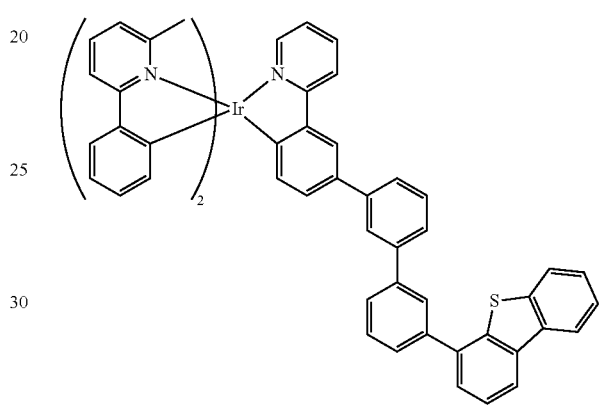
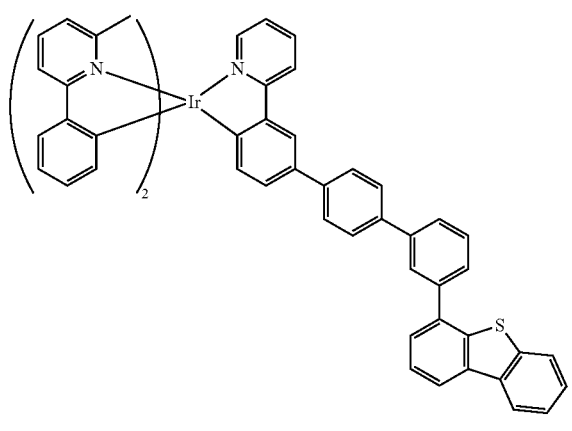
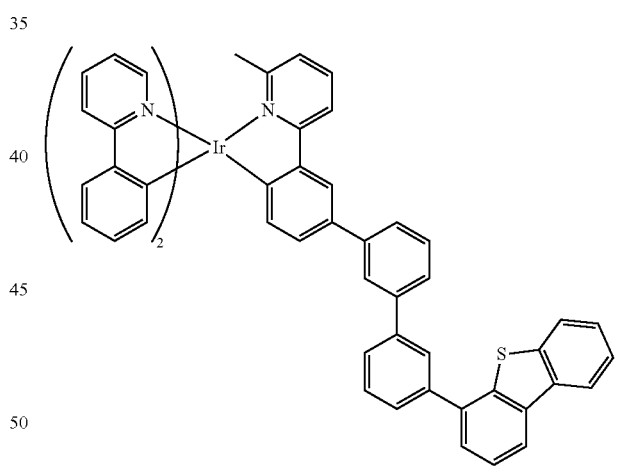
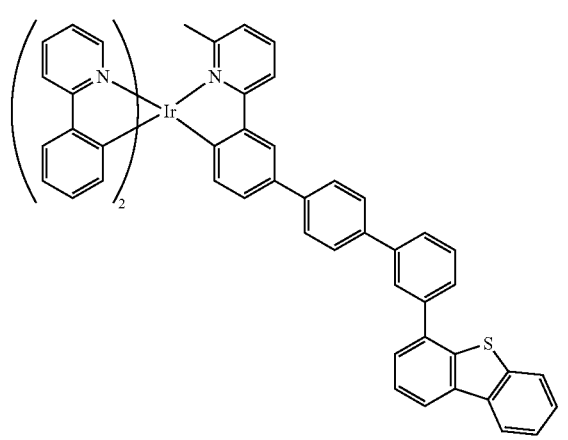
[Chem. 21]
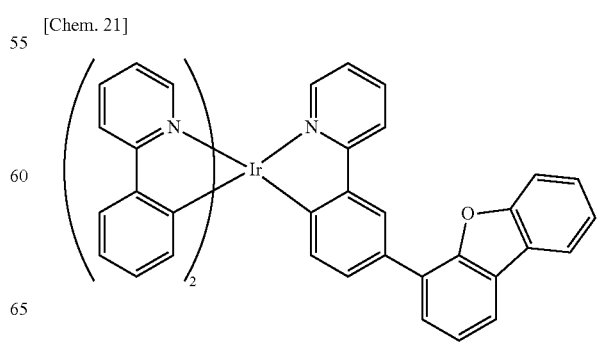

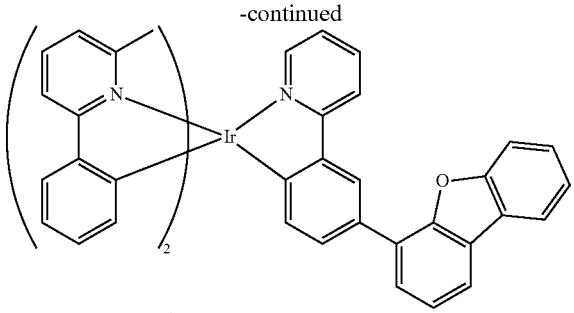
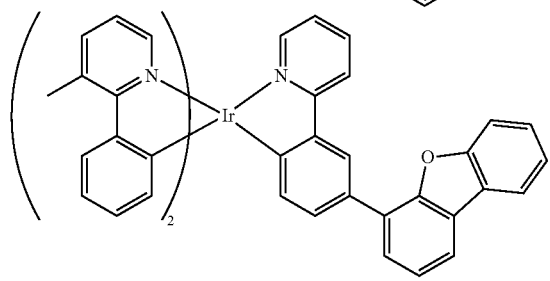
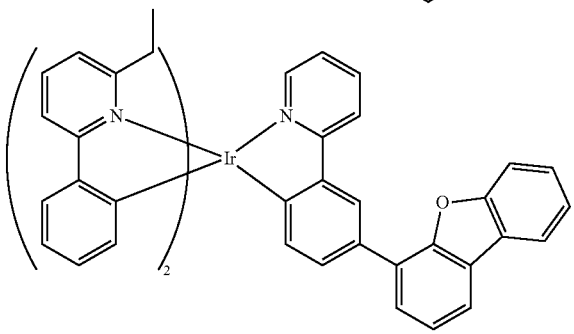
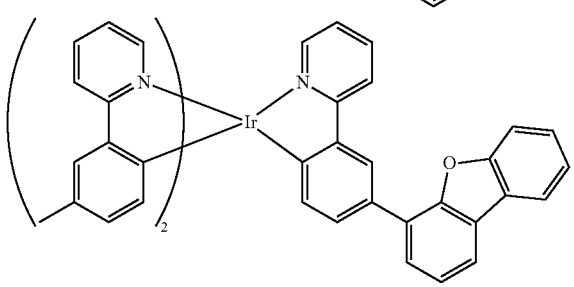
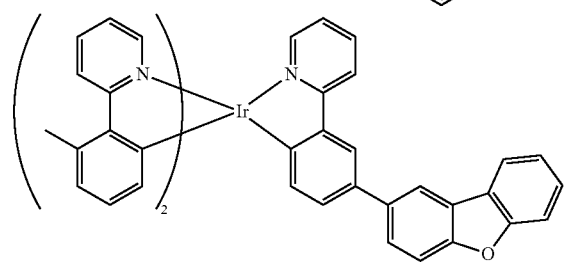
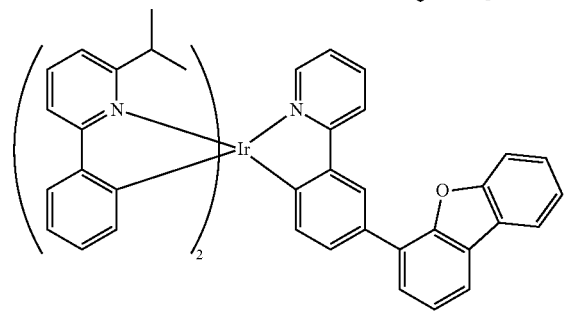
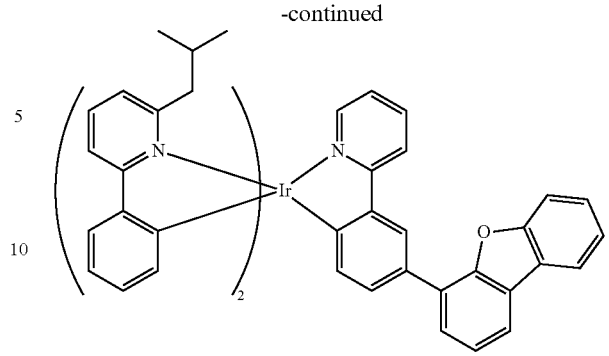
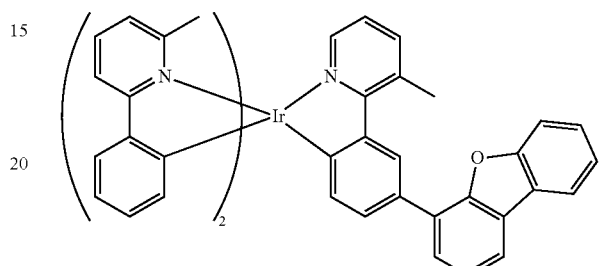
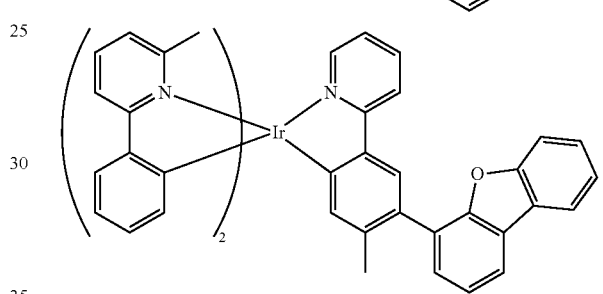
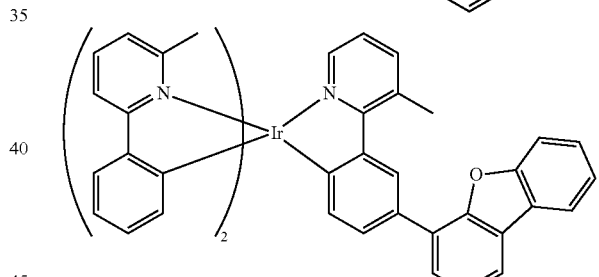
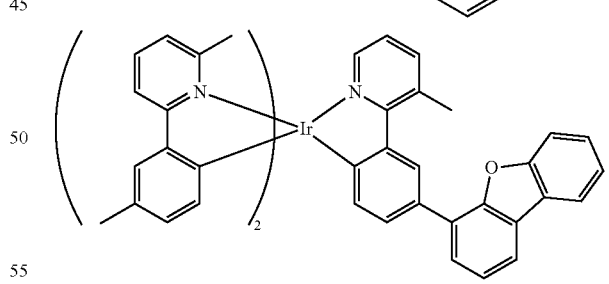
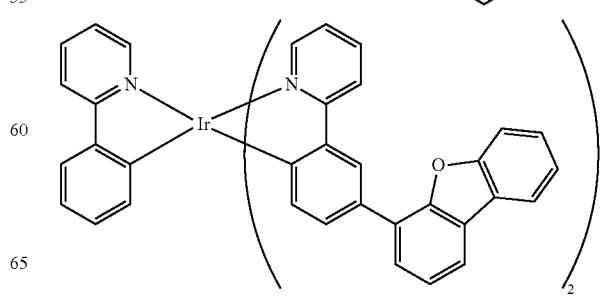

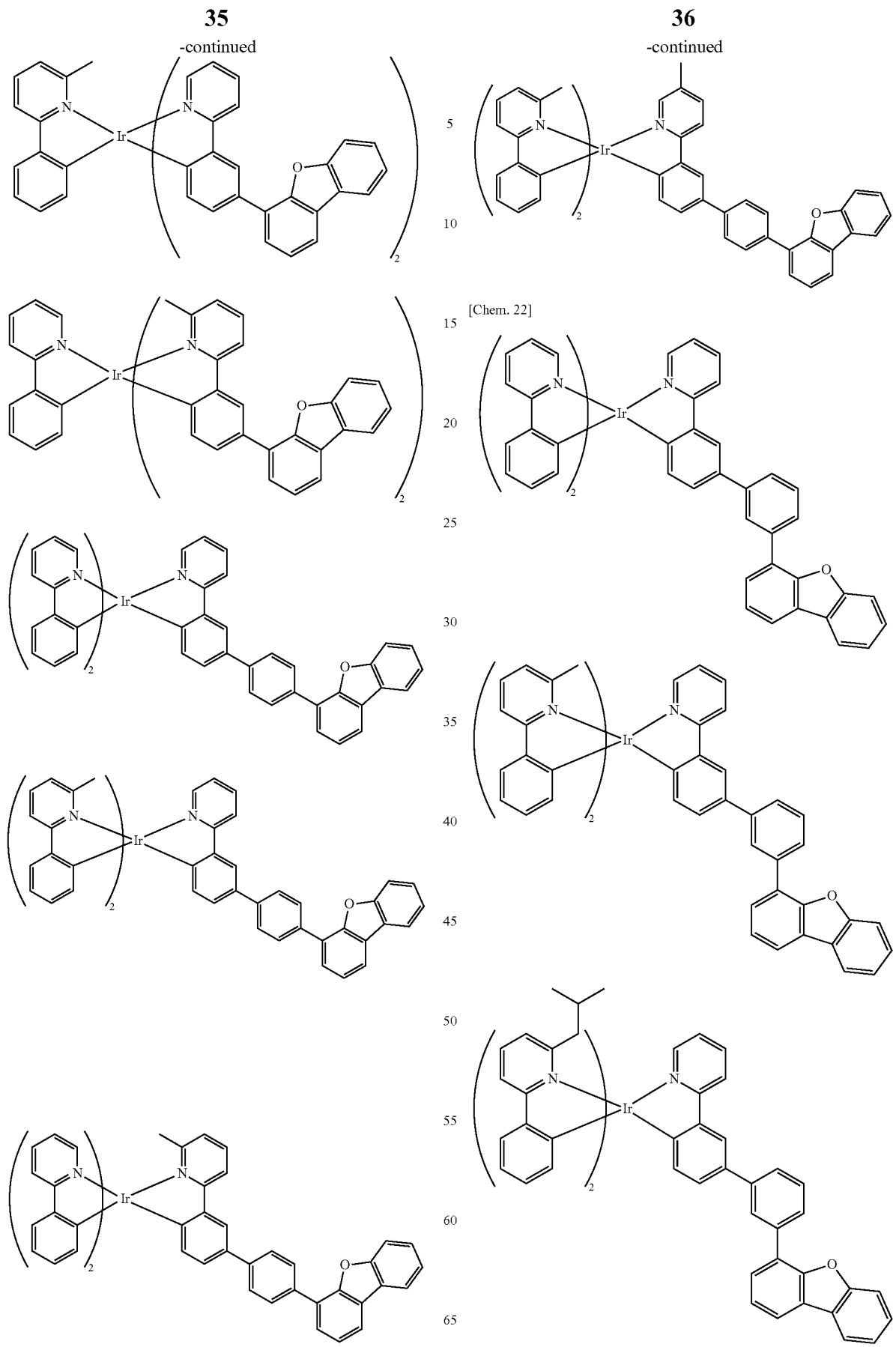

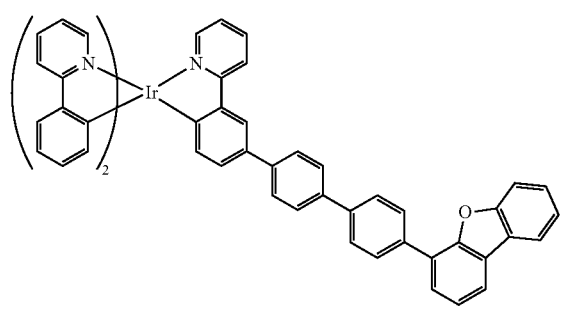
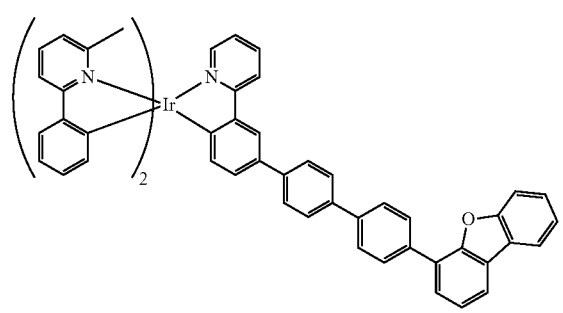
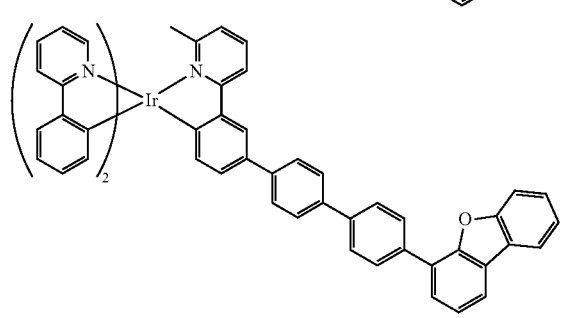
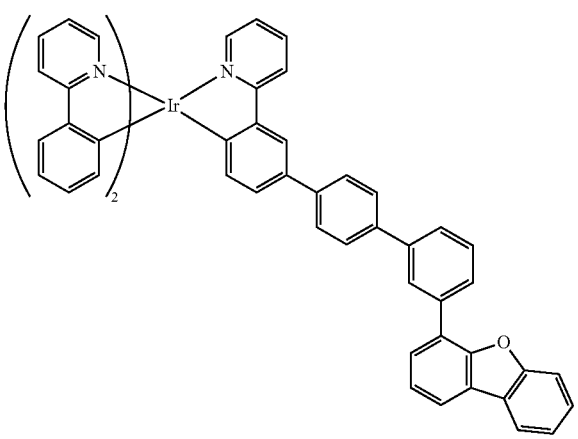
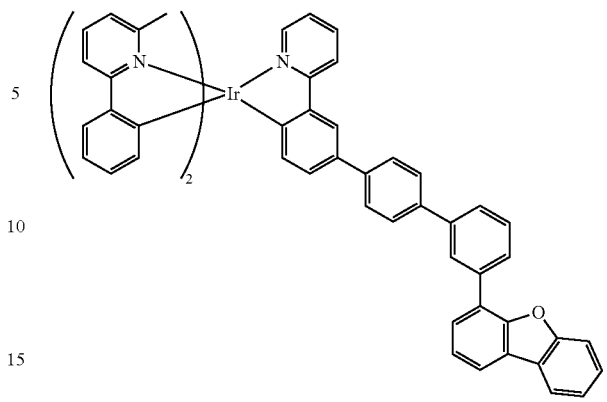
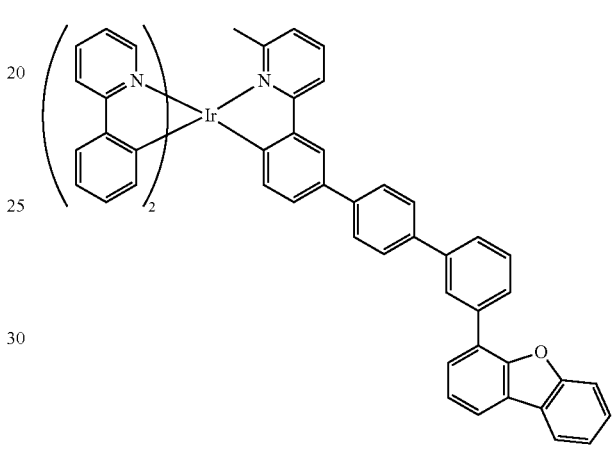
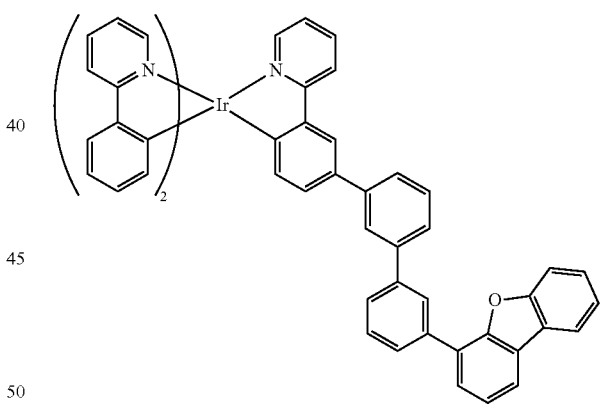
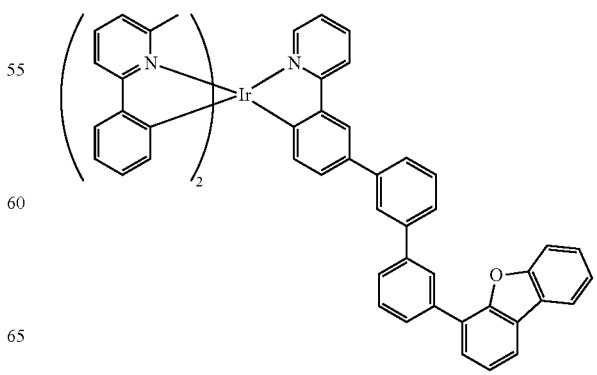

[Chem. 23]
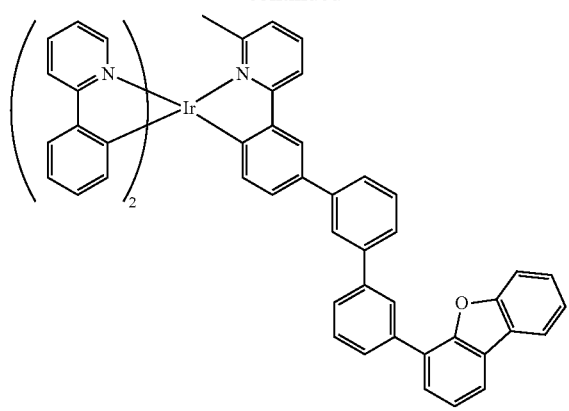
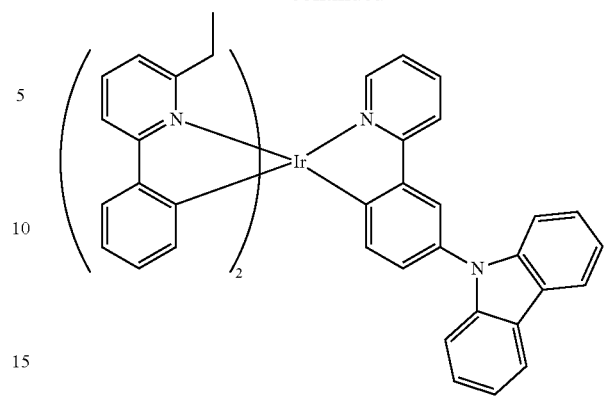
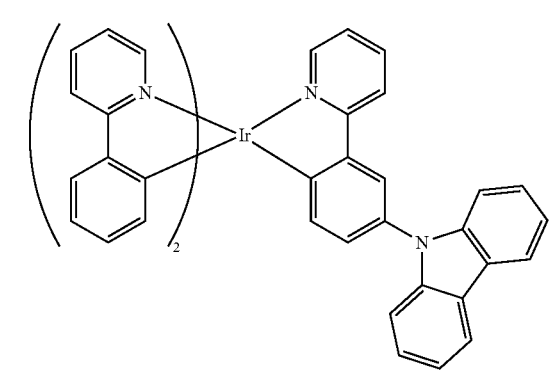
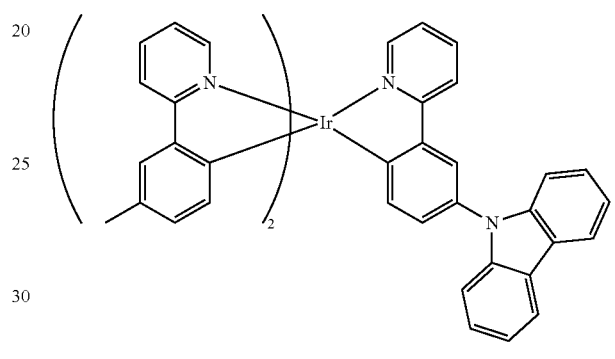
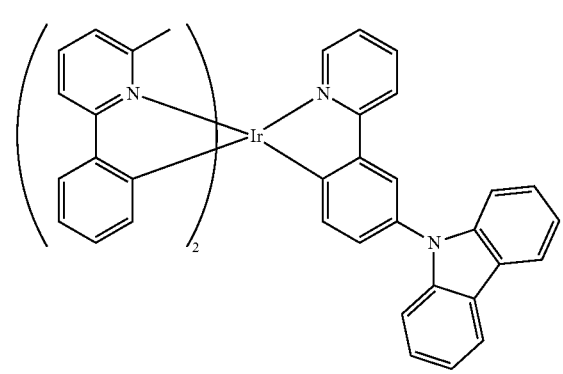
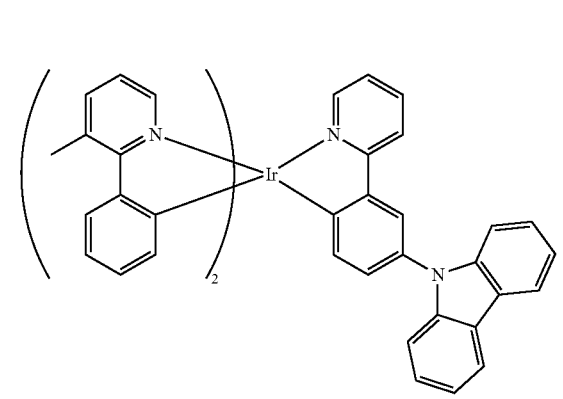
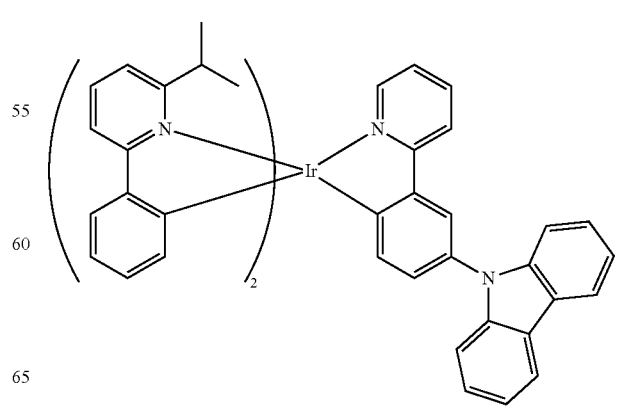

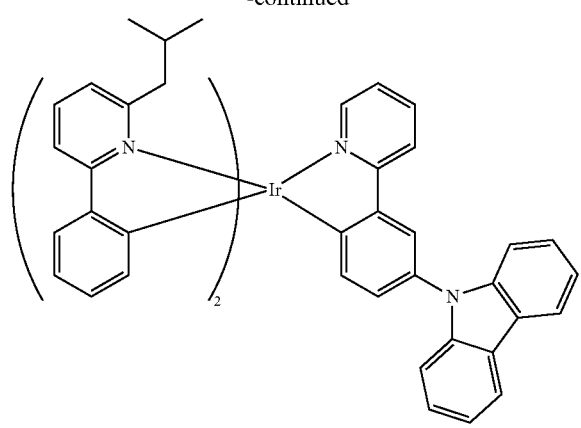
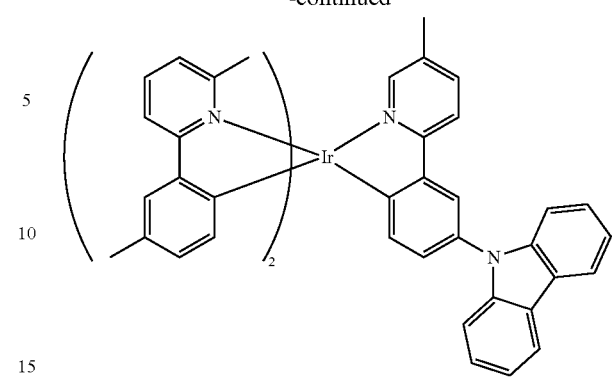
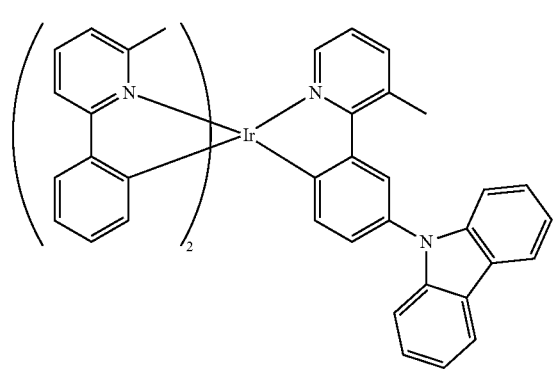
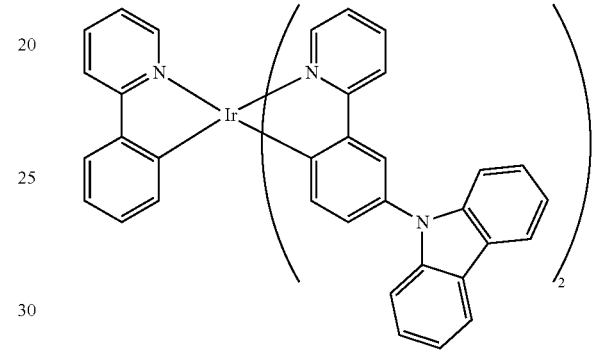
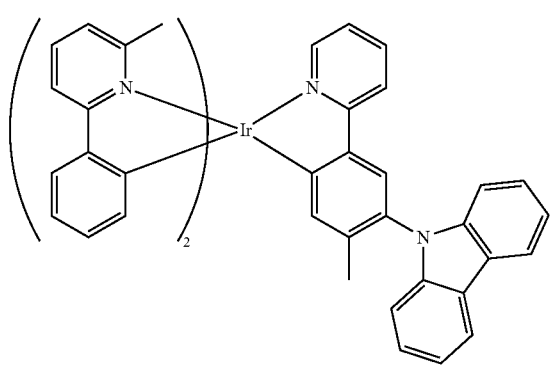
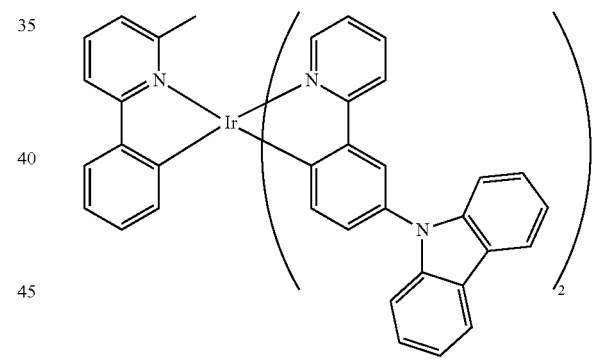
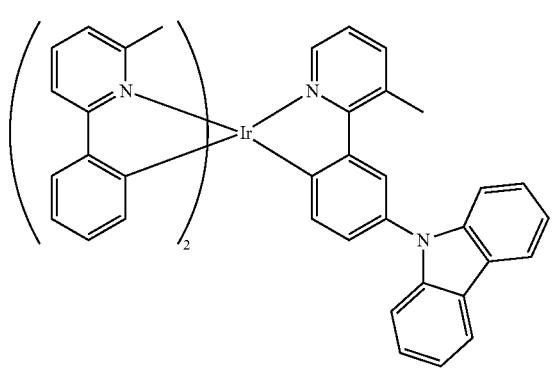
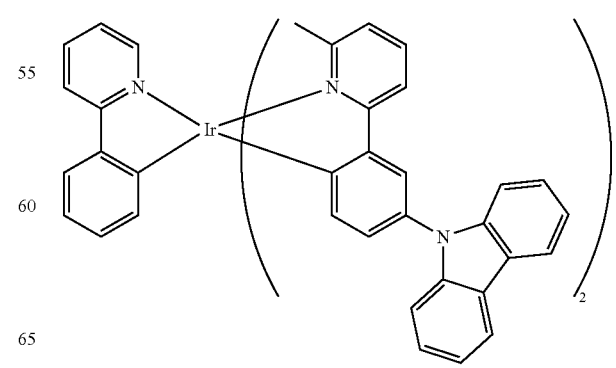

-continued
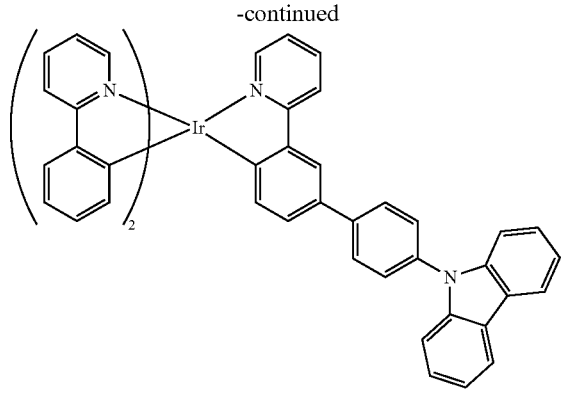
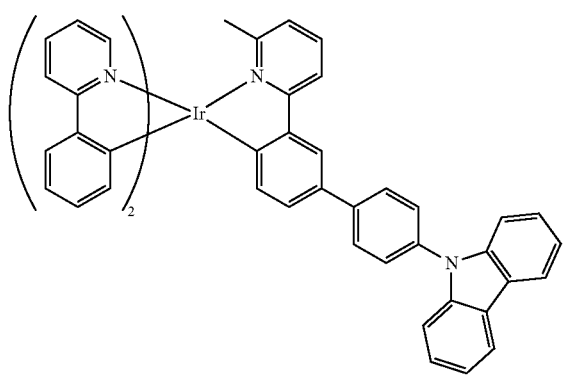
[Chem. 24]
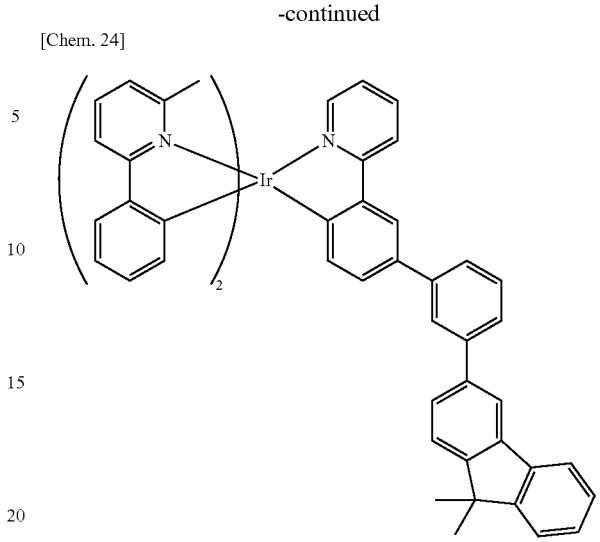
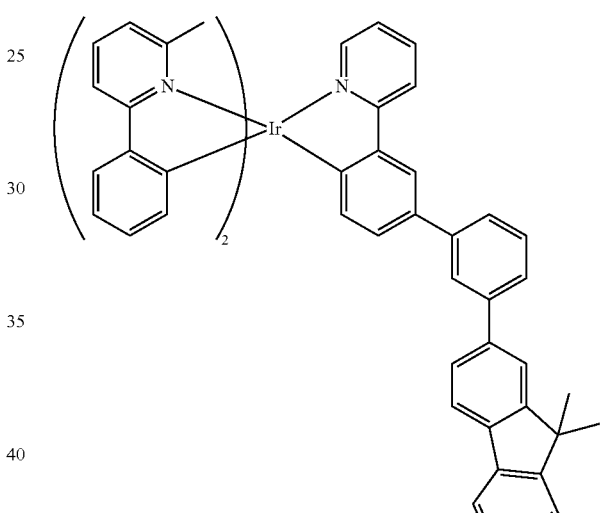
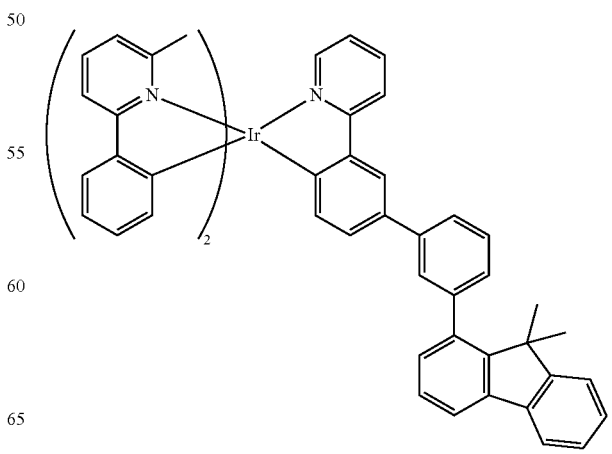

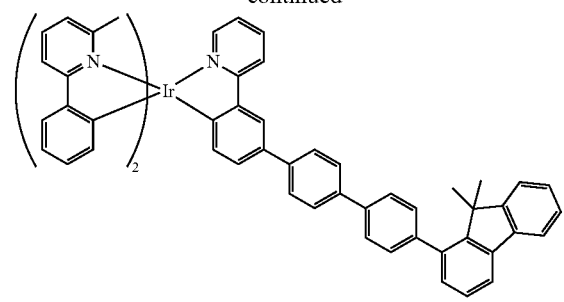
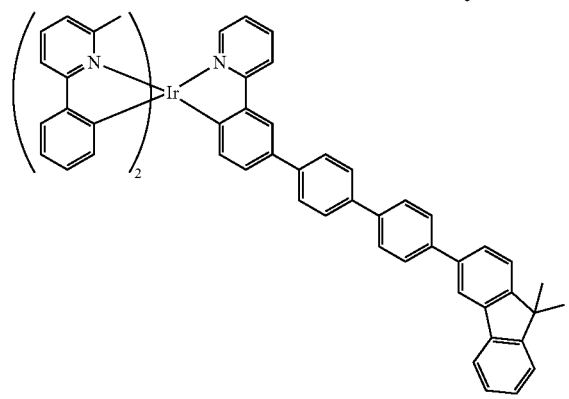
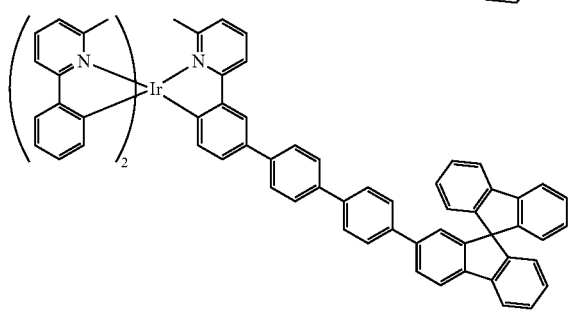
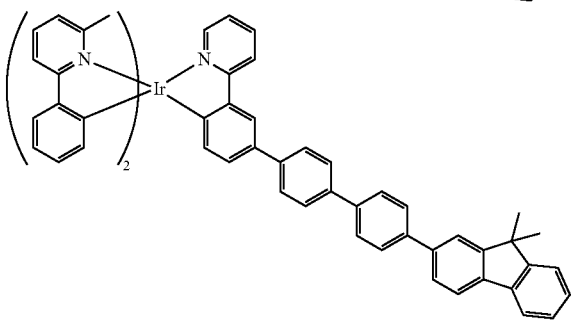
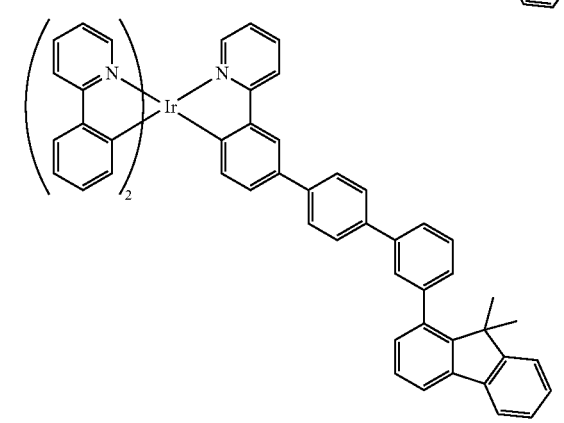
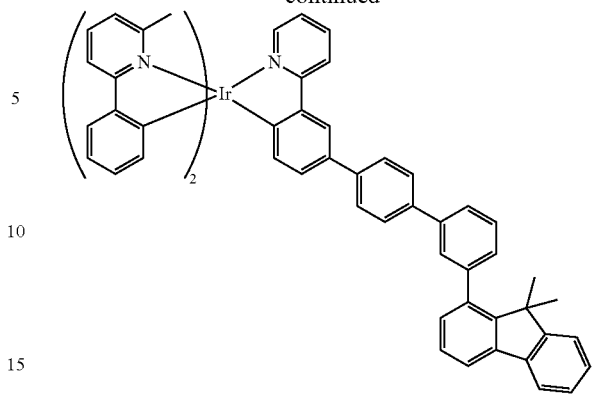
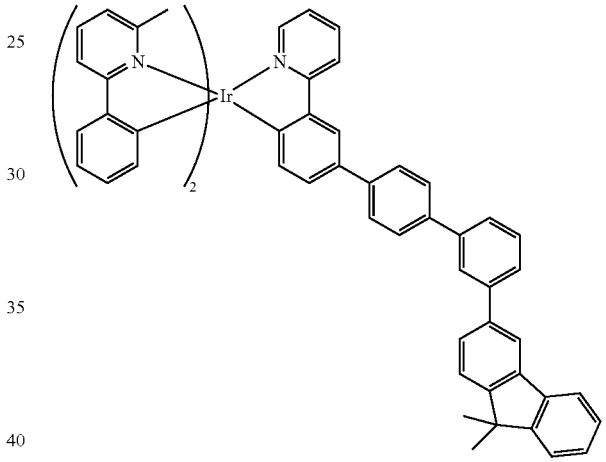
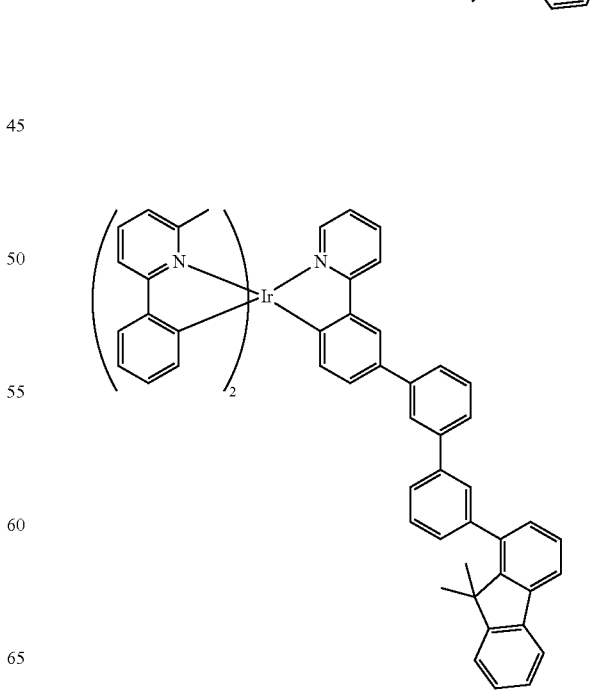

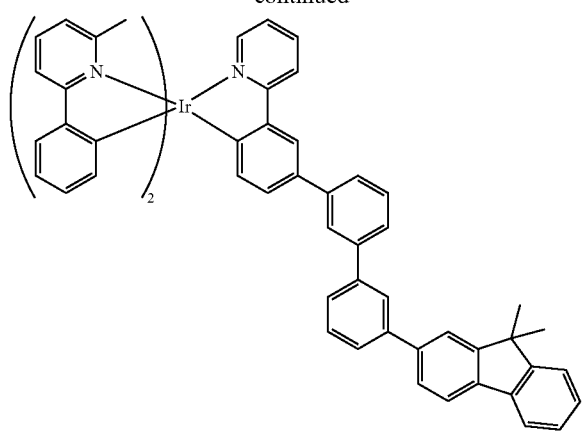
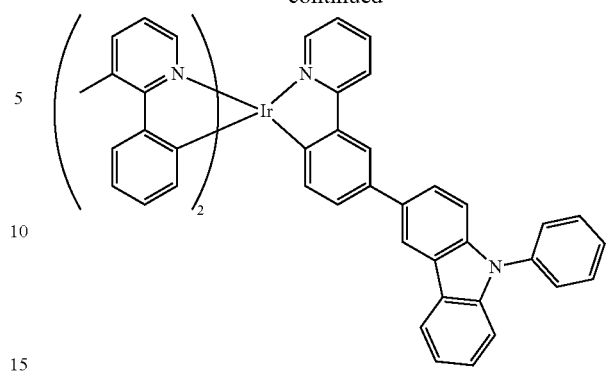
[Chem. 25]
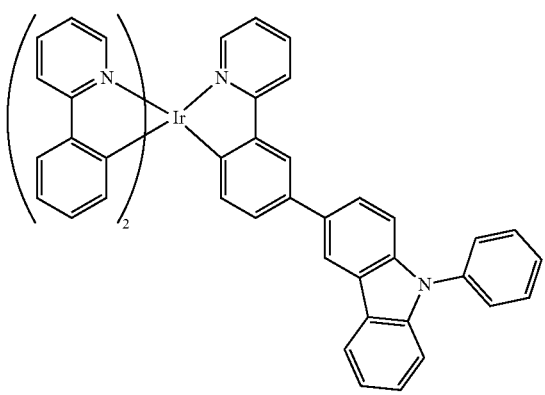
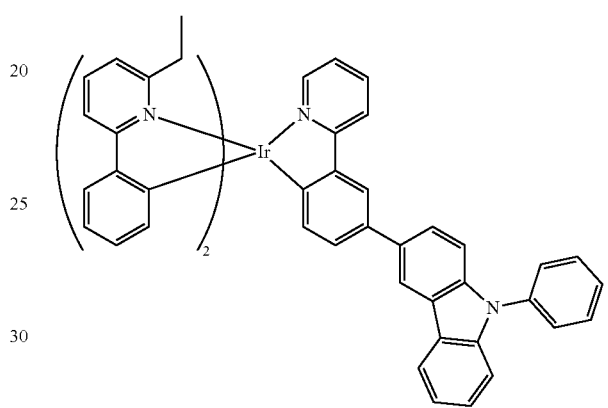
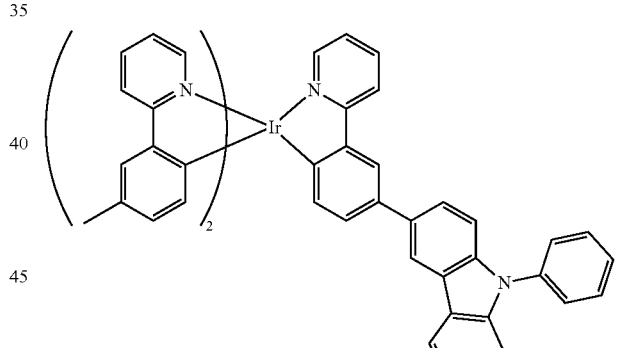
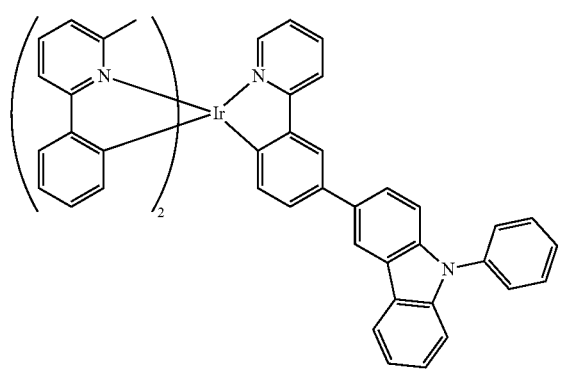
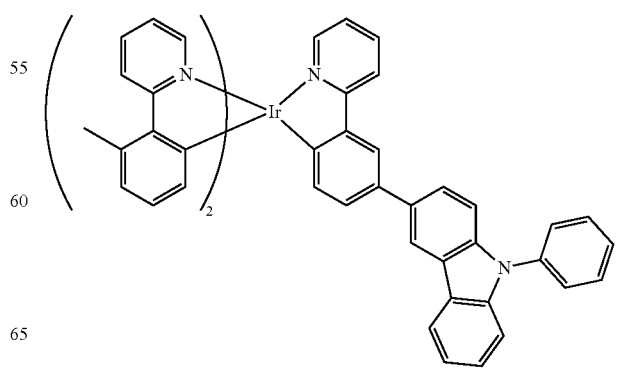

49
-continued
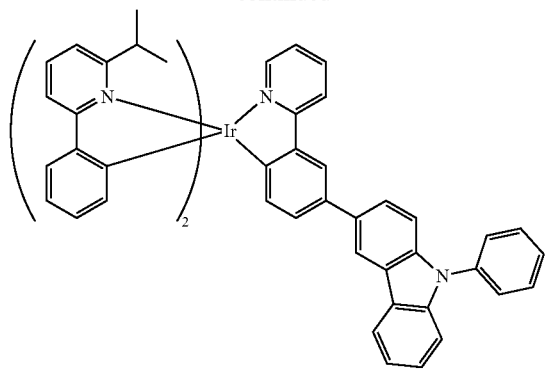
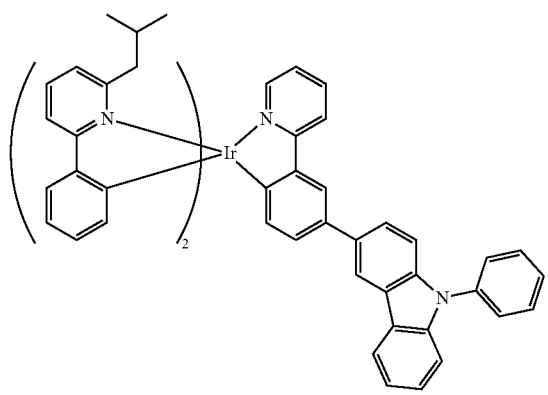
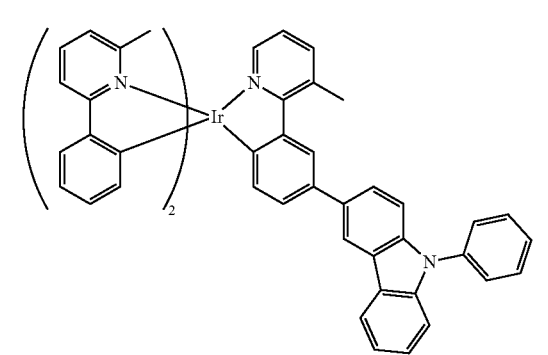
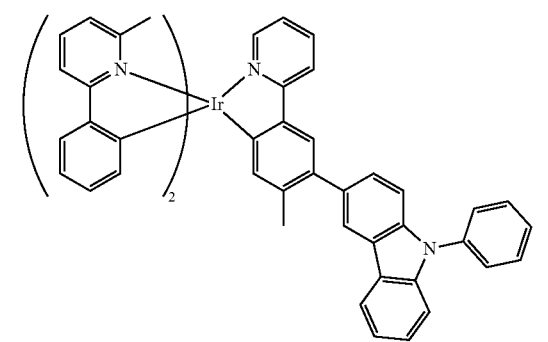
50
-continued
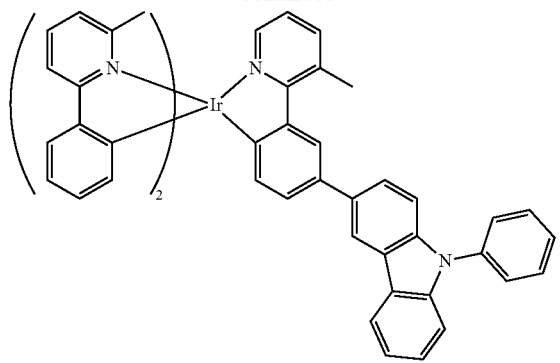
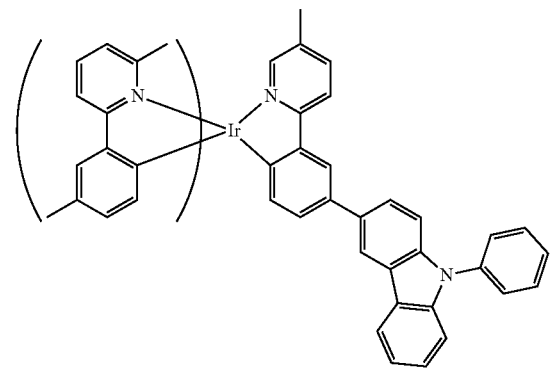
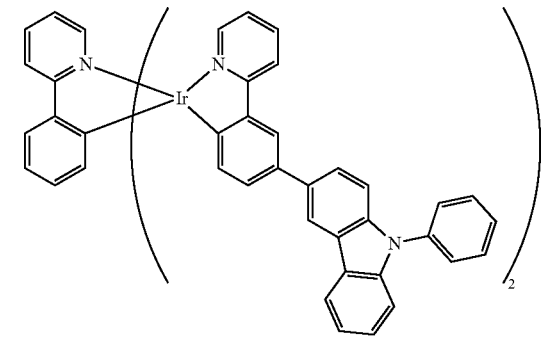
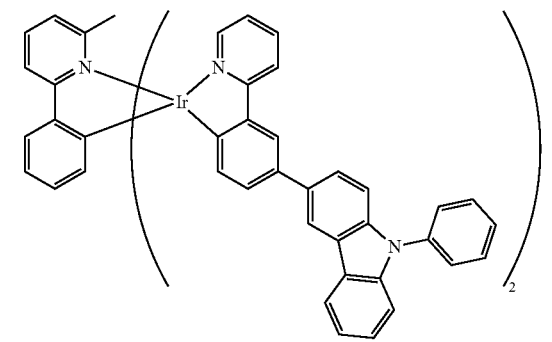

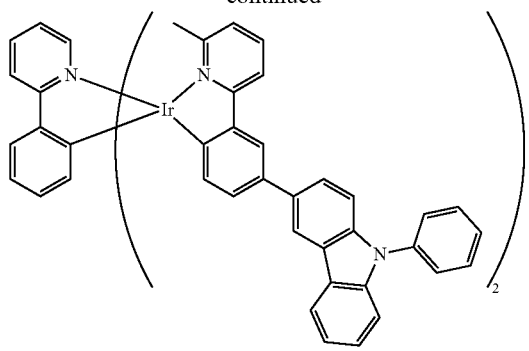
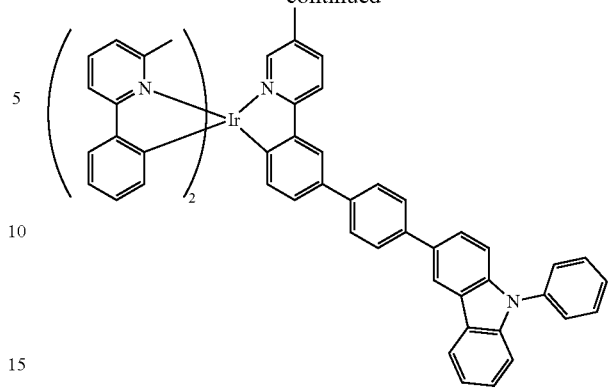
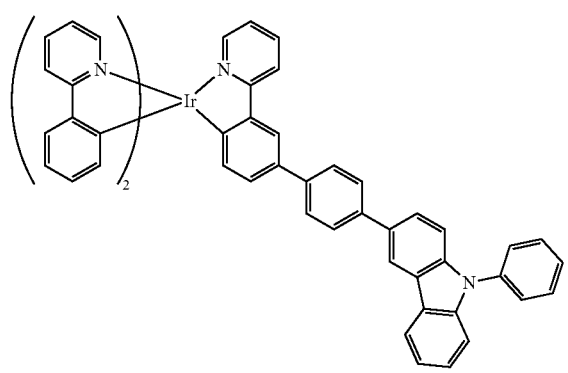
[Chem. 26]
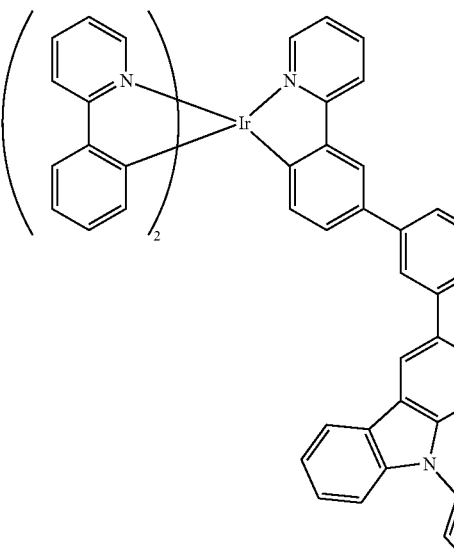
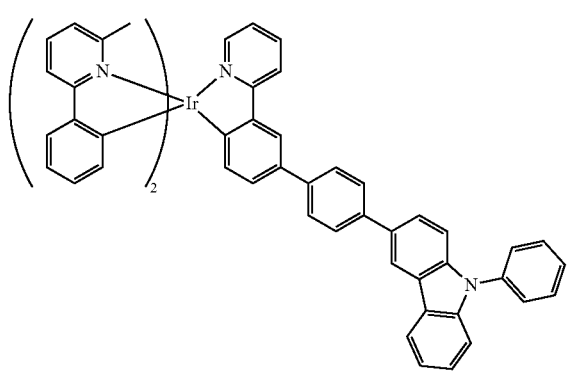
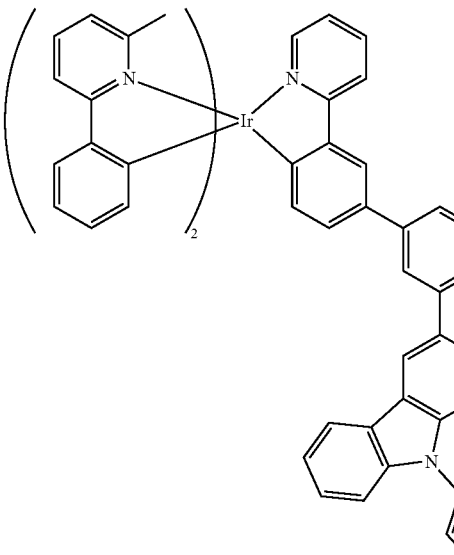
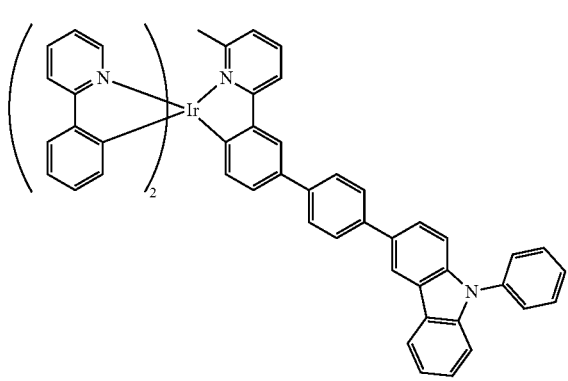

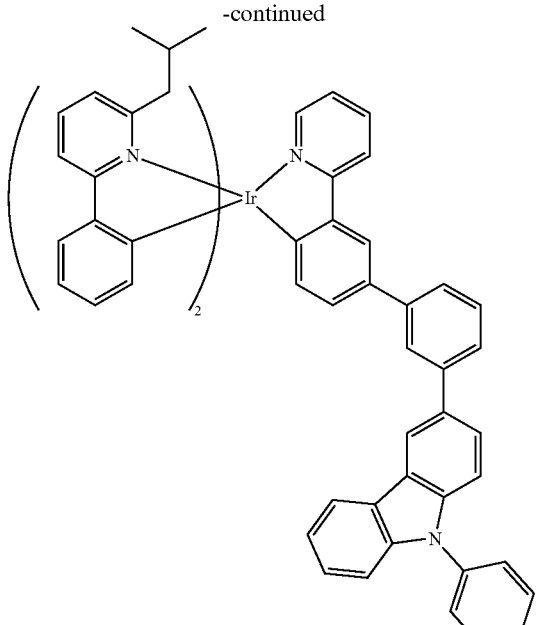
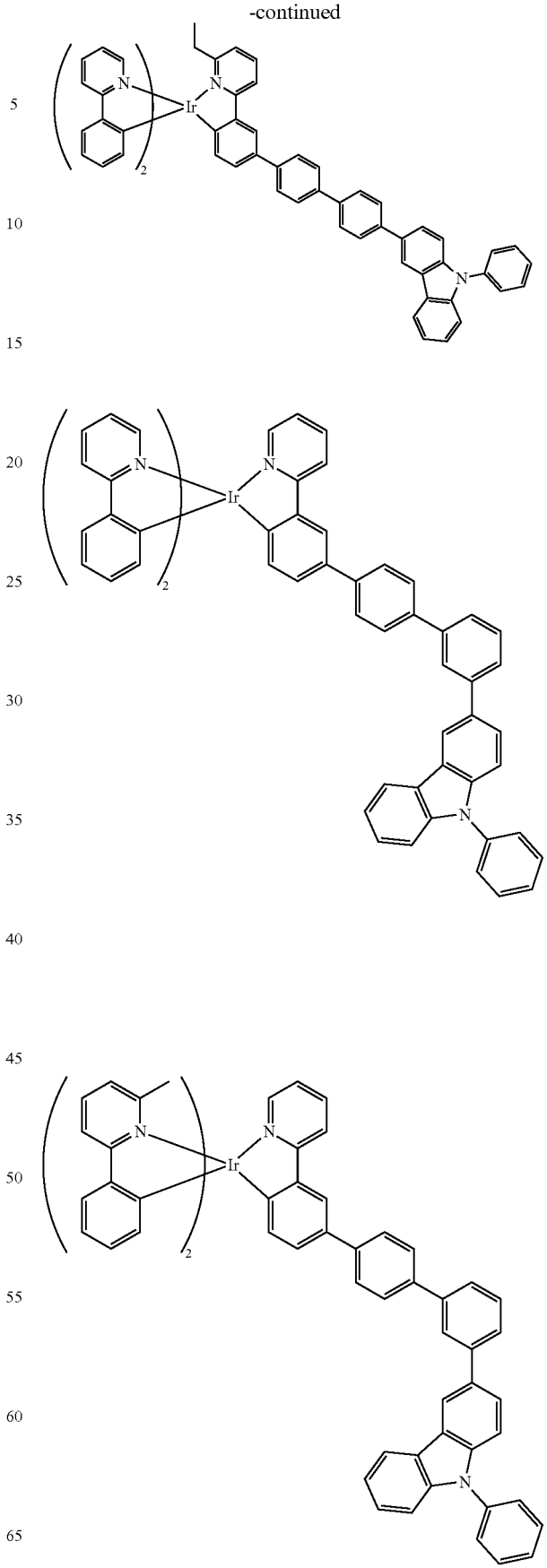

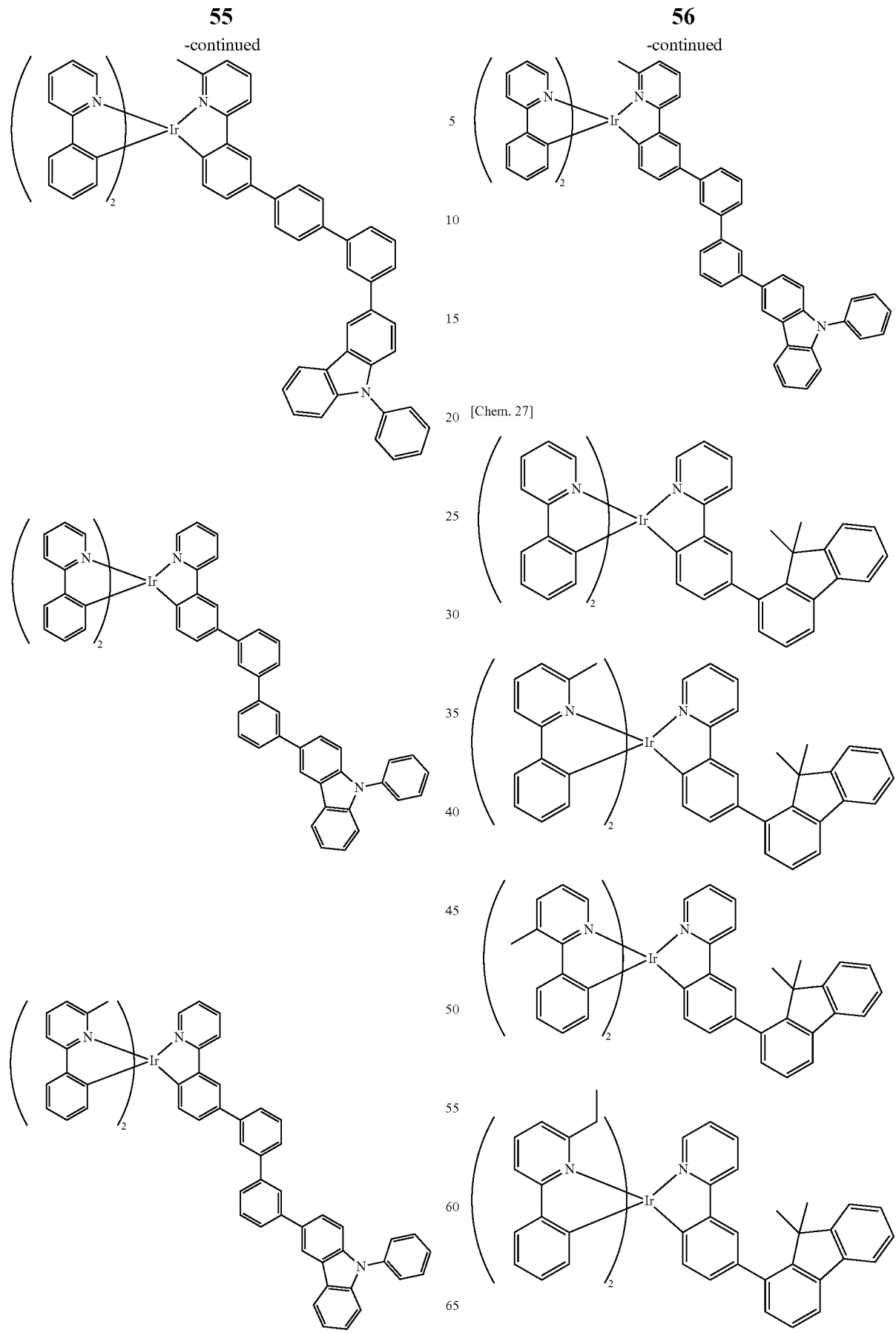

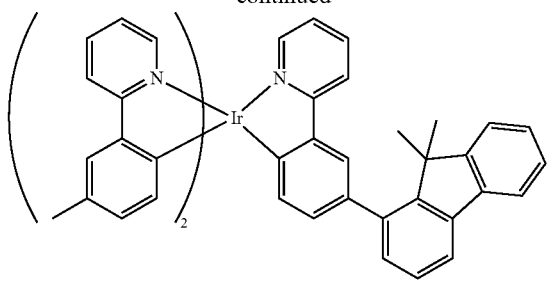
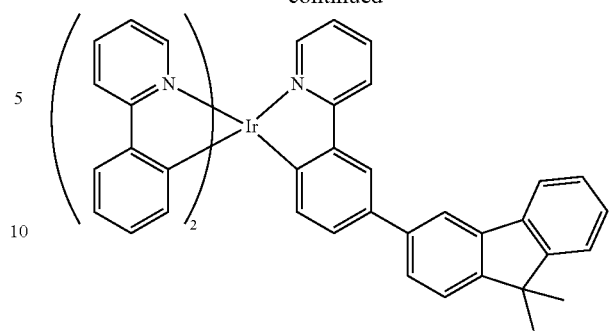
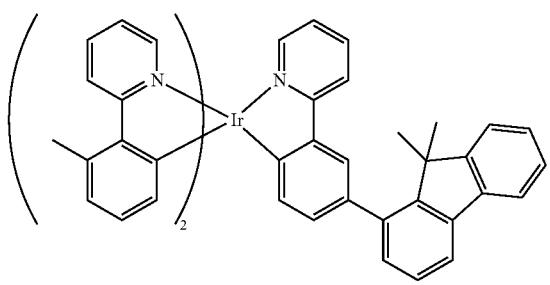
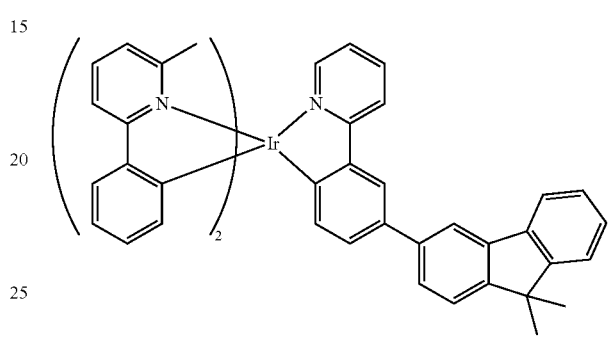
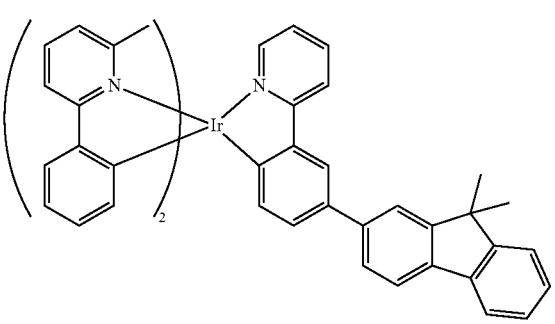
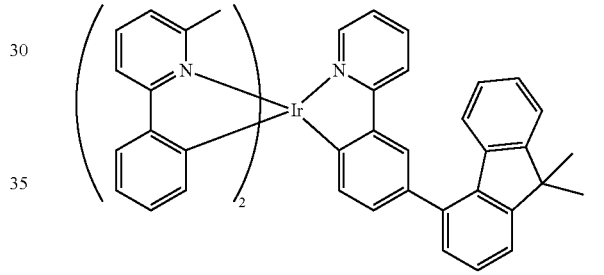
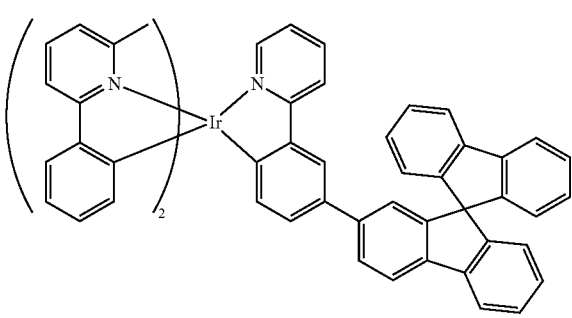
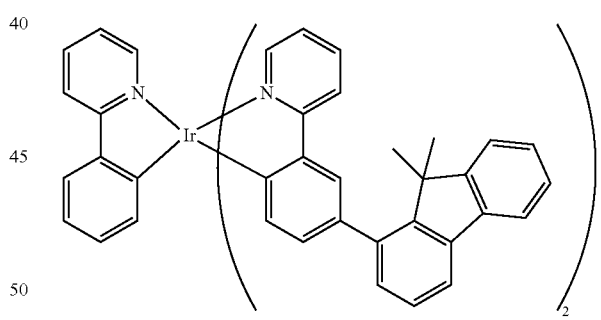
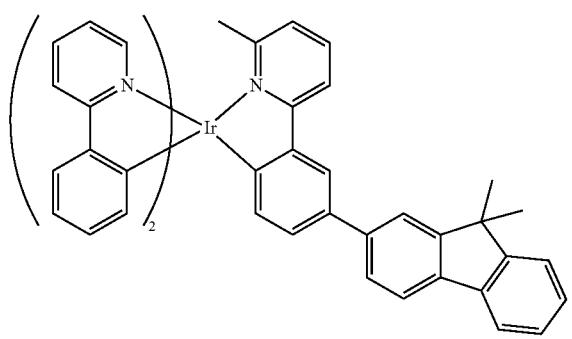
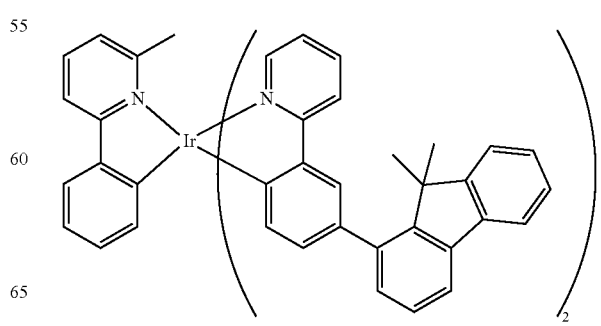

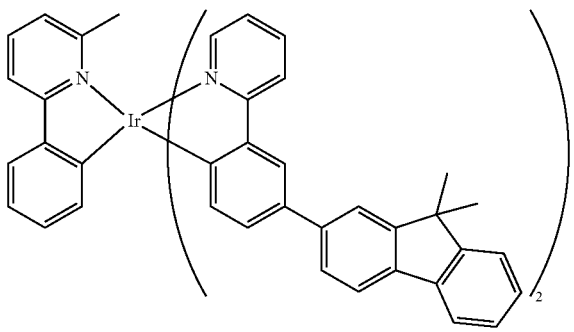
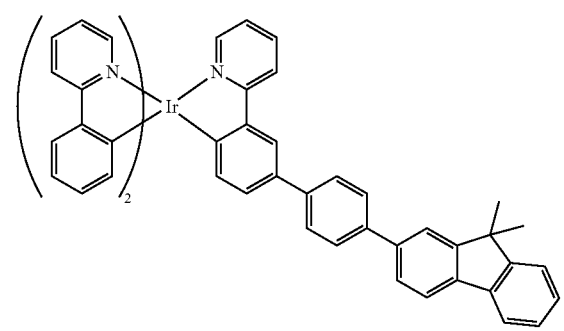
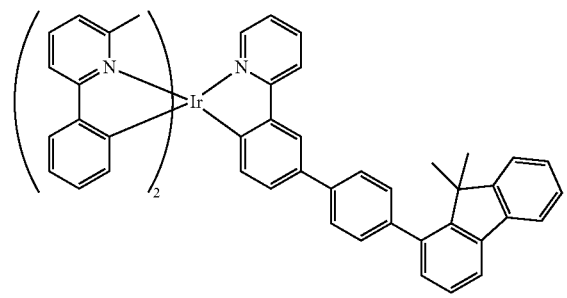
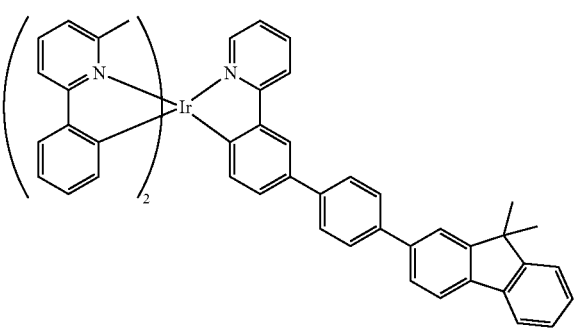
[Chem. 28]
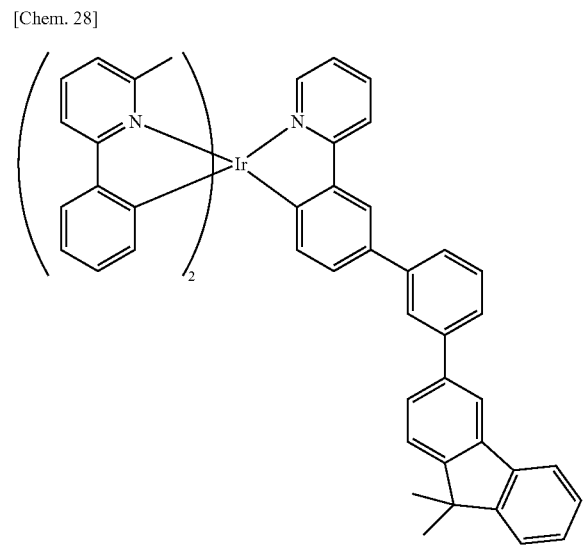
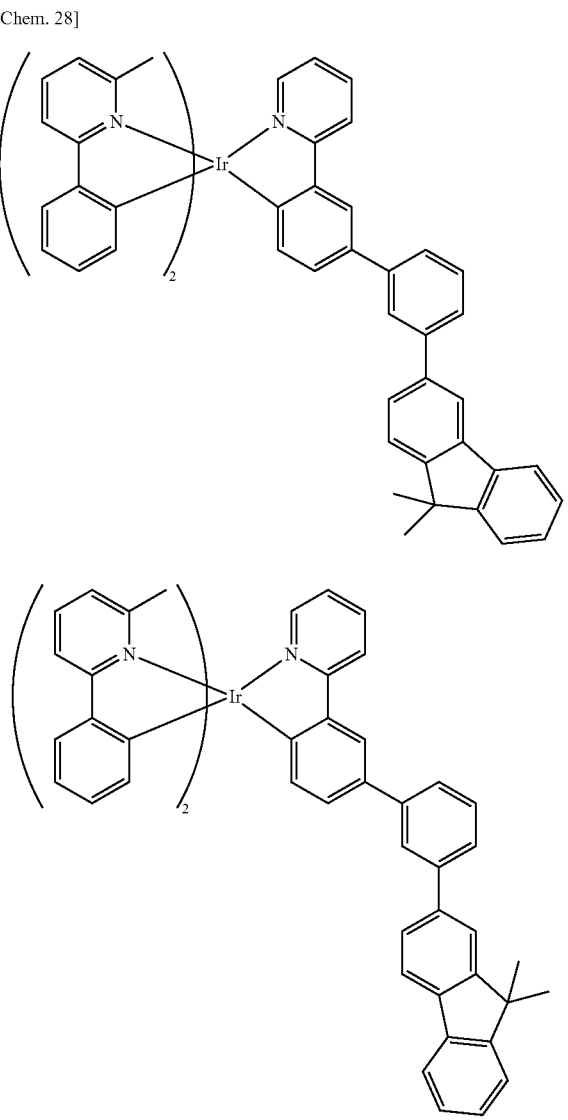
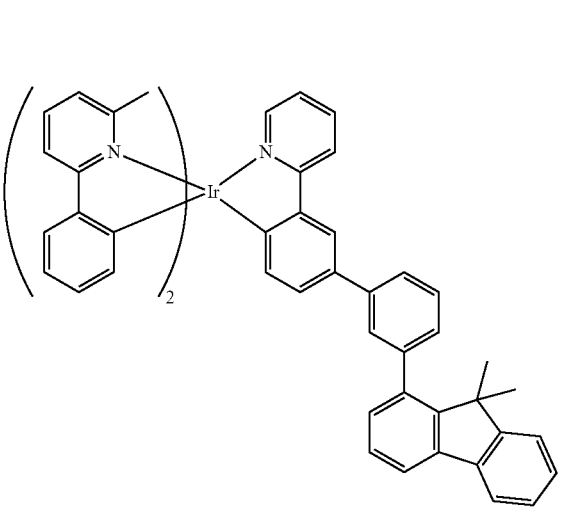

61
-continued
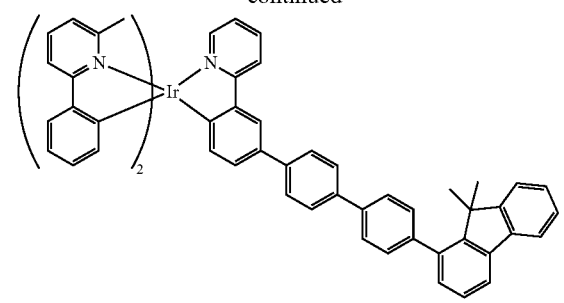
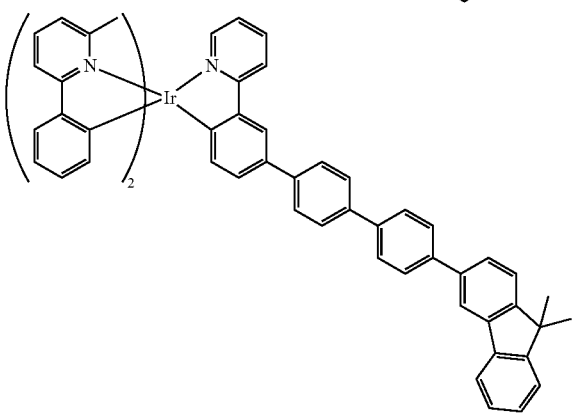
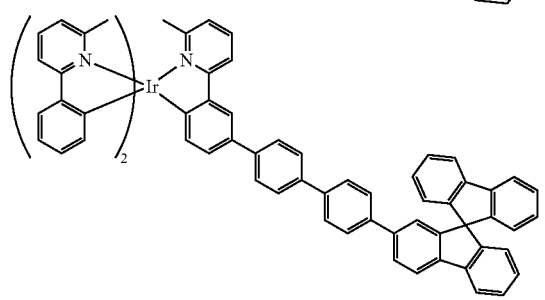
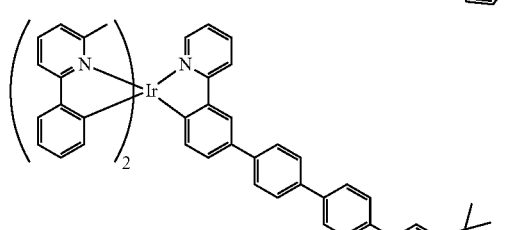
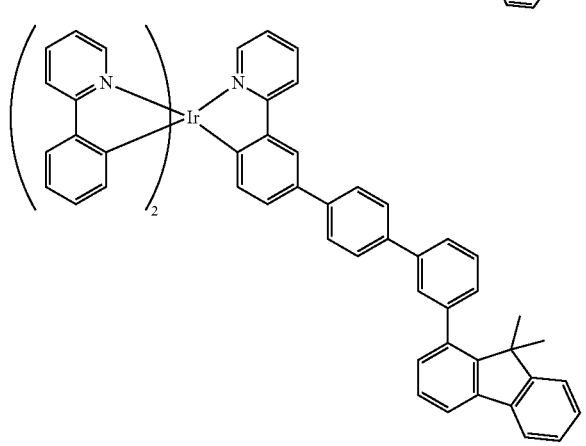
62
-continued
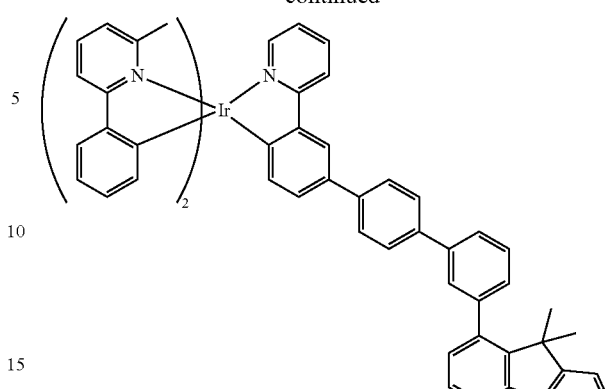
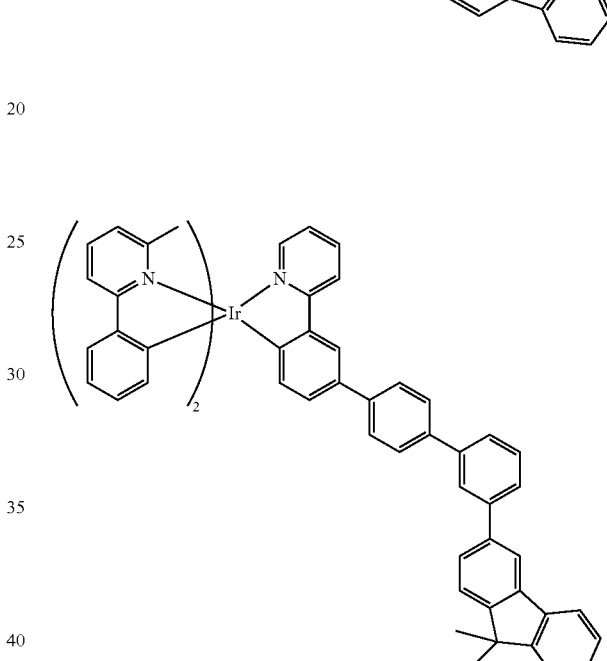
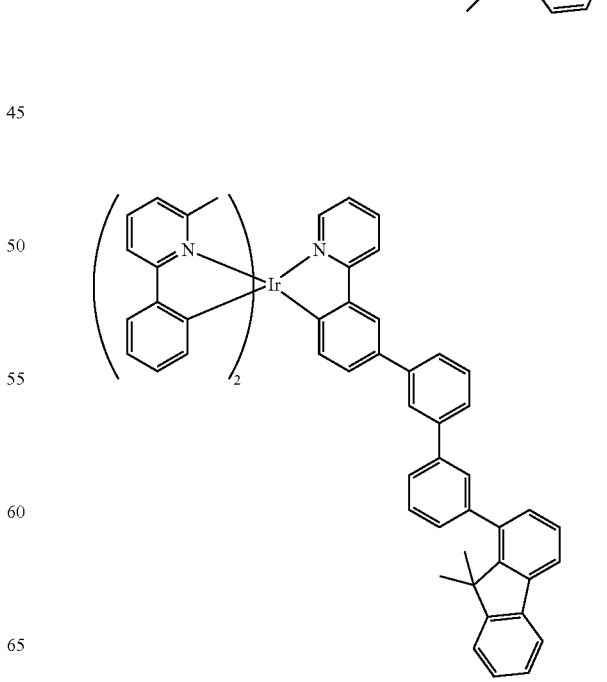

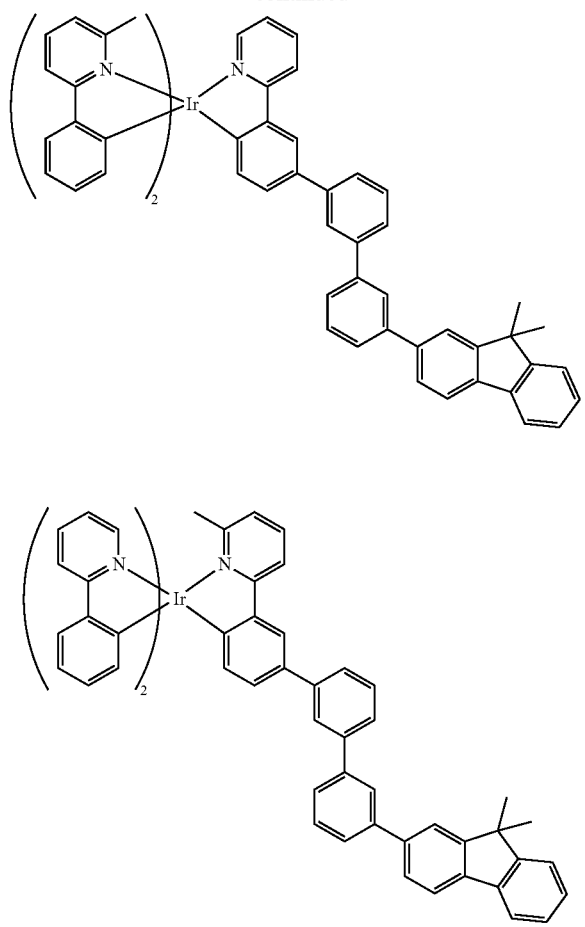
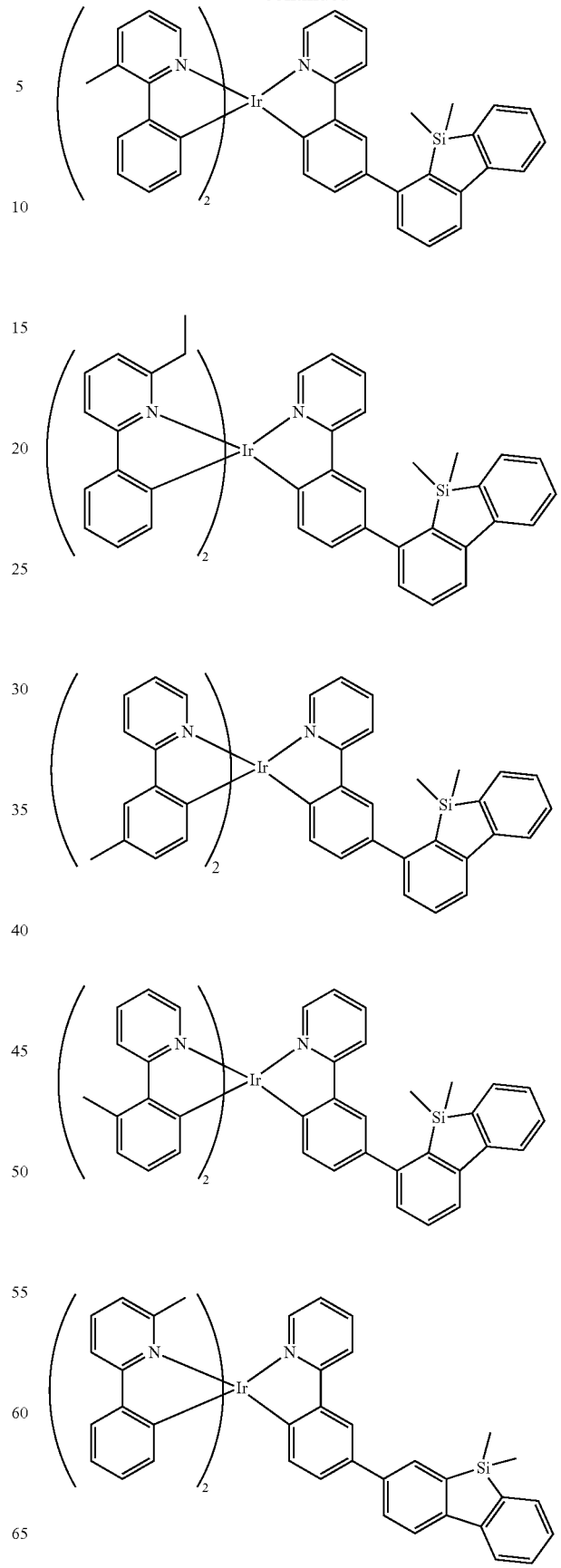

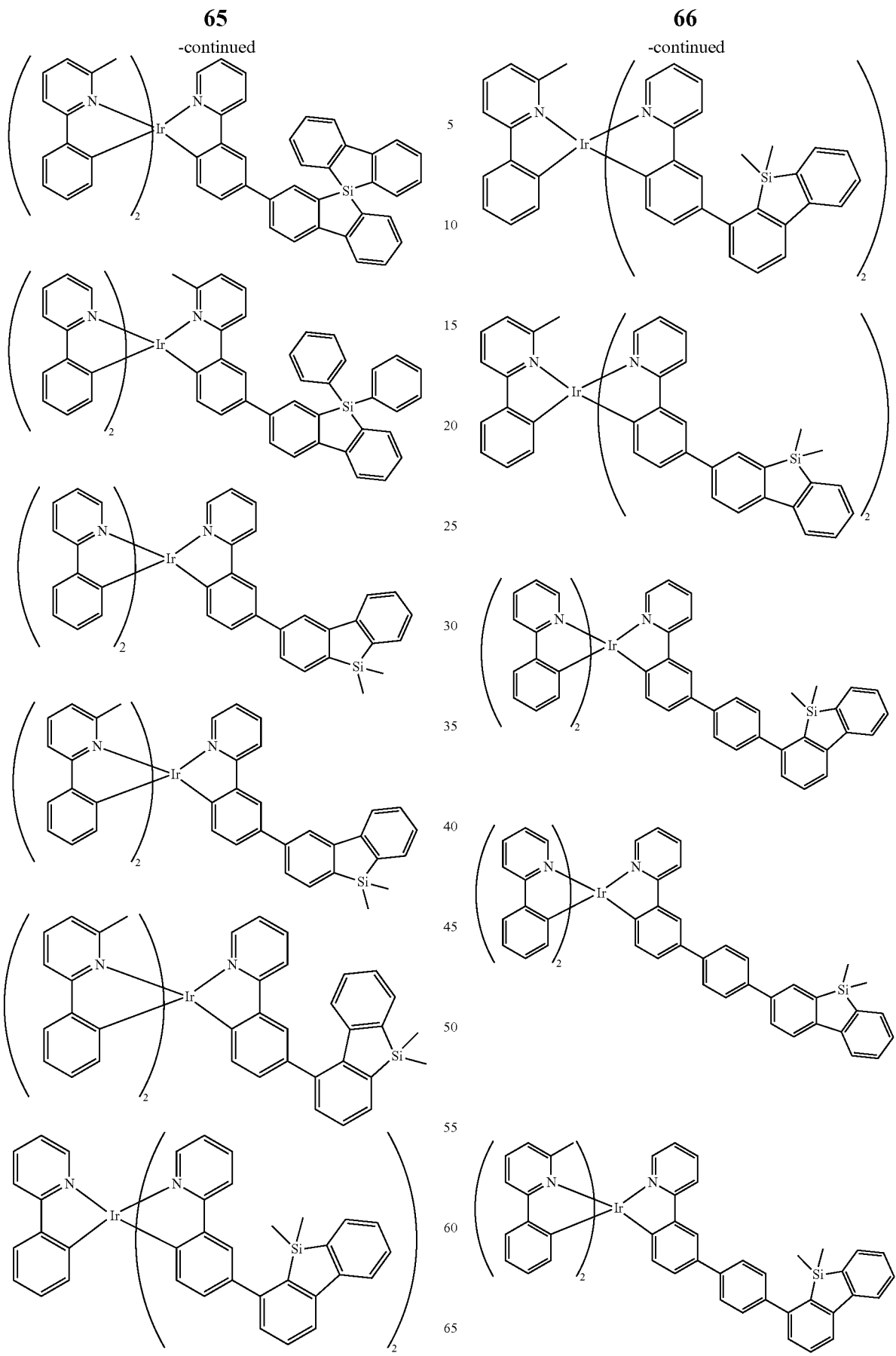

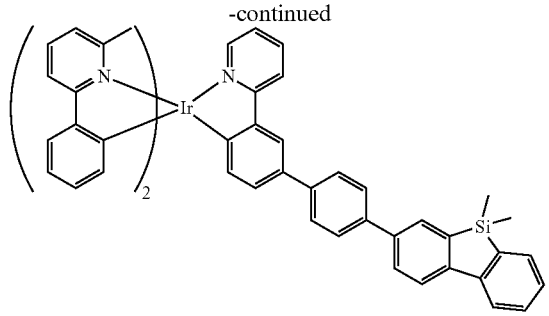
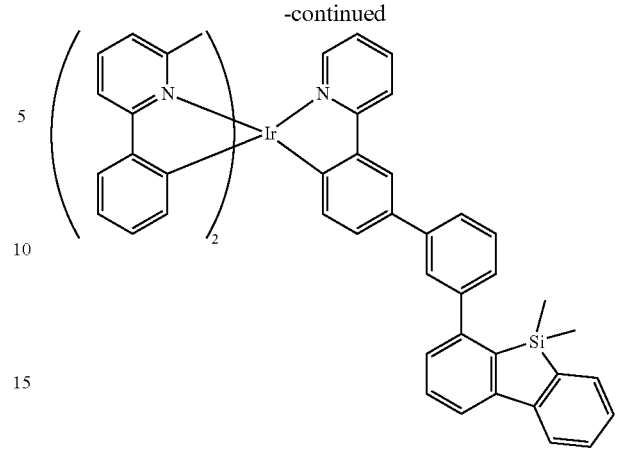
[Chem. 30]
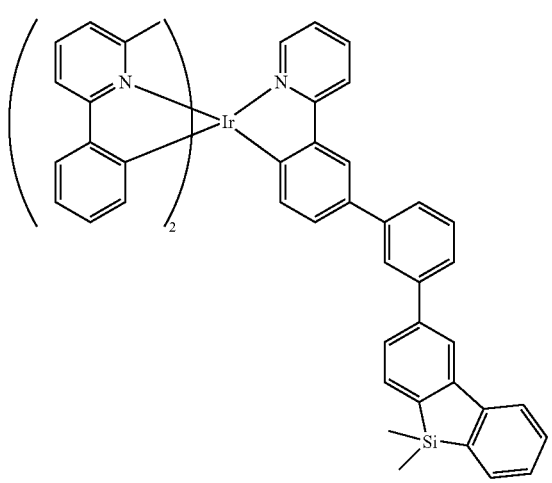
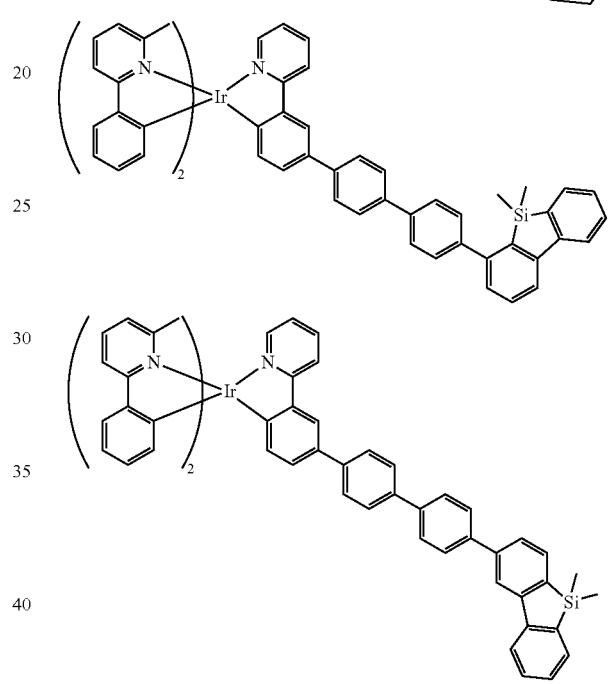
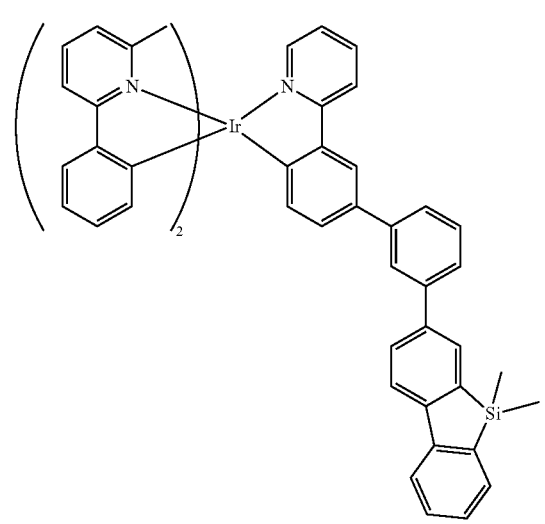
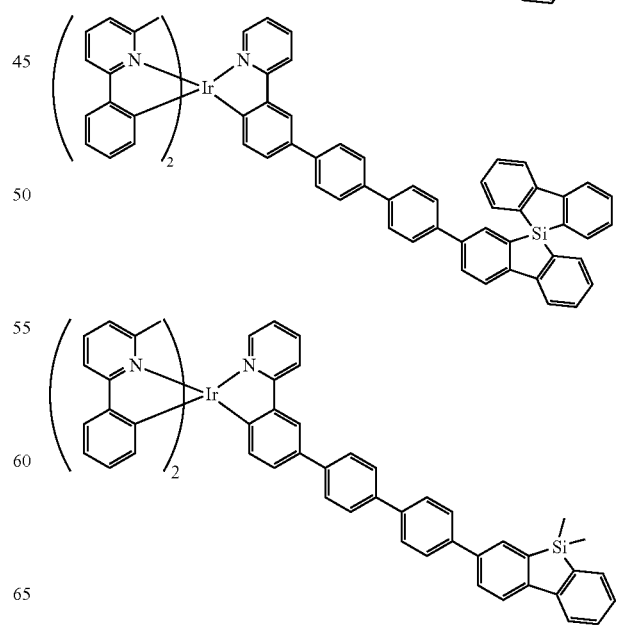

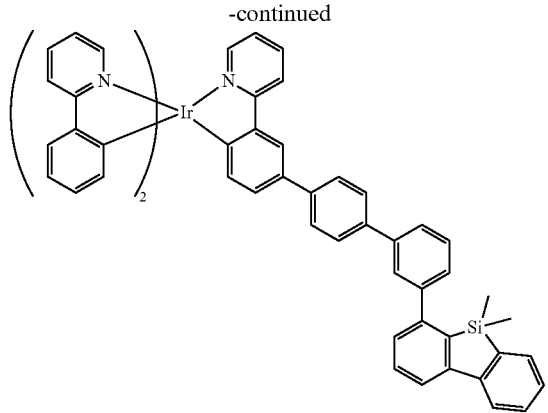
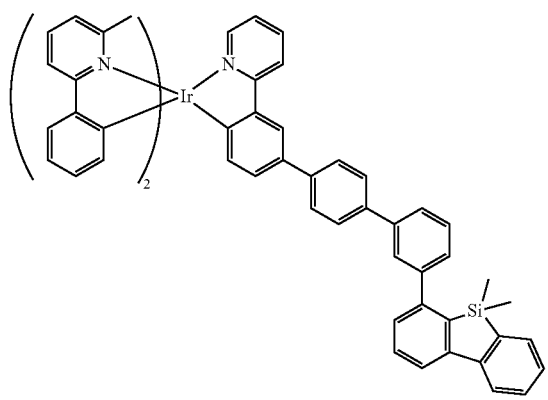
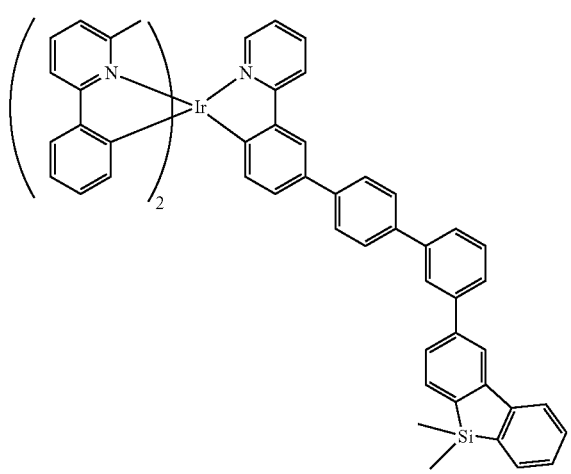
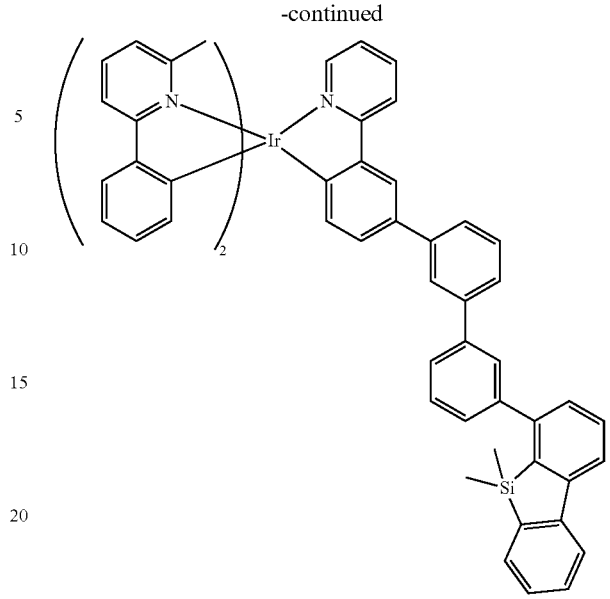
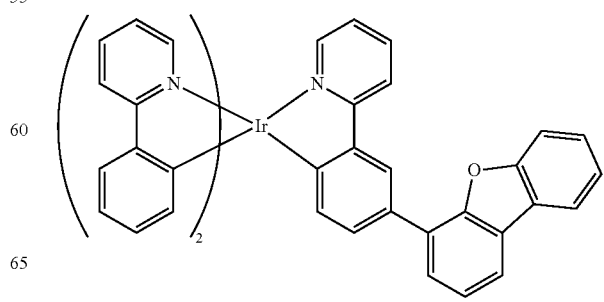
[Chem. 31]

71
-continued
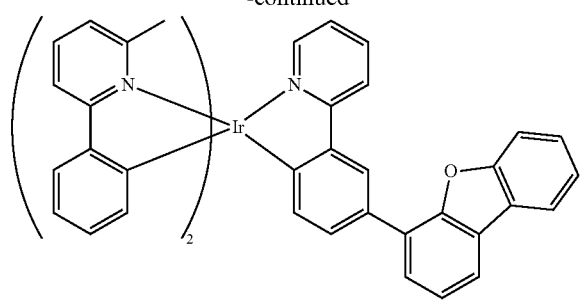
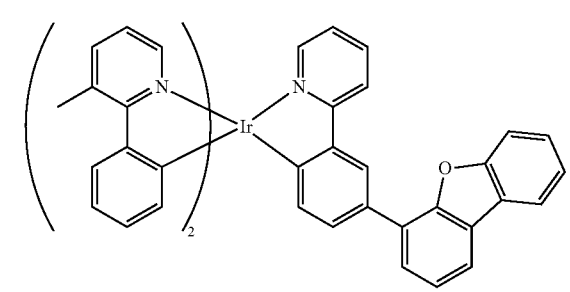
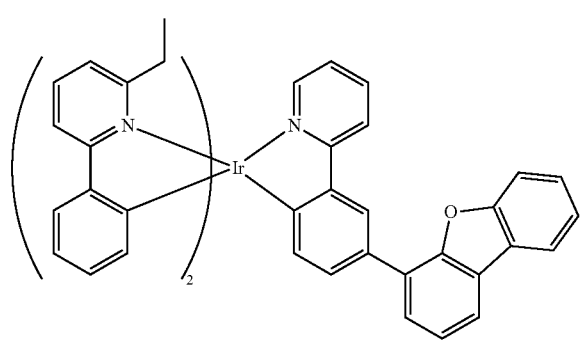
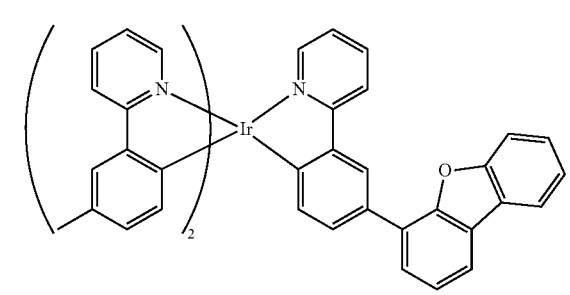
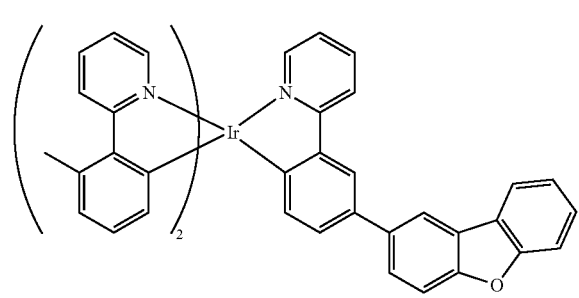
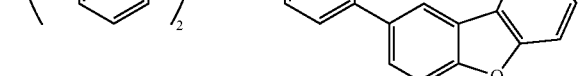
72
-continued
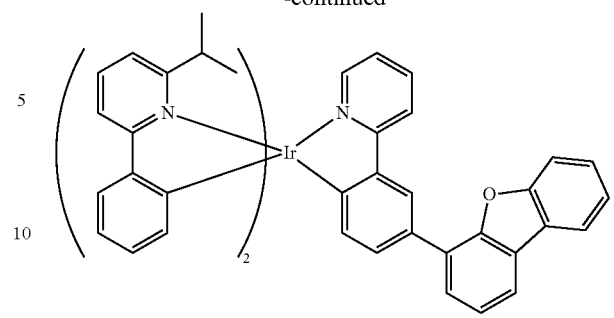
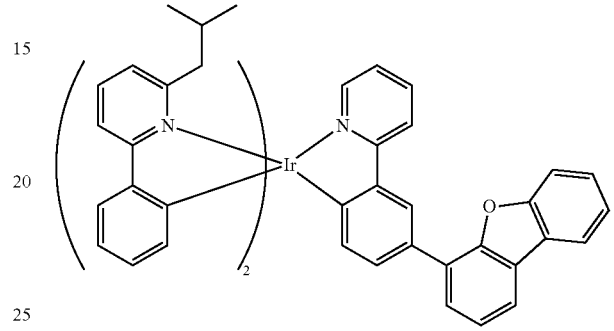
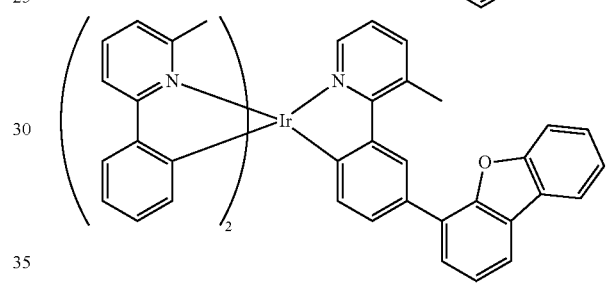
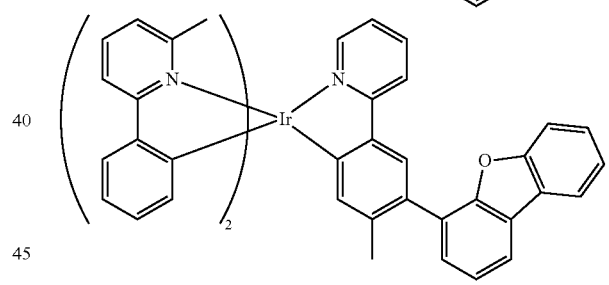
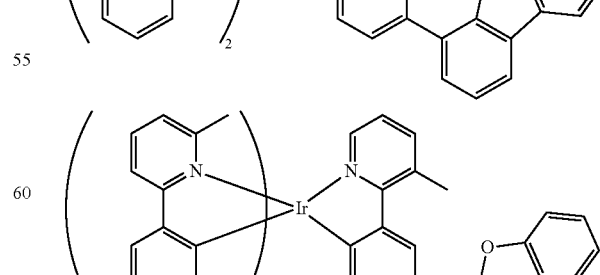
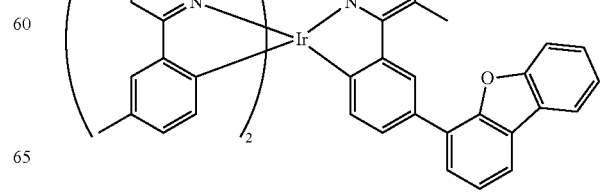

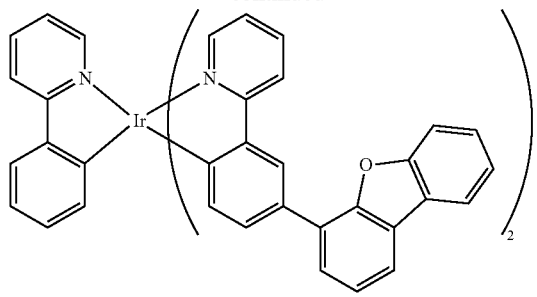
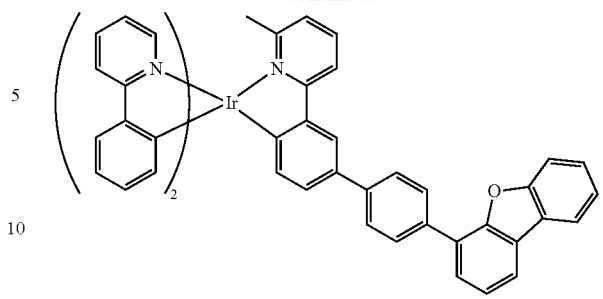
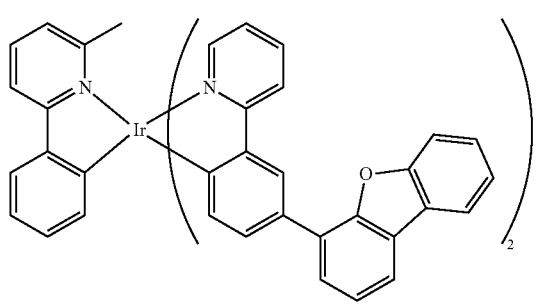
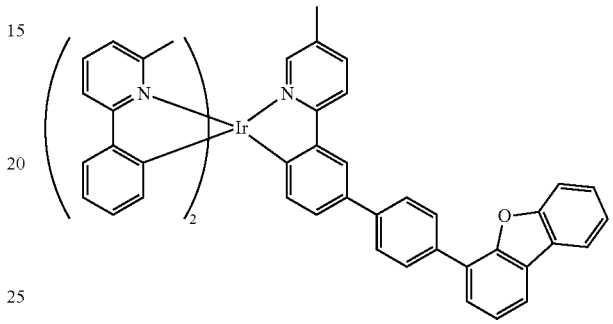
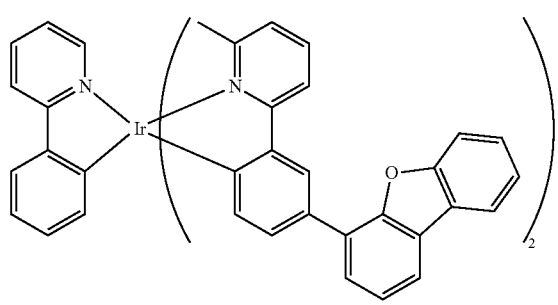
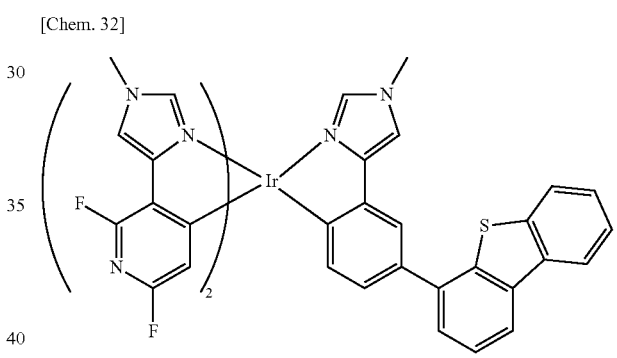
[Chem. 32]
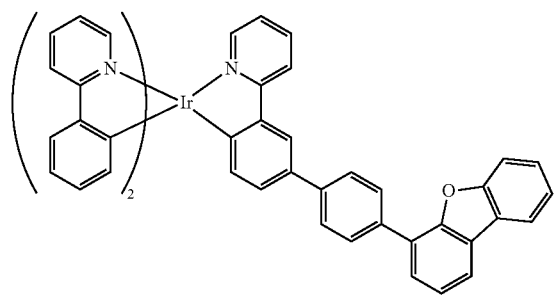
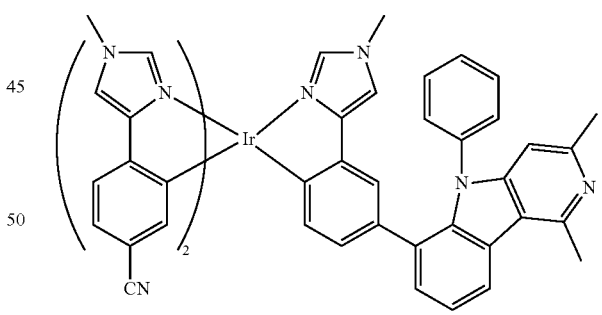
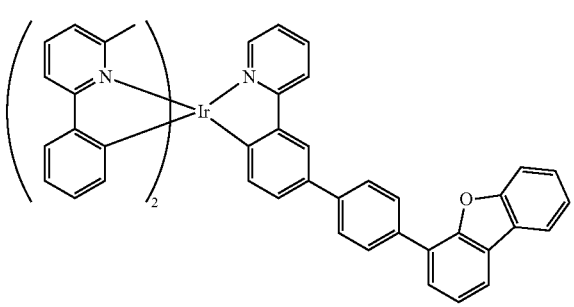
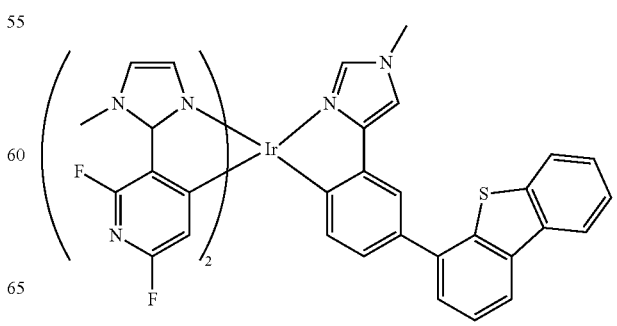

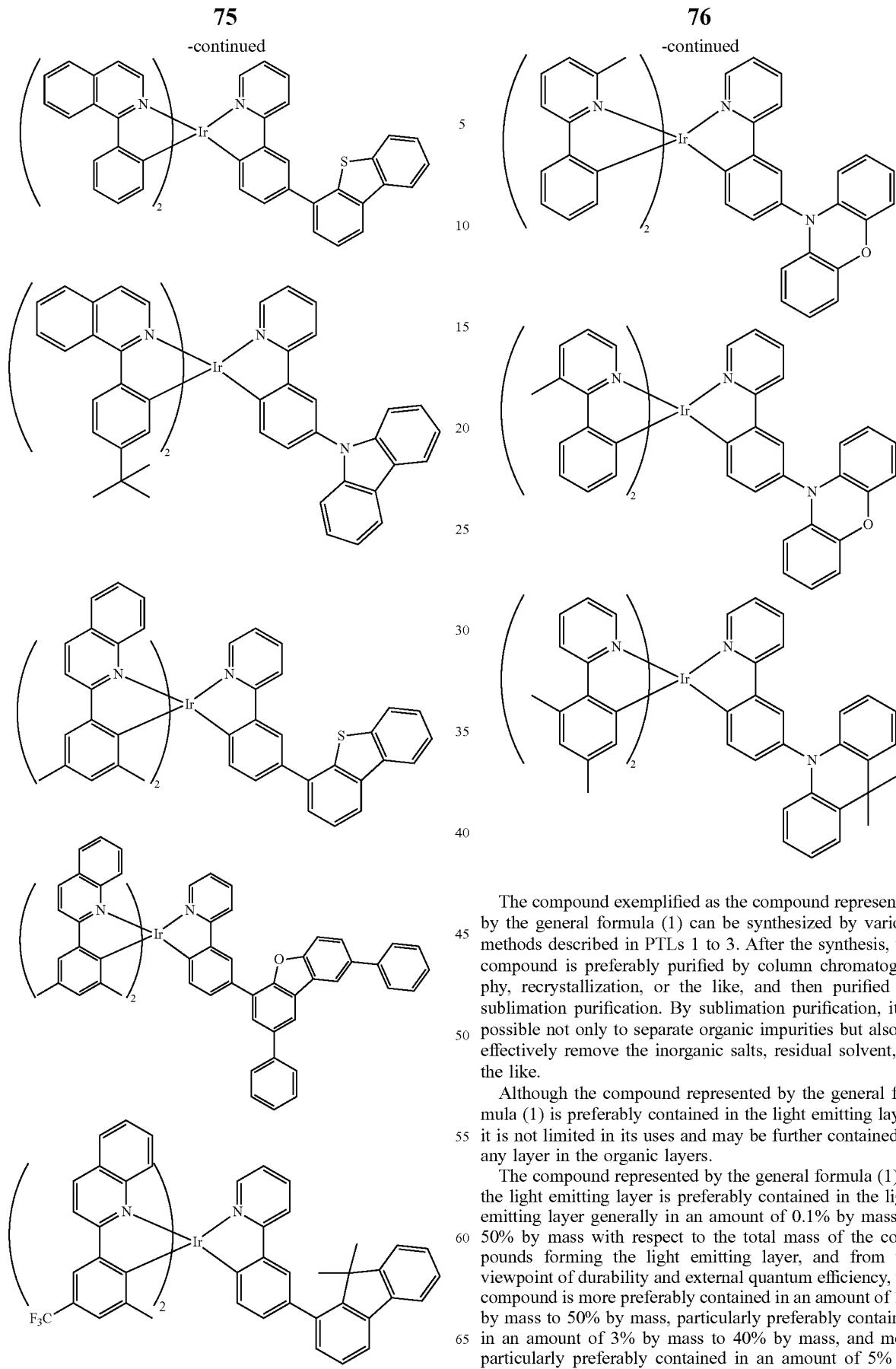

The compound exemplified as the compound represented by the general formula (1) can be synthesized by various methods described in PTLs 1 to 3. After the synthesis, the compound is preferably purified by column chromatography, recrystallization, or the like, and then purified by sublimation purification. By sublimation purification, it is possible not only to separate organic impurities but also to effectively remove the inorganic salts, residual solvent, or the like.

Although the compound represented by the general formula (1) is preferably contained in the light emitting layer, it is not limited in its uses and may be further contained in any layer in the organic layers.

The compound represented by the general formula (1) in the light emitting layer is preferably contained in the light emitting layer generally in an amount of 0.1% by mass to 50% by mass with respect to the total mass of the compounds forming the light emitting layer, and from the viewpoint of durability and external quantum efficiency, the compound is more preferably contained in an amount of 1% by mass to 50% by mass, particularly preferably contained in an amount of 3% by mass to 40% by mass, and more particularly preferably contained in an amount of 5% by mass to 20% by mass.

The compound represented by the general formula (1) of the present invention can be used preferably in electrophotography, organic transistors, organic opto-electric conversion elements (energy conversion applications, sensor applications, and the like), or organic electronics elements such as organic electroluminescent elements, and can be used particularly preferably in organic electroluminescent elements.

The compound of the present invention can be contained in a thin film containing the compound represented by the general formula (1). The thin film can be suitably formed by any of dry type film forming methods such as a deposition method and a sputtering method, and wet type film forming methods (solution coating methods) such as a transfer method, a printing method, a spin coating method, and a bar coating method, using the composition. The film thickness of the thin film may be any one chosen depending on the uses, but it is preferably from 0.1 nm to 1 nm, more preferably from 0.5 nm to 1 μm, still more preferably from 1 nm to 200 nm, and particularly preferably from 1 nm to 100 nm.

In the present invention, in the case where the compound represented by the general formula (1) is used as a green phosphorescent light emitting material, the maximum light emitting wavelength of the compound represented by the general formula (1) is preferably from 480 nm to 600 nm, more preferably from 490 nm to 550 nm, and still more preferably from 500 nm to 530 nm.

[Organic Electroluminescent Element]

The organic electroluminescent element of the present invention includes a substrate, a pair of electrodes including an anode and a cathode, disposed on the substrate, and at least one organic layer including a light emitting layer, disposed between the electrodes, in which at least one layer of the organic layer(s) contains a compound represented by the following general formula (1).

The configuration of the organic electroluminescent element of the present invention is not particularly limited. FIG. 1 shows an example of the configuration of the organic electroluminescent element of the present invention. An organic electroluminescent element 10 in FIG. 1 includes organic layers between a pair of electrodes (an anode 3 and a cathode 9) on a substrate 2.

The element configuration, the substrate, the anode, and the cathode of the organic electroluminescent element are described in detail, for example, in JP-A-2008-270736, and the matters described in the patent publication can be applied to the present invention.

Hereinafter, preferred aspects of the organic electroluminescent element of the present invention will be described in detail, in the order of the substrate, the electrode, the organic layer, the protective layer, the sealing enclosure, the driving method, the light emitting wavelength, and applications thereof.

<Substrate>

The organic electroluminescent element of the present invention has a substrate.

The substrate used in the present invention is preferably a substrate that does not scatter or attenuate light emitted from the organic layer. In the case of an organic material, those having excellent heat resistance, dimensional stability, solvent resistance, electrical insulating properties, and processability are preferred.

<Electrodes>

The organic electroluminescent element of the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be typically one having a function as an electrode of supplying holes into an organic layer, and is not particularly limited in its shape, structure, size, or the like. Further, depending on the use and purpose of the light emitting element, the anode can be suitably selected from the known electrode materials. As described above, the anode is usually provided as a transparent anode.

(Cathode)

The cathode may be typically one having a function as an electrode of injecting electrons to an organic layer, and is not particularly limited in its shape, structure, size, or the like. Further, depending on the use and purpose of the light emitting element, the cathode can be suitably selected from the known electrode materials.

<Organic Layer>

The organic electroluminescent element of the present invention includes the organic layer(s) disposed between the electrodes, and the organic layer(s) preferably contains the compound represented by the general formula (1) as a phosphorescent light emitting material.

The organic layer is not particularly limited and can be suitably selected depending on the use and purpose of the organic electroluminescent element. However, the organic layer is preferably formed on the transparent electrode or the semi-transparent electrode. In that case, the organic layer is formed on the entire surface or one surface of the transparent electrode or the semi-transparent electrode.

The shape, the size, the thickness, and the like of the organic layer are not particularly limited and can be suitably selected depending on the purpose.

Hereinafter, the configuration of the organic layer, the method for forming an organic layer, preferred aspects of the respective layers constituting the organic layer, and the materials used in the respective layers in the organic electroluminescent element of the present invention will be described in order.

(Configuration of Organic Layers)

In the organic electroluminescent element of the present invention, the organic layer preferably includes a charge transporting layer. The charge transporting layer refers to a layer in which charges move when voltage is applied to the organic electroluminescent element. Specifically, examples thereof include a hole injecting layer, a hole transporting layer, an electron blocking layer, a light emitting layer, a hole blocking layer, an electron transporting layer, and an electron injecting layer.

The organic electroluminescent element of the present invention has a light emitting layer including the phosphorescent light emitting material and other organic layers, and the light emitting layer preferably contains the compound represented by the general formula (1) as the phosphorescent light emitting material. Furthermore, in the organic electroluminescent element of the present invention, the organic layer preferably a light emitting layer including the phosphorescent light emitting material and other organic layer. However, for the organic electroluminescent element of the present invention, even in the case where the organic layer has a light emitting layer and other organic layers, the layers are not necessarily distinct from each other.

The compound represented by the general formula (1) may be contained in any of the organic layers between a cathode and an anode of the organic electroluminescent element.

Examples of the organic layer which may contain the compound represented by the general formula (1) include a light emitting layer, a hole injecting layer, a hole transporting layer, an electron transporting layer, an electron injecting layer, an exciton blocking layer, and a charge blocking layer (a hole blocking layer, an electron blocking layer, and the like), preferably any one of a light emitting layer and a hole injecting layer, more preferably a light emitting layer.

Furthermore, the hole injecting layer is preferably contained between the pair of electrodes, and the compound represented by the general formula (1) is preferably contained in the hole injecting layer.

In the compound represented by the general formula (1) is contained in the organic layer other than the light emitting layer, the compound is preferably contained in the amount of 70% by mass to 100% by mass, and more preferably 85% by mass to 100% by mass, with respect to the total mass of the organic layer.

For such the organic layers, each of a plurality of layers may be provided, and in the case of providing the plurality of layers, the layers may be formed of the same materials or of different materials from each other in each layers.

(Method for Forming Organic Layers)

Each of the organic layers in the organic electroluminescent element of the present invention can be suitably formed by any of dry type film forming methods such as a deposition method and a sputtering method, and wet type film forming methods (solution coating methods) such as a transfer method, a printing method, a spin coating method, and a bar coating method.

In the organic electroluminescent element of the present invention, the organic layer(s) disposed between the pair of electrodes is preferably formed by deposition of a composition containing the compound represented by the general formula (1) in at least one layer.

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism. The light emitting layer in the organic electroluminescent element of the present invention preferably contains at least one kind of phosphorescent light emitting material.

The light emitting layer in the organic electroluminescent element of the present invention may be constituted of only the light emitting material, or may be constituted as a mixed layer of a host material and the light emitting material. The light emitting material may be made of one kind or two or more kinds thereof. The host material is preferably a charge transporting material. The host material may be made of one kind or two or more kinds thereof. Examples thereof include a configuration in which an electron transporting host material and a hole transporting host material are mixed. Further, the light emitting layer may include a material which does not have charge transporting properties and does not emit light.

In addition, the light emitting layer may be made of a single layer or multiple layers of two or more layers. Each of the layers may include the same light emitting material or host material, and may also include a different material in every layer. In the case where a plurality of light emitting layers are present, each of the light emitting layers may emit light in a different luminous color from each other.

The thickness of the light emitting layer is not particularly limited, but it is preferably from 2 nm to 500 nm, and above all, from the viewpoint of external quantum efficiency, it is more preferably from 3 nm to 200 nm, and still more preferably from 5 nm to 100 nm.

For the organic electroluminescent element of the present invention, in a preferred aspect, the light emitting layer contains the compound represented by the general formula (1), and in a more preferred aspect, the compound represented by the general formula (1) is used as the light emitting material of the light emitting layer. Here, in the present specification, the guest material is a compound which emits light in the case where two or more kinds of compounds are contained in the light emitting layer. The statement "which emits light" means that the amount of light emission from the light emitting material is preferably 95% or more, more preferably 97% or more, and still more preferably 99% or more, with respect to the total amount of light emission in the entirety of the element.

Hereinafter, the host material will be described as a material other than the light emitting material of the light emitting layer. The host material is a compound which usually plays a role in injecting or transporting charges in the light emitting layer and is also a compound which does not substantially emit light in itself. As used herein, the statement "which does not substantially emit light" means that the amount of light emission from the compound which does not substantially emit light is preferably 5% or less, more preferably 3% or less, and still more preferably 1% or less, with respect to the total amount of light emission in the entirety of the element.

Examples of the host material which can be used in the organic electroluminescent element of the present invention include the following compounds:

conductive high-molecular oligomers such as pyrrole, indole, carbazole, azaindole, indolocarbazole, azacarbazole, triazole, oxazole, oxadiazole, pyrazole, imidazole, thiophene, benzothiophene, dibenzothiophene, furan, benzofuran, dibenzofuran, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin-based compounds, aromatic hydrocarbon compounds with fused rings (fluorene, naphthalene, phenanthrene, triphenylene, and the like), polysilane-based compounds, poly(N-vinylcarbazole), aniline-based copolymers, thiophene oligomers, and polythiophene, organic silanes, carbon films, pyridine, pyrimidine, triazine, fluorenone, anthraquinodimethane, anthrone, diphenylquinone, thiopyran dioxide, carbodiimide, fluorenylidenemethane, distyrylpyrazine, fluorine-substituted aromatic compounds, hetero ring tetracarboxylic anhydrides such as naphthalene perylene, a variety of metal complexes typified by metal complexes of phthalocyanine and 8-quinolinol derivatives and metal complexes having metal phthalocyanine, benzoxazole, or benzothiazole as a ligand thereof, and derivatives thereof (which may have a substituent or a fused ring).

Among these, carbazole, dibenzothiophene, dibenzofuran, arylamine, aromatic hydrocarbon compounds with fused rings, metal complexes, and derivatives thereof are particularly preferred, and derivatives of carbazole, derivatives of dibenzothiophene, and derivatives of aromatic hydrocarbon compounds with fused rings are more particularly preferred. As the derivatives of the aromatic hydrocarbon compounds with fused rings, derivatives of naphthalene-based compounds, anthracene-based compounds, phenanthrene-based compounds, triphenylene-based compounds, and pyrene-based compounds are preferred; derivatives of anthracene-based compounds, pyrene-based compounds, and triphenylene-based compounds are more preferred; and derivatives of triphenylene-based compounds are particularly preferred. As the derivatives of dibenzothiophene, the compounds described in WO2009/085344 are preferred, and as the derivatives of the triphenylene-based compounds, a compound represented by the following general formula (TpH-1) is preferred.

General Formula (TpH-1)

[Chem. 33]

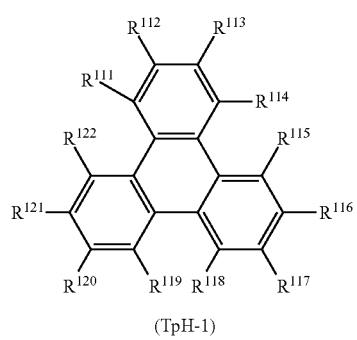

(TpH-1)

In the general formula (TpH-1), $R^{111}$ to $R^{122}$ each independently represent a hydrogen atom, an alkyl group, a phenyl group, a heteroaryl group, a fluorenyl group, a naphthyl group, a dibenzofuranyl group, a dibenzothiophenyl group, a carbazolyl group, or a triphenylenyl group (these may be further substituted with an alkyl group, a phenyl group, a heteroaryl group, a fluorenyl group, a naphthyl group, a dibenzofuranyl group, a dibenzothiophenyl group, a carbazolyl group, or a triphenylenyl group). However, there is no case where all of $R^{111}$ to $R^{122}$ are hydrogen atoms.

Examples of the alkyl group represented by $R^{111}$ to $R^{122}$ include a methyl group, an ethyl group, an isopropyl group, an n-butyl group, a tert-butyl group, an n-octyl group, an n-decyl group, an n-hexadecyl group, a cyclopropyl group, a cyclopentyl group, and a cyclohexyl group, preferably a methyl group, an ethyl group, an isopropyl group, a tert-butyl group, and a cyclohexyl group, and more preferably a methyl group, an ethyl group, and a tert-butyl group, each of which may be substituted or unsubstituted.

As $R^{111}$ to $R^{122}$, a hydrogen atom, an alkyl group having 1 to 4 carbon atoms, a phenyl group, a heteroaryl group, a fluorenyl group, a naphthyl group, a dibenzofuranyl group, a dibenzothiophenyl group, a carbazolyl group, or a triphenylenyl group (these substituents may be further substituted with an alkyl group, a phenyl group, a heteroaryl group, a fluorenyl group, a naphthyl group, a dibenzofuranyl group, a dibenzothiophenyl group, a carbazolyl group, or a triphenylenyl group) is preferred, and a hydrogen atom or a phenyl group (the phenyl group may be substituted with an alkyl group, a phenyl group, a heteroaryl group, a fluorenyl group, a naphthyl group, a dibenzofuranyl group, a dibenzothiophenyl group, a carbazolyl group, or a triphenylenyl group). There is no case where all of $R^{111}$ to $R^{122}$ are hydrogen atoms.

The total number of the aryl rings or heteroaryl rings in the general formula (TpH-1) is preferably from 2 to 10, and more preferably from 3 to 5. Within these ranges, an amorphous thin film with good quality can be formed, and the solubility in a solvent, and the sublimation and deposition suitability are improved.

$R^{111}$ to $R^{122}$ each independently have a total number of carbon atoms of preferably 20 to 50, and more preferably 20 to 36. Within these ranges, an amorphous thin film with good quality can be formed, and the solubility in a solvent, and the sublimation and deposition suitability are improved.

The compound represented by the general formula (TpH-1) is preferably a compound represented by the following general formula (TpH-2).

[Chem. 34]

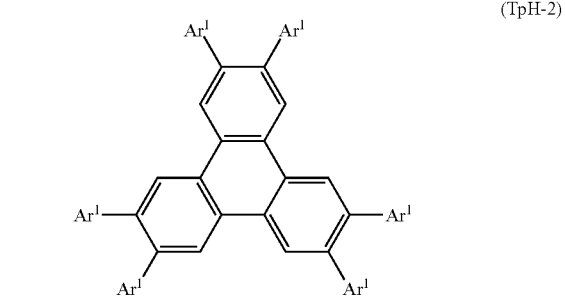

(TpH-2)

In the general formula (TpH-2), a plurality of $Ar^1$s are the same as each other, and each represent an alkyl group, a phenyl group, a heteroaryl group, a fluorenyl group, a naphthyl group, a dibenzofuranyl group, a dibenzothiophenyl group, a carbazolyl group, or a triphenylenyl group (these may be further substituted with an alkyl group, a phenyl group, a heteroaryl group, a fluorenyl group, a naphthyl group, a dibenzofuranyl group, a dibenzothiophenyl group, a carbazolyl group, or a triphenylenyl group).

The alkyl group, the phenyl group, the heteroaryl group, the fluorenyl group, the naphthyl group, the dibenzofuranyl group, the dibenzothiophenyl group, the carbazolyl group, or the triphenylenyl group (these may be further substituted with an alkyl group, a phenyl group, a heteroaryl group, a fluorenyl group, a naphthyl group, a dibenzofuranyl group, a dibenzothiophenyl group, a carbazolyl group, or a triphenylenyl group) represented by $Ar^1$ has the same definitions as for $R^{112}$ to $R^{123}$, and the preferred ones are also the same.

The compound represented by the general formula (TpH-1) is preferably a compound represented by the following general formula (TpH-3).

[Chem. 35]

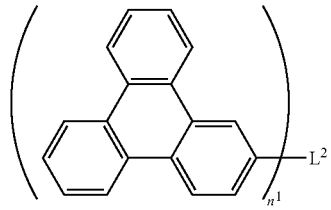

(TpH-3)

In the general formula (TpH-3), $L^2$ represents an alkyl group, a phenyl group, a heteroaryl group, a fluorenyl group, a naphthyl group, a dibenzofuranyl group, a dibenzothiophenyl group, a carbazolyl group, or a triphenylenyl group (these may be further substituted with an alkyl group, a phenyl group, a heteroaryl group, a fluorenyl group, a naphthyl group, a dibenzofuranyl group, a dibenzothiophenyl group, a carbazolyl group, or a triphenylenyl group), or an $n^1$-valent linking group formed by a combination of these groups. $n^1$ represents an integer of 2 to 6.

An alkyl group, a phenyl group, a heteroaryl group, a fluorenyl group, a naphthyl group, a dibenzofuranyl group, a dibenzothiophenyl group, a carbazolyl group, or a triphenylenyl group (these may be further substituted with an alkyl group, a phenyl group, a heteroaryl group, a fluorenyl group, a naphthyl group, a dibenzofuranyl group, a dibenzothiophenyl group, a carbazolyl group, or a triphenylenyl group), which forms the n-valent linking group represented by $L^2$, has the same definitions as for $R^{112}$ to $R^{123}$.

$L^2$ is preferably an $n^1$-valent linking group formed of a benzene ring, a fluorene ring, or a group formed by a combination of these groups, each of which may be substituted with an alkyl group or a benzene ring.

Preferred specific examples of $L^2$ are listed below, but $L^2$ is not limited thereto, provided that the groups are bonded to a triphenylene ring at a position of * in the specific examples.

[Chem. 36]

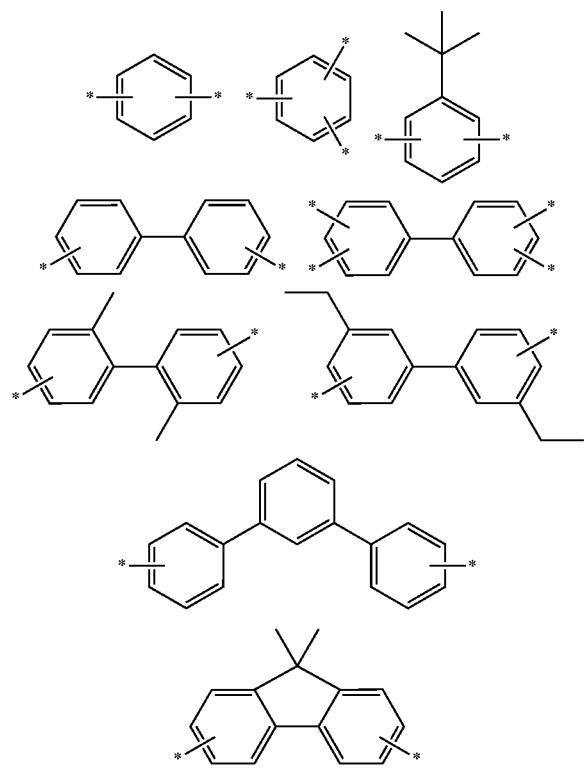

n is preferably from 2 to 5, and more preferably from 2 to 4.

The compound represented by the general formula (TpH-1) is preferably a compound represented by the following general formula (TpH-4).

[Chem. 37]

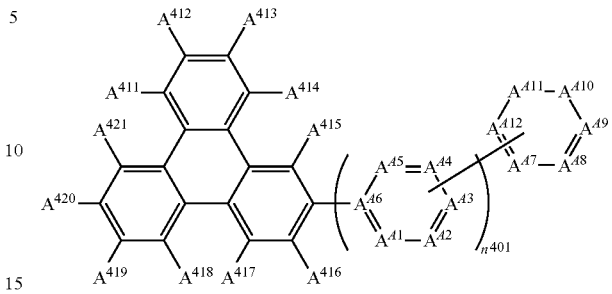

General Formula (TpH-4)

(In the general formula (TpH-4), $A^{41}$ to $A^{412}$ each independently represent $CR^{400}$ or a nitrogen atom. $n^{401}$ represents an integer of 0 to 8. In the case where $n^{401}$ is 0, the ring represented by $A^{41}$ to $A^{46}$ represents a single bond between a triphenylene ring and a ring represented by $A^{47}$ to $A^{412}$. In the case where $n^{401}$ is from 2 to 6, the rings represented by a plurality of $A^{41}$ to $A^{46}$ may be different from each other at each occurrence, and the binding modes among a plurality of the rings may be different from each other at each occurrence.)

Further, in the present invention, the hydrogen atom in the description of the general formula (TpH-4) also includes isotopes (a deuterium atom and the like), and the atoms additionally constituting the substituent are also intended to include isotopes of the atoms.

In the general formula (TpH-4), $R^{411}$ to $R^{421}$ each independently represent a hydrogen atom, an alkyl group, a phenyl group, a heteroaryl group, a fluorenyl group, a naphthyl group, a dibenzofuranyl group, a dibenzothiophenyl group, a carbazolyl group, or a triphenylenyl group (these may be further substituted with an alkyl group, a phenyl group, a heteroaryl group, a fluorenyl group, a naphthyl group, a dibenzofuranyl group, a dibenzothiophenyl group, a carbazolyl group, or a triphenylenyl group).

$R^{411}$ to $R^{421}$ are each preferably a hydrogen atom, an alkyl group having 1 to 4 carbon atoms, a phenyl group, a heteroaryl group, a fluorenyl group, a naphthyl group, a dibenzofuranyl group, a dibenzothiophenyl group, a carbazolyl group, or a triphenylenyl group (these substituents may be further substituted with an alkyl group, a phenyl group, a heteroaryl group, a fluorenyl group, a naphthyl group, a dibenzofuranyl group, a dibenzothiophenyl group, a carbazolyl group, or a triphenylenyl group), more preferably a hydrogen atom, a phenyl group (the phenyl group may be substituted with an alkyl group, a phenyl group, a heteroaryl group, a fluorenyl group, a naphthyl group, a dibenzofuranyl group, a dibenzothiophenyl group, a carbazolyl group, or a triphenylenyl group), and particularly preferably a hydrogen atom.

$A^{41}$ to $A^{412}$ are preferably $CR^{400}$.

In general formula (TpH-4), examples of the substituent represented by $R^{400}$ include a hydrogen atom, an alkyl group having 1 to 4 carbon atoms, a phenyl group, a heteroaryl group, a fluorenyl group, a naphthyl group, a dibenzofuranyl group, a dibenzothiophenyl group, a carbazolyl group, or a triphenylenyl group (these substituents may be further substituted with an alkyl group, a phenyl group, a heteroaryl group, a fluorenyl group, a naphthyl group, a dibenzofuranyl group, a dibenzothiophenyl group, a carbazolyl group, or a triphenylenyl group). A plurality of $R^{400}$s may be different from each other.

$R^{400}$ is preferably a hydrogen atom, an alkyl group having 1 to 4 carbon atoms, a phenyl group, a heteroaryl group, a fluorenyl group, a naphthyl group, a dibenzofuranyl group, a dibenzothiophenyl group, a carbazolyl group, or a triphenylenyl group (these substituents may be further substituted with an alkyl group, a phenyl group, a heteroaryl group, a fluorenyl group, a naphthyl group, a dibenzofuranyl group, a dibenzothiophenyl group, a carbazolyl group, or a triphenylenyl group), more preferably a hydrogen atom, an alkyl group having 1 to 4 carbon atoms, a phenyl group (the phenyl group may be substituted with an alkyl group, a phenyl group, a heteroaryl group, a fluorenyl group, a naphthyl group, a dibenzofuranyl group, a dibenzothiophenyl group, a carbazolyl group, or a triphenylenyl group), a dibenzofuranyl group, or a dibenzothiophenyl group, and particularly preferably a hydrogen atom, an alkyl group having 1 to 4 carbon atoms, a phenyl group (the phenyl group may be substituted with alkyl group, a phenyl group, a heteroaryl group, a fluorenyl group, a naphthyl group, a dibenzofuranyl group, a dibenzothiophenyl group, a carbazolyl group, or a triphenylenyl group).

$n^{401}$ is preferably an integer of 0 to 5, more preferably an integer of 1 to 5, and particularly preferably an integer of 2 to 4.

$n^{401}$ is an integer of 1 or more, and in the case where the position bonded to a ring represented by $A^{47}$ to $A^{412}$ is $A^{43}$, from the viewpoint of luminous efficiency, the substituents represented by $A^{44}$ or $A^{45}$ are each $CR^{400}$, and $R^{400}$ is preferably an alkyl group having 1 to 4 carbon atoms or a phenyl group, more preferably an alkyl group having 1 to 4 carbon atoms, and particularly preferably a methyl group.

In the general formula (TpH-4), in each of aromatic rings with 6-membered rings constituted with $A^{41}$ to $A^{412}$, the number of rings containing nitrogen atoms is preferably 1 or less, and more preferably 0. In the general formula (TpH-4), the connection of the aromatic rings with 6-membered rings constituted with $A^{41}$ to $A^{412}$ is not limited, but it is preferably at a meta- or para-position. Further, it is preferable that the compound represented by the general formula (TpH-4) include a phenyl ring which is a partial structure of a fused ring constituting a triphenylene ring, and the number of aromatic rings connected successively at para-positions be 3 or less.

From the viewpoint of stable operation of the organic electroluminescent element with respect to heat emission during high-temperature driving or element driving, the glass transition temperature (Tg) of a triphenylene-based compound according to the present invention is preferably from 80° C. to 400° C., more preferably from 100° C. to 400° C., and still more preferably from 120° C. to 400° C.

Specific examples of the triphenylene-based compound represented by the general formula (TpH-1) are shown below, but the triphenylene-based compound used in the present invention is not limited thereto.

[Chem. 38]

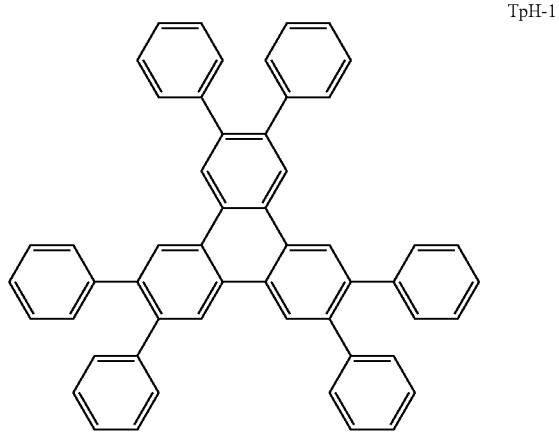

TpH-1

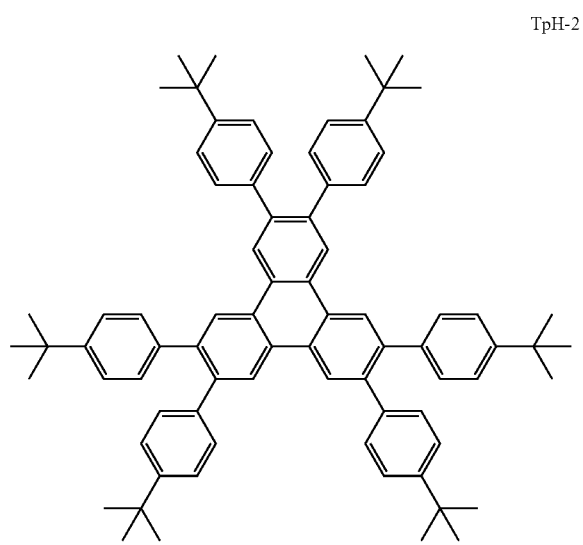

TpH-2

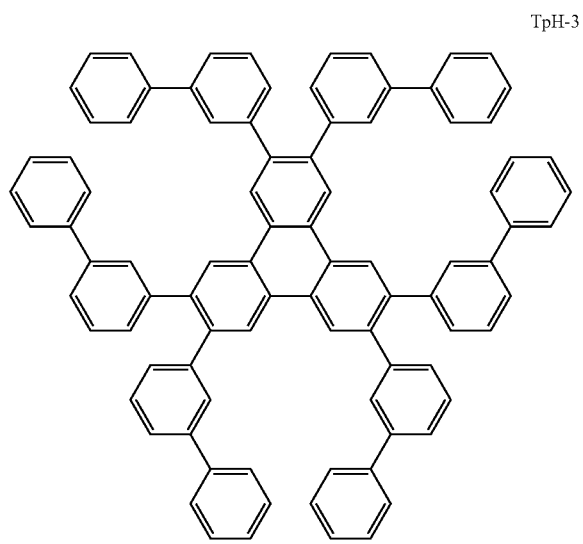

TpH-3

TpH-4
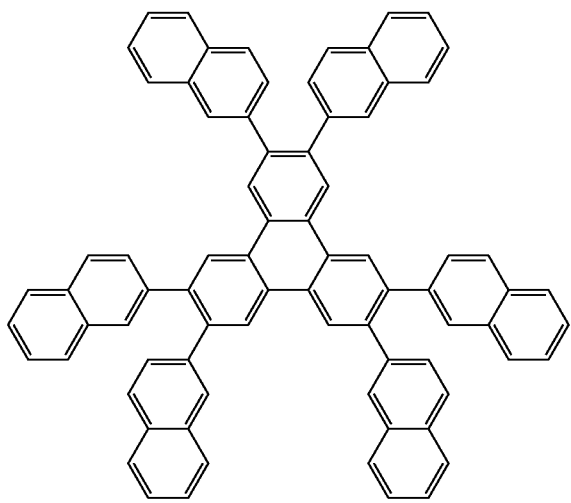
TpH-5
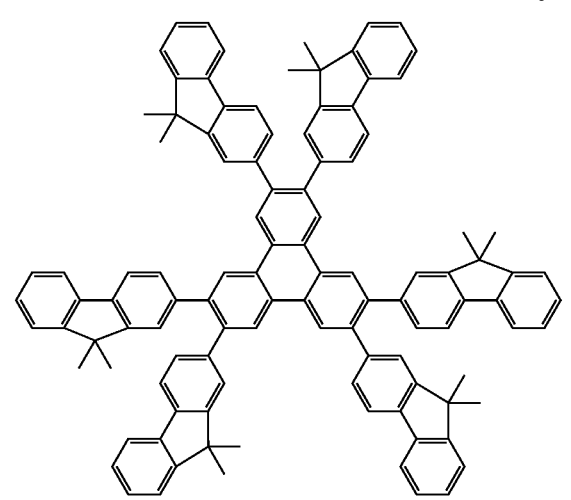
TpH-6
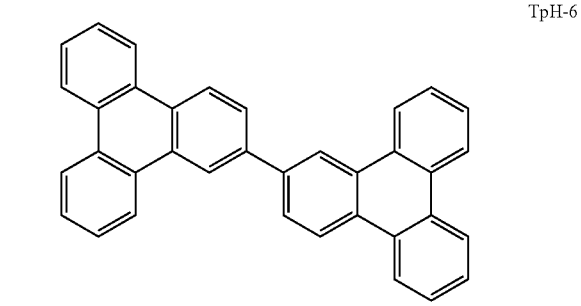
TpH-7
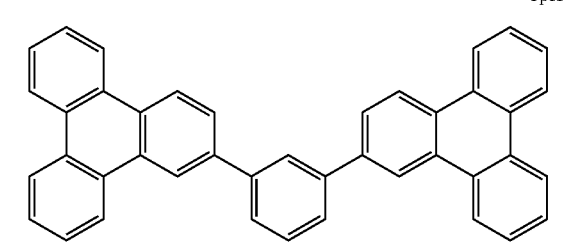
TpH-8
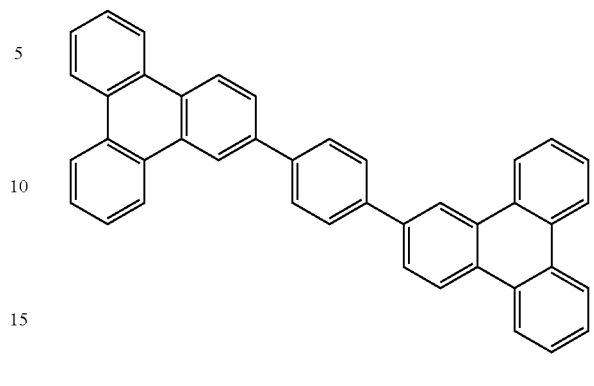
TpH-9
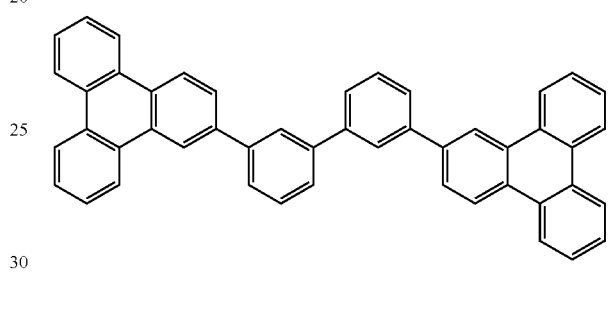
TpH-10
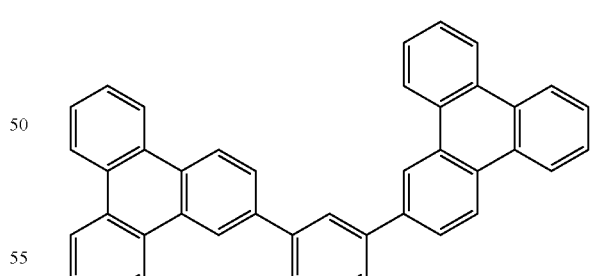
TpH-11
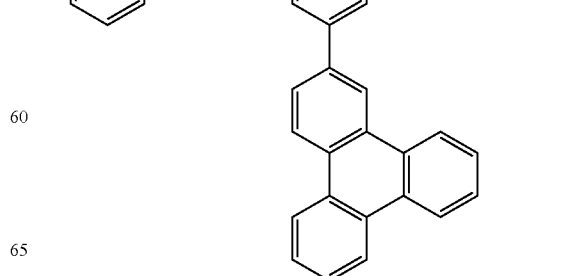

TpH-12
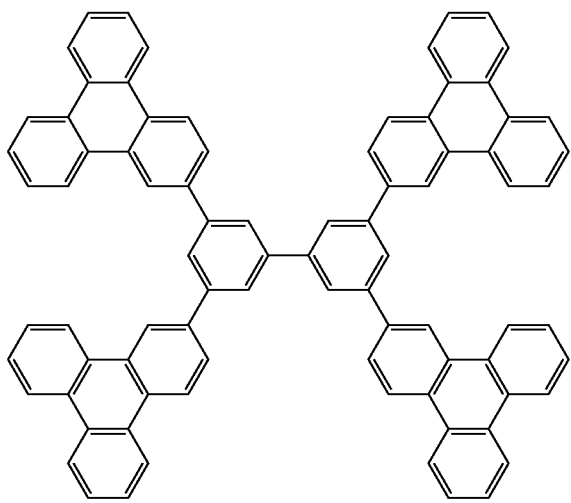
[Chem. 39]
TpH-13
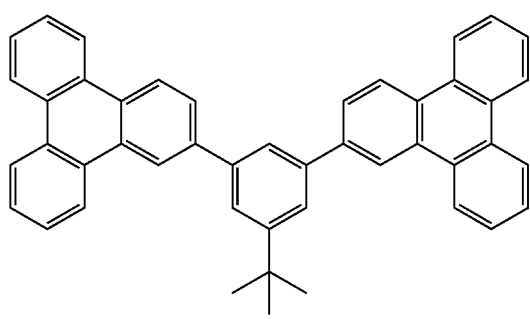
TpH-14
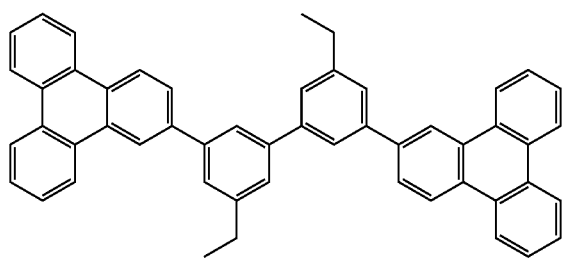
TpH-15
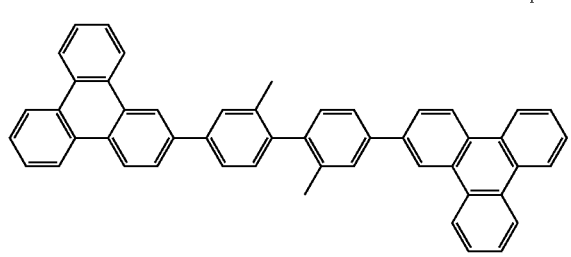
TpH-16
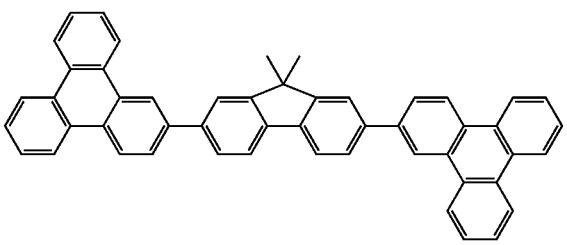
TpH-17
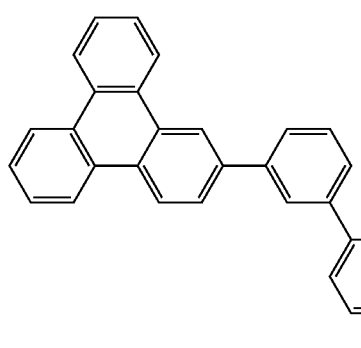
TpH-18
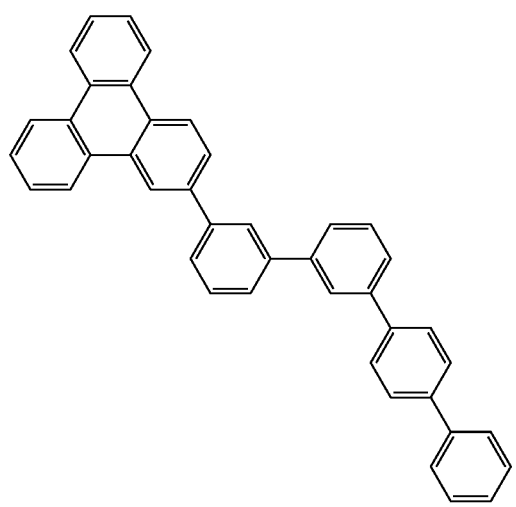
TpH-19
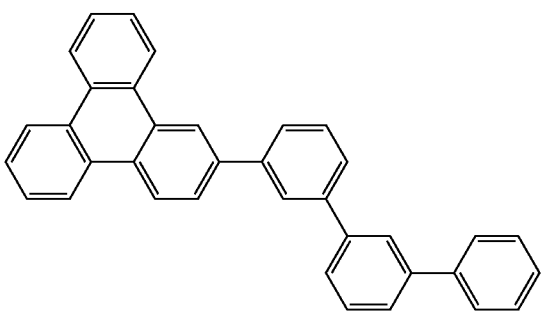

TpH-20
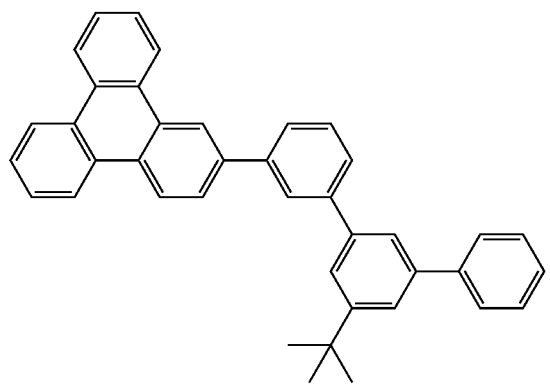

TpH-21
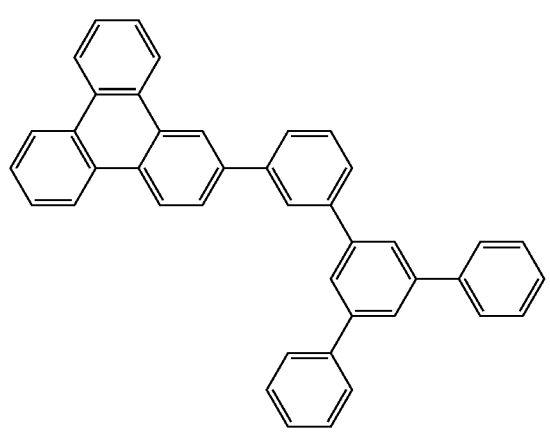

TpH-22
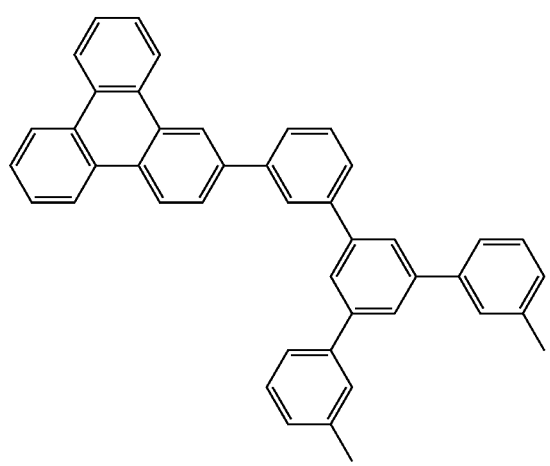

TpH-23
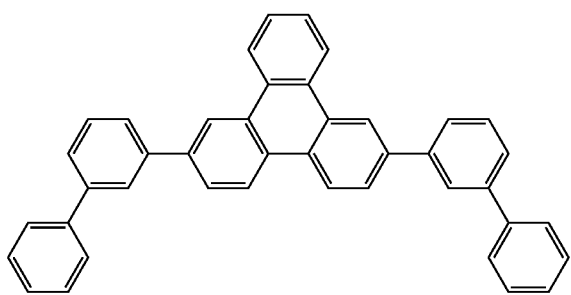

TpH-24
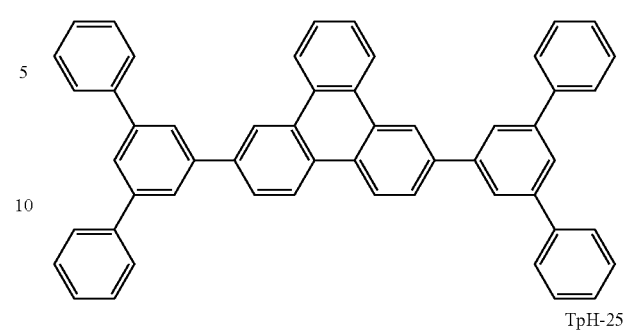

TpH-25

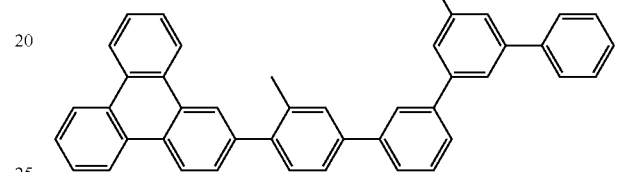

TpH-26
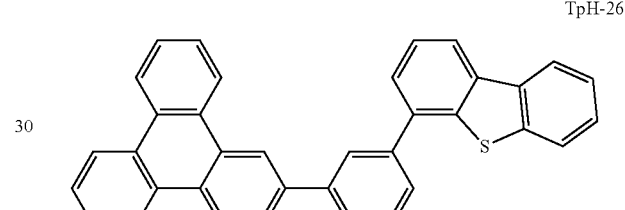

TpH-27
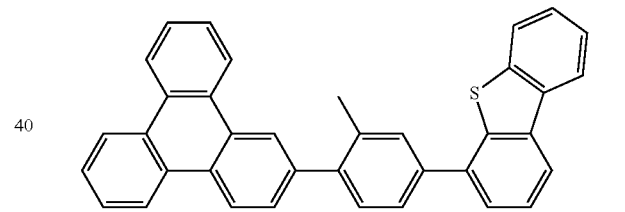

The triphenylene-based compounds exemplified as the triphenylene-based compound represented by the general formula (TpH-1) can be synthesized by the methods described in the pamphlets of WO05/013388, WO06/130598, and WO09/021,107, US2009/0009065, and the pamphlets of WO09/008,311 and WO04/018587.

After the synthesis, it is preferable that the product be purified by column chromatography, recrystallization, and the like, and then purified by sublimation purification. By sublimation purification, it is possible not only to separate the organic impurities but also to effectively remove the inorganic salts, residual solvent, and the like.

In the light emitting layer in the organic electroluminescent element of the present invention, the host material which may be used in combination therewith may be either of a hole transporting host material and an electron transporting host material.

In the light emitting layer, the triplet lowest excited energy ($T_1$ energy) in the film state of the host material is preferably higher than the $T_1$ energy of the phosphorescent light emitting material from the viewpoints of color purity, luminous efficiency, and driving durability.

When the $T_1$ in the film state of the host material is lower than the $T_1$ of the phosphorescent light emitting material, the light emission is lost, and thus, the host material is required to have a higher $T_1$ than the $T_1$ of the phosphorescent light emitting material. Further, even in the case where the $T_1$ of the host material is higher than the $T_1$ of the phosphorescent light emitting material, a small difference in the $T_1$ of the both leads to partial reverse energy movement from the phosphorescent emitting material to the host material, which causes reduction in efficiency. Therefore, there is a demand for a host material having a $T_1$ of a host material higher than the $T_1$ energy of the phosphorescent light emitting material, and high chemical stability and carrier injecting/transporting properties.

By measuring the phosphorescent luminous spectrum of a thin film of the material, the $T_1$ energy can be found from the short-wavelength end thereof. For example, a film of the material is formed in a thickness of about 50 nm by a vacuum deposition method over a washed quartz glass substrate, and the phosphorescent luminous spectrum of the thin film is measured using an F-7000 Hitachi spectrofluorophotometer (Hitachi High-Technologies Corporation) at the temperature of liquid nitrogen. The $T_1$ energy can be determined by converting the rising wavelength on the short-wavelength side of the luminous spectrum thus obtained to energy units.

Moreover, the content of the host compound in the light emitting layer in the organic electroluminescent element of the present invention is not particularly limited, but from the viewpoint of luminous efficiency and driving voltage, it is preferably from 15% by mass to 95% by mass with respect to the total mass of the compounds forming the light emitting layer.

(Other Layers)

The organic electroluminescent element of the present invention may include layers other than the light emitting layer.

Examples of the organic layer other than the light emitting layer which may be included in the organic layer include a hole injecting layer, a hole transporting layer, a blocking layer (a hole blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode, Anode/hole transporting layer/light emitting layer/blocking layer/electron transporting layer/cathode, Anode/hole transporting layer/light emitting layer/blocking layer/electron transporting layer/electron injecting layer/cathode, Anode/hole injecting layer/hole transporting layer/light emitting layer/blocking layer/electron transporting layer/cathode, Anode/hole injecting layer/hole transporting layer/light emitting layer/electron transporting layer/electron injecting layer/cathode, Anode/hole injecting layer/hole transporting layer/light emitting layer/blocking layer/electron transporting layer/electron injecting layer/cathode, and Anode/hole injecting layer/hole transporting layer/blocking layer/light emitting layer/blocking layer/electron transporting layer/electron injecting layer/cathode.

The organic electroluminescent element of the present invention preferably includes at least one (A) organic layer which is preferably disposed between the anode and the light emitting layer. Examples of the (A) organic layer which is preferably disposed between the anode and the light emitting layer include an hole injecting layer, a hole transporting layer, and an electron blocking layer from the anode side.

The organic electroluminescent element of the present invention preferably includes at least one (B) organic layer which is preferably disposed between the cathode and the light emitting layer. Examples of the (B) organic layer which is preferably disposed between the cathode and the light emitting layer include an electron injecting layer, an electron transporting layer, and a hole blocking layer from the cathode side.

Specifically, an example of the preferred aspects of the organic electroluminescent element of the present invention is the aspect shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

Hereinafter, the layers other than the light emitting layer which the organic electroluminescent element of the present invention may have will be described.

(A) Organic Layer Preferably Disposed Between Anode and Light Emitting Layer:

First, the (A) organic layer preferably disposed between the anode and the light emitting layer will be described.

(A-1) Hole Injecting Layer and Hole Transporting Layer

The hole injecting layer and the hole transporting layer are layers having a function of receiving holes from the anode or the anode side and transporting them to the cathode side.

For the hole injecting layer and the hole transporting layer, the detailed descriptions in paragraph Nos. [0165] to [0167] of JP-A-2008-270736 can be applied to the present invention.

The hole injecting layer preferably contains an electron receiving dopant. By incorporating the electron receiving dopant into the hole injecting layer, for example, effects are produced such that the hole injecting properties are enhanced, that the driving voltage is lowered, and that the efficiency is enhanced. The electron receiving dopant may be any one of organic materials or inorganic materials so long as the material is capable of withdrawing electrons from the material to be doped and generating radical cations, and examples thereof include a TCNQ compound such as tetracyanoquinodimethane (TCNQ) and tetrafluorotetracyanoquinodimethane ($F_4$-TCNQ), a hexaazatriphenylene compound such as hexacyanohexaazatriphenylene (HAT-CN, a compound LG 101 as described later); and molybdenum oxide. By interposing only the electron receiving dopant above, as a thin film, between the anode and the electron transporting layer, the same effect can be provided. In this case, this layer is referred to as an electron injecting layer.

The electron receiving dopant in the hole injecting layer is contained preferably in an amount of 0.01% by mass to 50% by mass, more preferably in an amount of 0.1% by mass to 40% by mass, and more preferably in an amount of 0.2% by mass to 30% by mass, with respect to the total mass of the compounds forming the hole injecting layer. In the case of being used as a thin film, the thickness of the electron injecting layer is preferably from 1 nm to 50 nm, more preferably from 3 nm to 30 nm, and still more preferably from 5 nm to 20 nm.

(A-2) Electron Blocking Layer

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer and the anode side.

As the organic compound constituting the electron blocking layer, for example, those exemplified above as the hole transporting material can be applied.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one kind or two or more kinds of the above-described materials or a multilayer structure composed of a plurality of layers having the same composition or different compositions.

The material used in the electron blocking layer preferably has a higher $T_1$ energy than that of the phosphorescent light emitting material in views of color purity, luminous efficiency, and driving durability.

(A-3) Material Particularly Preferably Used in Organic Layer Preferably Disposed Between Anode and Light Emitting Layer In the present invention, examples of the material particularly preferably used in (A) the organic layer preferably disposed between the anode and the light emitting layer include at least one kind of compound represented by the following general formula (M-3).

[Chem. 40]

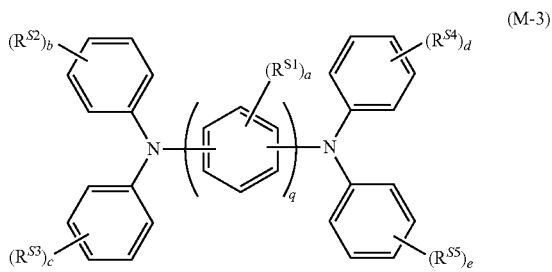

The compound represented by the general formula (M-3) is more preferably contained in the organic layer adjacent to the light emitting layer, between the light emitting layer and the anode, but is not limited in its uses and may be further contained in any layer in the organic layers. A layer into which the compound represented by the general formula (M-3) is introduced may contain any one or a plurality of a light emitting layer, a hole injecting layer, a hole transporting layer, an electron transporting layer, an electron injecting layer, and a charge blocking layer.

The organic layer adjacent to the light emitting layer between the light emitting layer and the anode, in which the compound represented by the general formula (M-3) is contained, is more preferably an electron blocking layer or a hole transporting layer.

In the general formula (M-3), $R^{S1}$ to $R^{S5}$ each independently represent an alkyl group, a cycloalkyl group, an alkenyl group, an alkynyl group, —CN, a perfluoroalkyl group, a trifluorovinyl group, —CO$_2$R, —C(O)R, —NR$_2$, —NO$_2$, —OR, a halogen atom, an aryl group, or a heteroaryl group, and may further have a substituent Z. Rs each independently represent a hydrogen atom, an alkyl group, a perhaloalkyl group, an alkenyl group, an alkynyl group, a heteroalkyl group, an aryl group, or a heteroaryl group. When a plurality of $R^{S1}$ to $R^{S5}$ are present, those groups may be bonded to each other to form a ring, and may further have a substituent Z.

a represents an integer of 0 to 4, and when a plurality of $R^{S1}$s are present, the $R^{S1}$s may be the same as or different from one another, and may be bonded to each other to form a ring. b to e each independently represent an integer of 0 to 5, and when a plurality of groups are present for each $R^{S2}$ to $R^{S5}$, the groups may be the same as or different from one another, and any two thereof may be bonded to each other to form a ring.

q is an integer of 1 to 5, and when q is 2 or more, a plurality of $R^{S1}$s may be the same as or different from one another and may be bonded to each other to form a ring.

The alkyl group may have a substituent and may be saturated or unsaturated, and examples of the group that may be substituted include the substituent Zs as described above. The alkyl group represented by $R^{S1}$ to $R^{S5}$ is preferably an alkyl group having a total carbon number of 1 to 8, and more preferably an alkyl group having a total carbon number of 1 to 6, and examples thereof include a methyl group, an ethyl group, an i-propyl group, a cyclohexyl group, and a t-butyl group.

The cycloalkyl group may have a substituent and may be saturated or unsaturated, and examples of the group that may be substituted include the substituent Zs as described above. The cycloalkyl group represented by $R^{S1}$ to $R^{S5}$ is preferably a cycloalkyl group having 4 to 7 ring members, and more preferably a cycloalkyl group having a total carbon number of 5 or 6, and examples thereof include a cyclopenthyl group and a cyclohexyl group.

The alkenyl group represented by $R^{S1}$ to $R^{S5}$ preferably has 2 to 30 carbon atoms, more preferably has 2 to 20 carbon atoms, and particularly preferably has 2 to 10 carbon atoms, and examples thereof include vinyl, allyl, 1-propenyl, 1-isopropenyl, 1-butenyl, 2-butenyl, and 3-pentenyl.

The alkynyl group represented by $R^{S1}$ to $R^{S5}$ preferably has 2 to 30 carbon atoms, more preferably has 2 to 20 carbon atoms, and particularly preferably has 2 to 10 carbon atoms, and examples thereof include ethynyl, propargyl, 1-propynyl, and 3-pentynyl.

The perfluoroalkyl group represented by $R^{S1}$ to $R^{S5}$ includes a group obtained by substituting all the hydrogen atoms in the above-mentioned alkyl group with fluorine atoms.

The aryl group represented by $R^{S1}$ to $R^{S5}$ is preferably a substituted or unsubstituted aryl group having 6 to 30 carbon atoms, and examples thereof include a phenyl group, a tolyl group, a biphenyl group, and a terphenyl group.

The heteroaryl group represented by $R^{S1}$ to $R^{S5}$ is preferably a heteroaryl group having 5 to 8 carbon atoms, and more preferably a substituted or unsubstituted 5- or 6-membered heteroaryl group, and examples thereof include a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a triazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group, a carbazolyl group, a dibenzofuryl group, a dibenzothienyl group, and a pyridoindolyl group. Preferred examples thereof include a pyridyl group, a pyrimidinyl group, an imidazolyl group, and a thienyl group, and more preferred examples thereof include a pyridyl group and a pyrimidinyl group.

$R^{S1}$ to $R^{S5}$ are each preferably a hydrogen atom, an alkyl group, a cyano group, a trifluoromethyl group, a perfluoroalkyl group, a dialkylamino group, a fluoro group, an aryl group, or a heteroaryl group, more preferably a hydrogen atom, an alkyl group, a cyano group, a trifluoromethyl group, a fluoro group, or an aryl group, and still more preferably a hydrogen atom, an alkyl group, or an aryl group. The substituent Z is preferably an alkyl group, an alkoxy group, a fluoro group, a cyano group, or a dialkylamino group, and more preferably a hydrogen atom or an alkyl group.

Any two of $R^{S1}$ to $R^{S5}$ may be bonded to each other to form a fused 4- to 7-membered ring, the fused 4- to 7-membered ring is cycloalkyl, aryl, or heteroaryl, and the fused 4- to 7-membered ring may further have a substituent Z. The definitions and the preferred ranges of the formed cycloalkyl, aryl and heteroaryl are the same as those of the cycloalkyl group, the aryl group, and the heteroaryl group defined in $R^{S1}$ to $R^{S5}$.

In the case where the compound represented by the general formula (M-3) is used in a hole transporting layer, the compound represented by the general formula (M-3) is preferably contained in an amount of 50% by mass to 100% by mass, more preferably contained in an amount of 80% by mass to 100% by mass, and particularly preferably contained in an amount of 95% by mass to 100% by mass.

In addition, in the case where the compound represented by the general formula (M-3) is used in a plurality of organic layers, the compound is preferably contained in each layer within the above range.

The thickness of the hole transporting layer containing the compound represented by the general formula (M-3) is preferably from 1 nm to 500 nm, more preferably from 3 nm to 200 nm, and still more preferably from 5 nm to 100 nm. In addition, the hole transporting layer is preferably provided to be adjacent to the light emitting layer.

Specific examples of the compound represented by the general formula (M-3) are shown below, but the present invention is not limited thereto.

[Chem. 41]

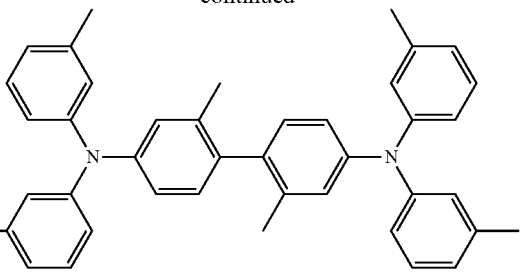

-continued

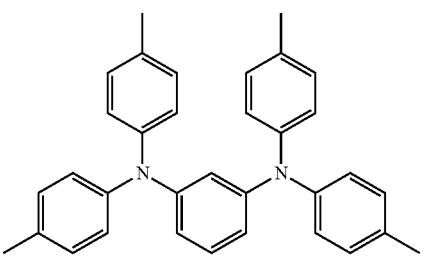

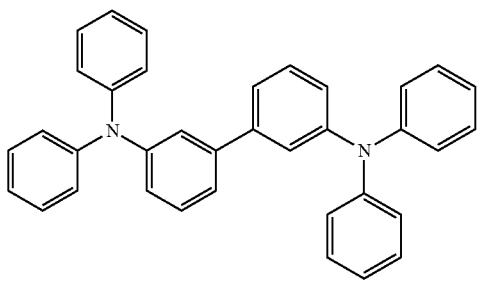

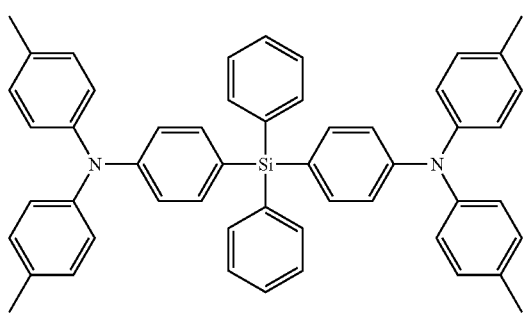

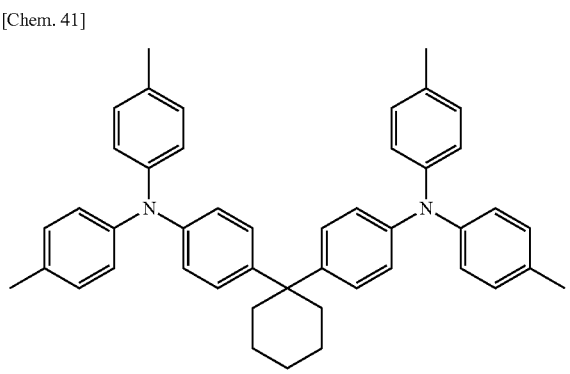

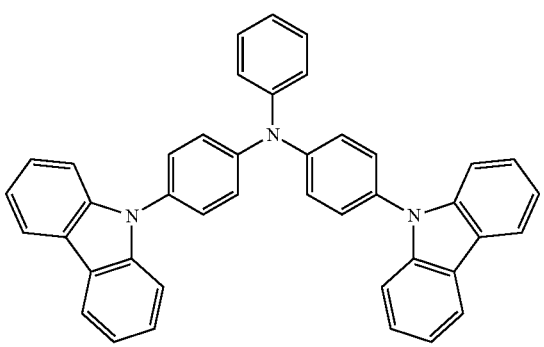

-continued
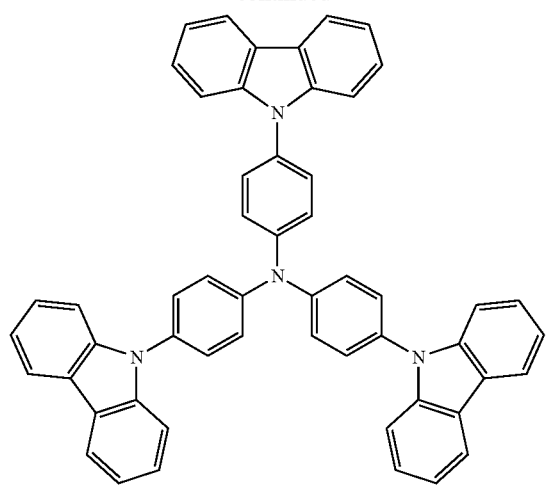
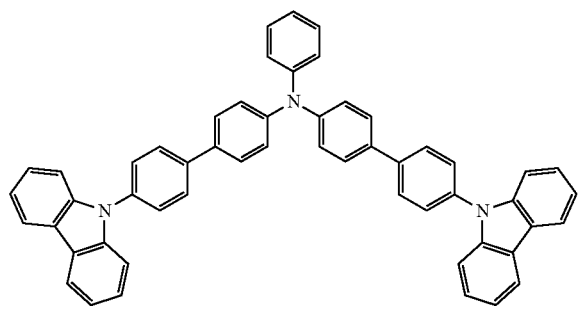
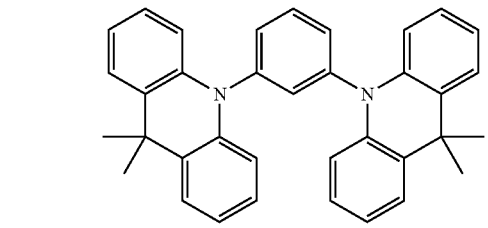
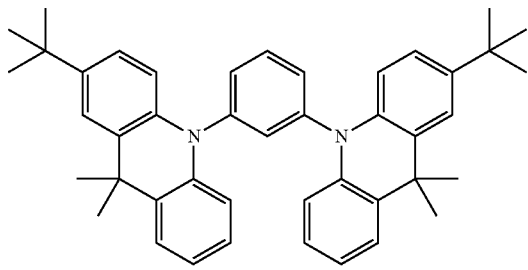
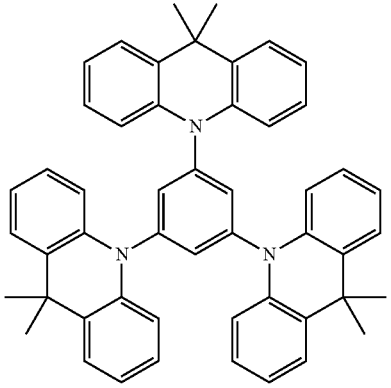
-continued
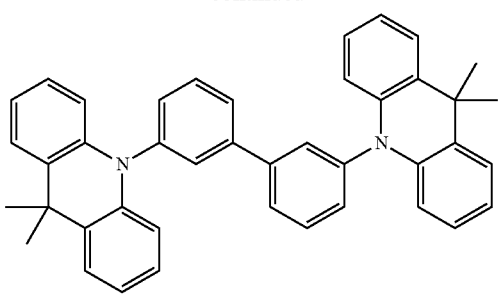
[Chem. 42]
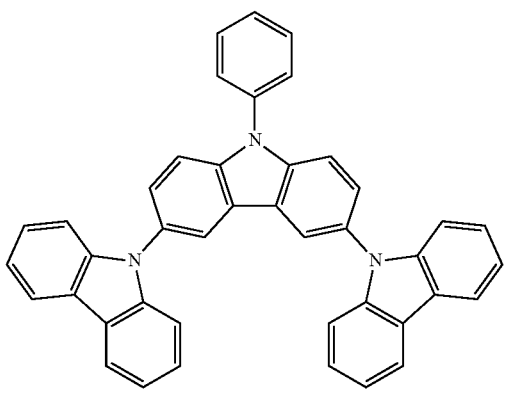
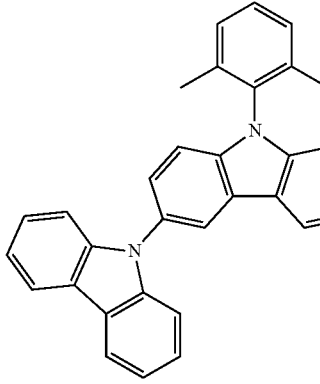
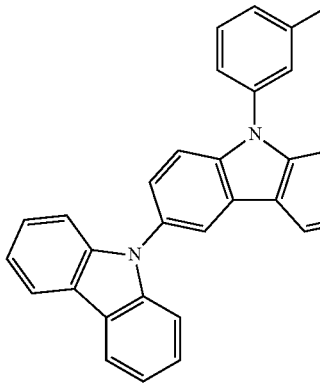

101
-continued
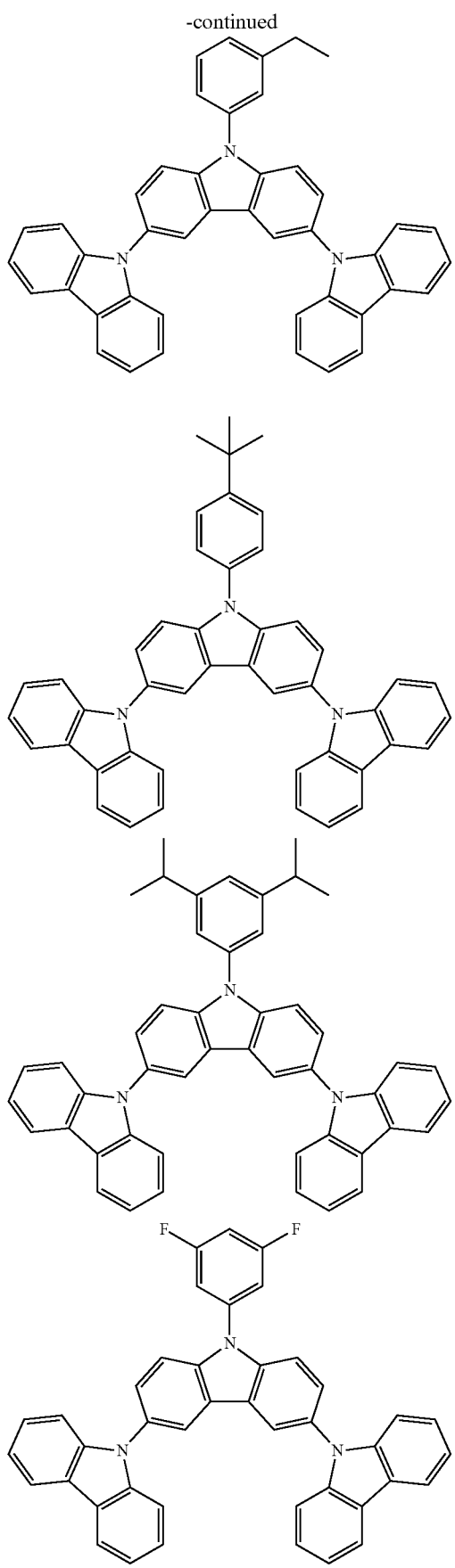
102
-continued
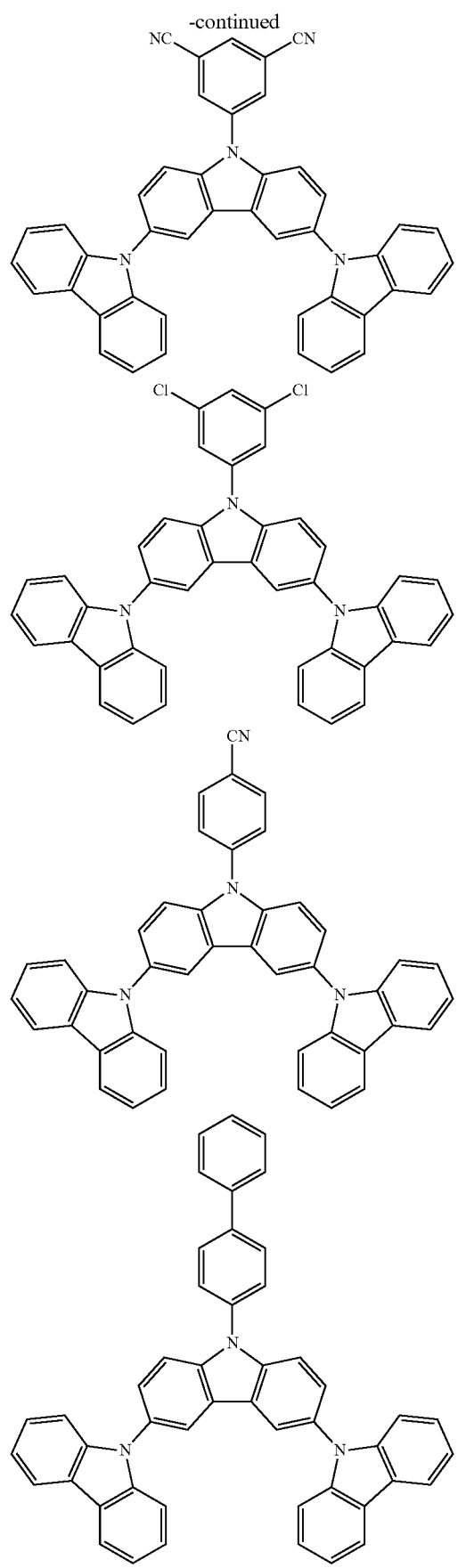

103
-continued
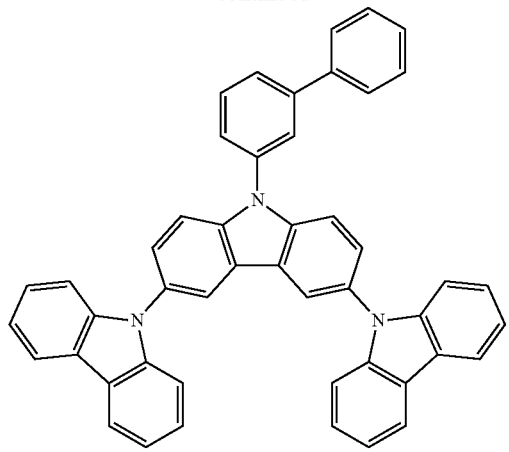
[Chem. 43]
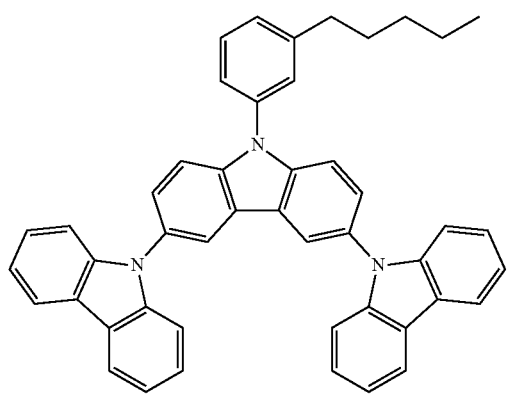
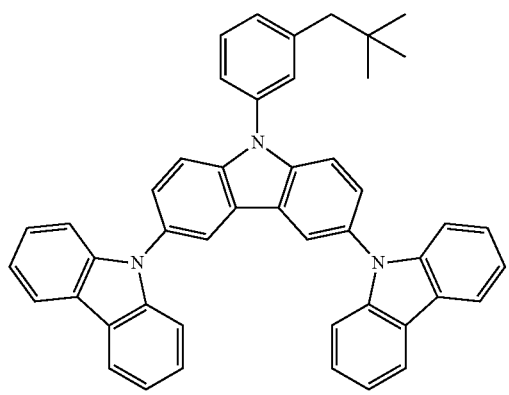
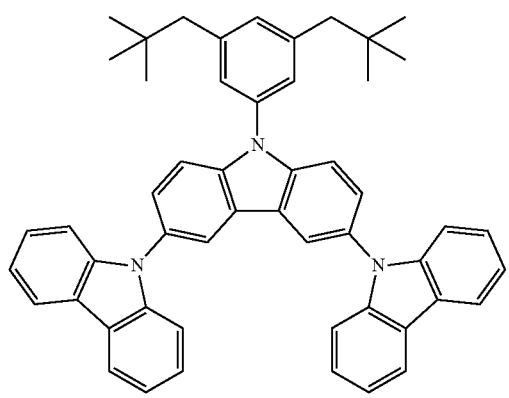
104
-continued
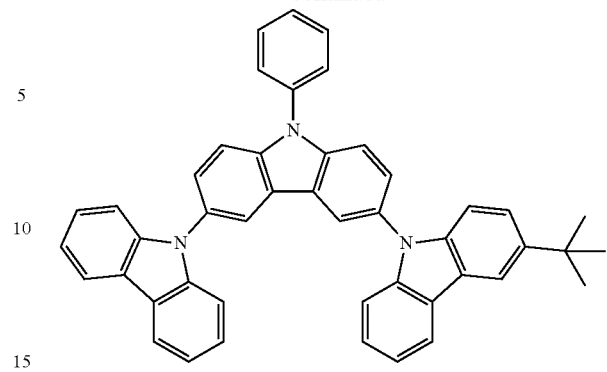
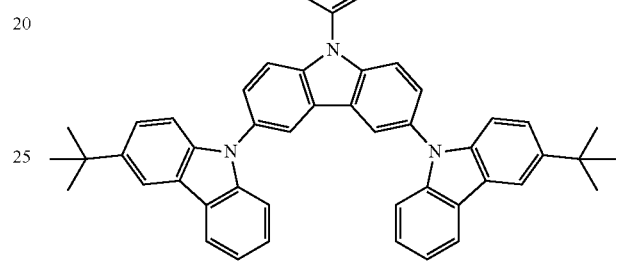
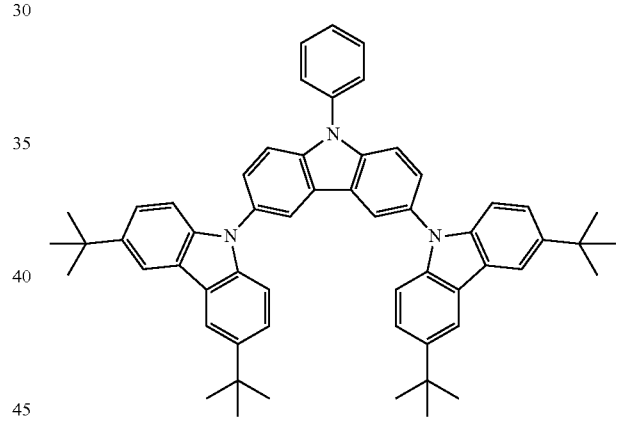
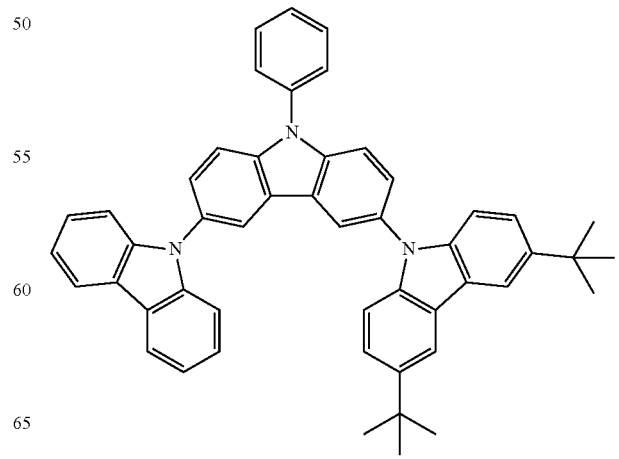

105
-continued
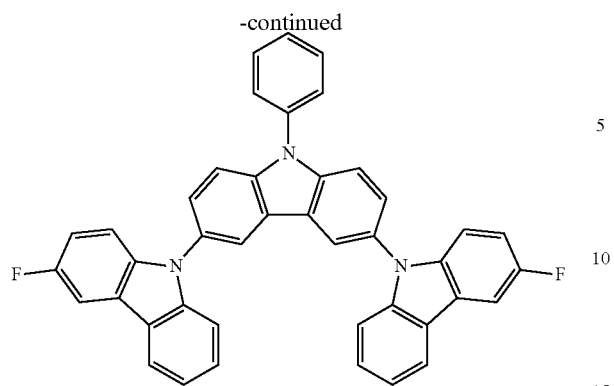
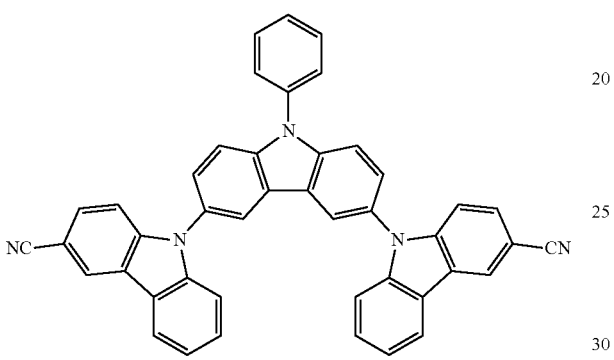
[Chem. 44]
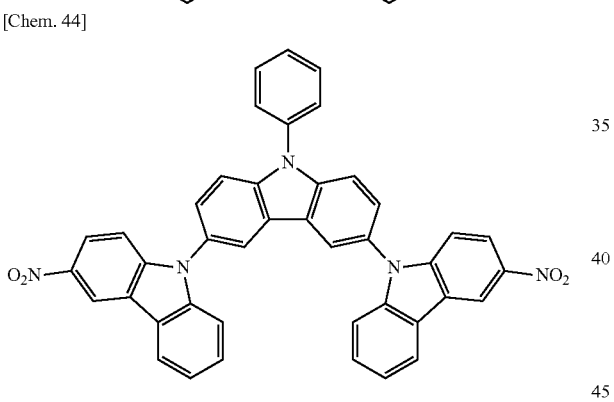
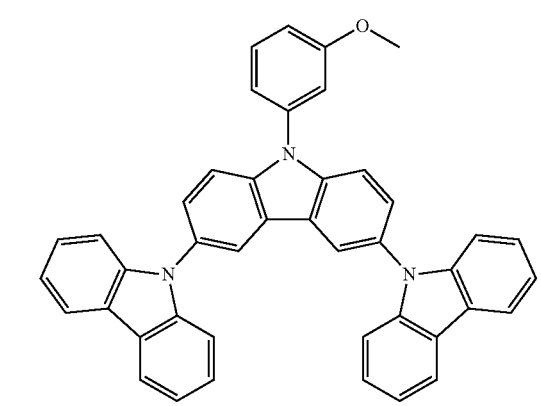
106
-continued
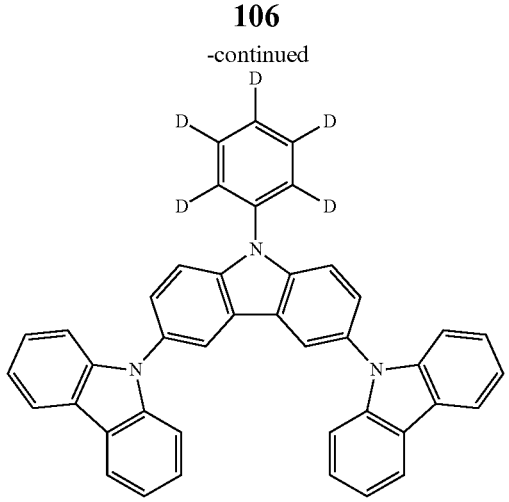
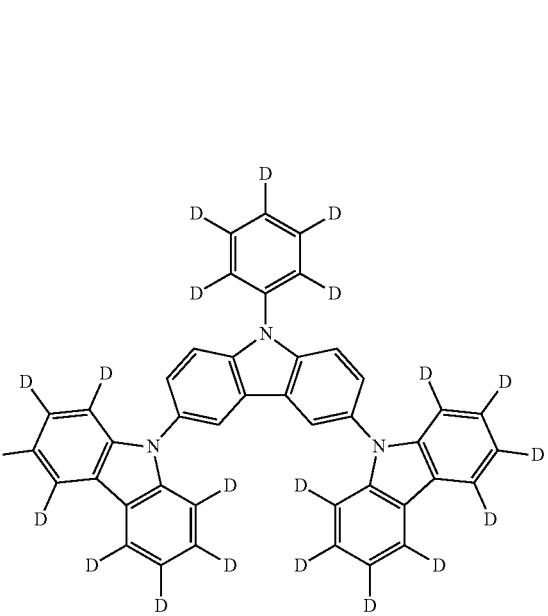
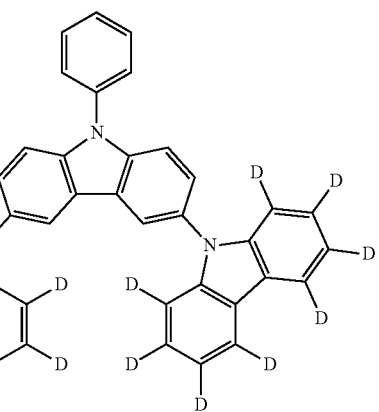

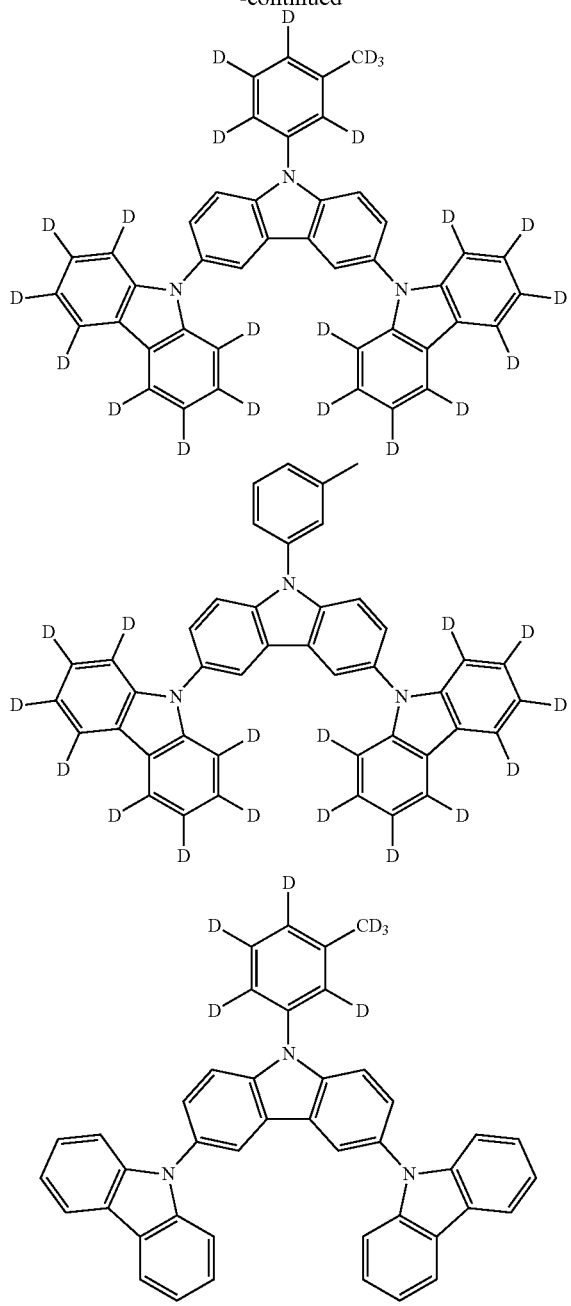
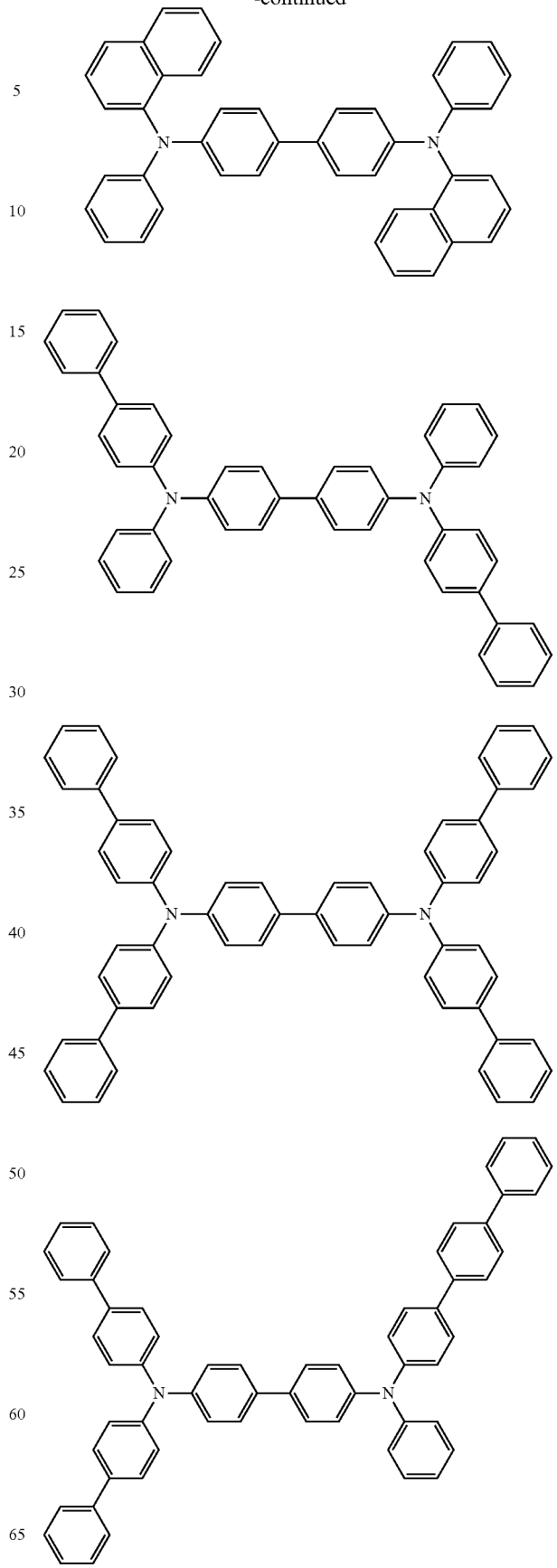

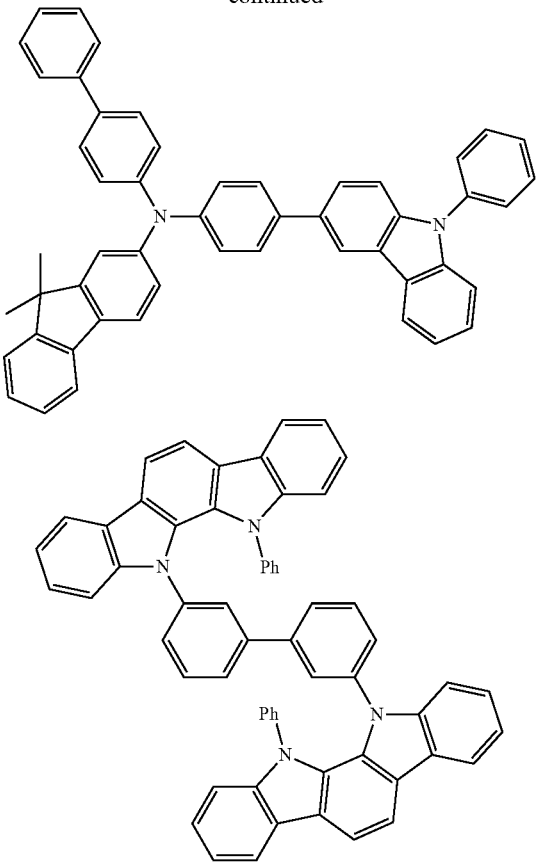

(B) Organic Layer Preferably Disposed Between Cathode and Light Emitting Layer

Next, the (B) organic layer preferably disposed between the cathode and the light emitting layer will be described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (TpH-1) can be used. As the other electron transporting materials, anyone selected from aromatic ring tetracarboxylic acid anhydrides, such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof; organic silane derivatives typified by silole; and hydrocarbon compounds with fused rings, such as naphthalene, anthracene, phenanthrene, triphenylene, and pyrene is preferred, and any one selected from pyridine derivatives, benzimidazole derivatives, imidazopyridine derivatives, metal complexes, and hydrocarbon compounds with fused rings is more preferred.

From the viewpoint of decreasing the driving voltage, the thickness of each of the electron injecting layer and the electron transporting layer is preferably 500 nm or less.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one kind or two or more kinds of the above-described materials or a multilayer structure composed of a plurality of layers having the same composition or different compositions.

The electron injecting layer may contain an electron donating dopant. By incorporating the electron donating dopant in the electron injecting layer, there are effects that, for example, the electron injecting properties are improved, the driving voltage is lowered, and the efficiency is improved. The electron donating dopant may be any one of organic materials and inorganic materials as long as it is capable of giving electrons to the material to be doped and generating radical anions, and examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably 0.5% by mass to 30% by mass, with respect to the total mass of the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order that the $T_1$ energy of the organic compound in the film state constituting the hole blocking layer prevents the energy movement of excitons produced in the light emitting layer and does not lower the luminous efficiency, it is preferably higher than the $T_1$ energy of the light emitting material.

As an example of the organic compound constituting the hole blocking layer, for example, the compound represented by the general formula (TpH-1) can be used.

Examples of the organic compounds constituting the hole blocking layer, other than the compound represented by the general formula (TpH-1), include aluminum complexes such as aluminum (III) tris-8-hydroxyquinoline (Alq), aluminum (III) bis(2-methyl-8-quinolinato) 4-phenylphenolate (abbreviated as Balq), triazole derivatives, and phenanthroline derivatives such as 2,9-dimethyl-4,7-diphenyl-1,10-phenanthroline (abbreviated as BCP).

The thickness of the hole blocking layer is preferably from 1 nm to 500 nm, more preferably from 3 nm to 100 nm, and still more preferably from 5 nm to 50 nm.

The hole blocking layer may have either a single layer structure composed of one kind or two or more kinds of the above-described materials or a multilayer structure composed of a plurality of layers having the same composition or different compositions.

The material used in the hole blocking layer preferably has higher $T_1$ energy than that of the phosphorescent light emitting material from the viewpoints of color purity, luminous efficiency, and driving durability.

(B-3) Material which is Particularly Preferably Used in Organic Layer, Preferably Disposed Between Cathode and Light Emitting Layer For the organic electroluminescent element of the present invention, examples of the material which is particularly preferably used in the (B) materials for an organic layer, preferably disposed between the cathode and the light emitting layer include the compound represented by the general formula (TpH-1), a compound represented by the following general formula (P-1), and a compound represented by the following general formula (O-1).

Hereinafter, the compound represented by the general formula (O-1) and the compound represented by the general formula (P-1) will be described.

The organic electroluminescent element of the present invention preferably includes at least one organic layer between the light emitting layer and the cathode, and the organic layer preferably contains at least one of compounds represented by the following general formula (O-1), from the viewpoint of efficiency or driving voltage of an element. Hereinafter, the general formula (O-1) will be described.

[Chem. 46]

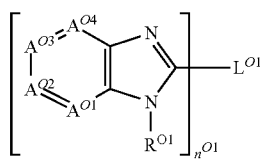

(O-1)

(In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and a plurality of $R^A$s may be the same as or different from each other. $L^{O1}$ represents any of divalent to hexavalent linking groups with an aryl ring or a heteroaryl ring. $n^{O1}$ represents an integer of 2 to 6.)

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the Substituent Group A as described above. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group, more preferred examples thereof include an alkyl group and an aryl group, and still more preferred examples thereof include an aryl group. In the case where the aryl group of $R^{O1}$ has a plurality of substituents, the plurality of substituents may be bonded to each other to form a 5- or 6-membered ring. The aryl group of $R^{O1}$ is preferably a phenyl group which may have a substituent selected from Substituent Group A, more preferably a phenyl group which may be substituted with an alkyl group or an aryl group, and still more preferably an unsubstituted phenyl group or 2-phenylphenyl group.

$A^{O1}$ to $A^{O4}$ each independently represent C—$R^A$ or a nitrogen atom. It is preferable that 0 to 2 groups out of $A^{O1}$ to $A^{O4}$ be nitrogen atoms; and it is more preferable that 0 or 1 group out of $A^{O1}$ to $A^{O4}$ be nitrogen atoms. It is preferable that all of $A^{O1}$ to $A^{O4}$ be C—$R^A$, or $A^{O1}$ be a nitrogen atom, and $A^{O2}$ to $A^{O4}$ be C—$R^A$; it is more preferable that $A^{O1}$ be a nitrogen atom and $A^{O2}$ to $A^{O4}$ be C—$R^A$; and it is still more preferable that $A^{O1}$ be a nitrogen atom, $A^{O2}$ to $A^{O4}$ be C—$R^A$, and $R^A$s be all hydrogen atoms.

$R^A$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), which may have a substituent selected from the Substituent Group A as described above. Further, a plurality of $R^A$s may be the same as or different from each other. $R^A$ is preferably a hydrogen atom or an alkyl group, and more preferably a hydrogen atom.

$L^{O1}$ represents any of divalent to hexavalent linking groups including an aryl ring (preferably having 6 to 30 carbon atoms) or a heteroaryl ring (preferably having 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the Substituent Group A as described above, and in a case of having the substituent, the substituent is preferably an alkyl group, an aryl group, or a cyano group. Specific examples of $L^{O1}$ include the following.

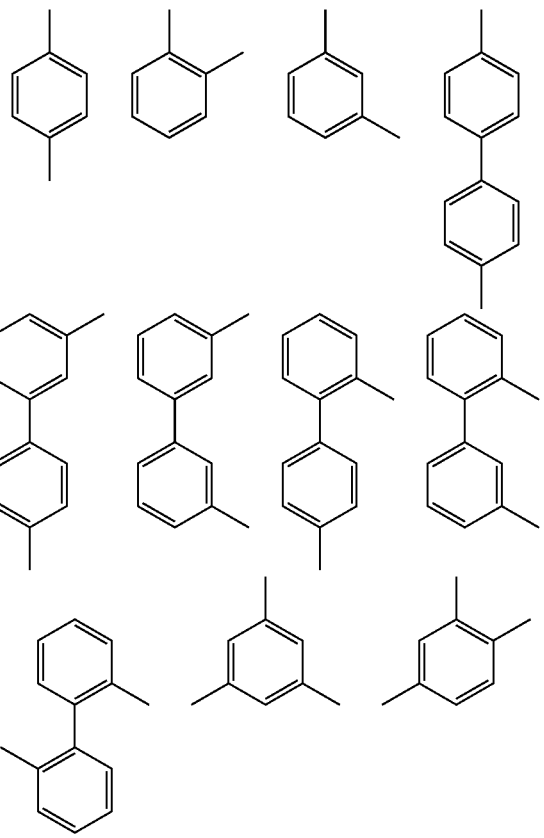

-continued

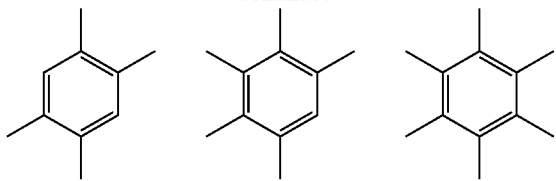

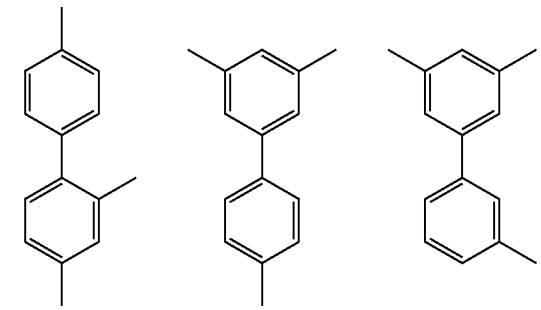

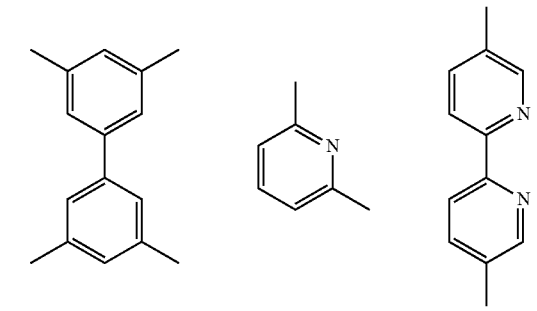

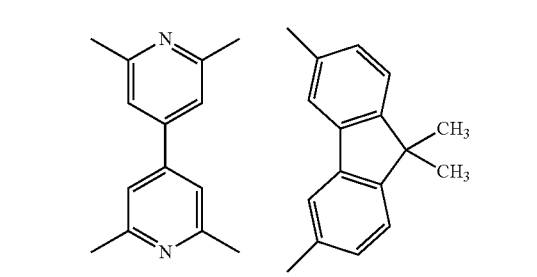

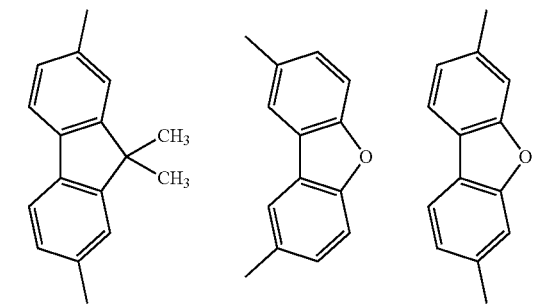

-continued

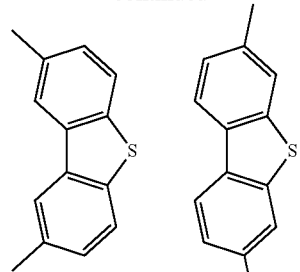

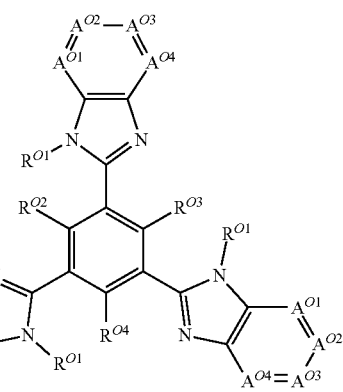

$n^{O1}$ represents an integer of 2 to 6, preferably an integer of 2 to 4, and more preferably 2 or 3. $n^{O1}$ is most preferably 3 from the viewpoint of the efficiency of an element, or most preferably 2 from the viewpoint of the durability of an element.

The compound represented by the general formula (O-1) is more preferably a compound represented by the following general formula (O-2).

[Chem. 48]

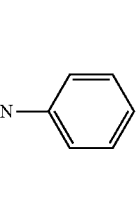

(O-2)

(In the general formula (O-2), $R^{O1}$s represent an alkyl group, an aryl group, or a heteroaryl group. $R^{O2}$ to $R^{O4}$ each independently represent a hydrogen atom, an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and a plurality of $R^A$s may be the same as or different from one another.)

$R^{O1}$ and $A^{O1}$ to $A^{O4}$ have the same definitions as $R^{O1}$ and $A^{O1}$ to $A^{O4}$ in the general formula (O-1) described above, and the preferred ranges thereof are also the same.

$R^{O2}$ to $R^{O4}$ each independently represent a hydrogen atom, an alkyl group (preferably having 1 to 8 carbon atoms), an aryl group (preferably having 6 to 30 carbon atoms), or a heteroaryl group (preferably having 4 to 12 carbon atoms), and these groups may have a substituent selected from the Substituent Group A as described above. $R^{O2}$ to $R^{O4}$ are preferably a hydrogen atom, an alkyl group, or an aryl group, more preferably a hydrogen atom or an aryl group, and most preferably a hydrogen atom.

The glass transition temperature (Tg) of the compound represented by the general formula (O-1) is preferably from 100° C. to 300° C., more preferably from 120° C. to 300° C., still more preferably from 120° C. to 300° C., and even still more preferably from 140° C. to 300° C., from the viewpoint of stability at the time of storage at a high temperature, or stable operation during driving at a high temperature or against heat generation during driving.

Specific examples of the compound represented by the general formula (O-1) are shown below, but the present invention is not limited thereto.

[Chem. 49]

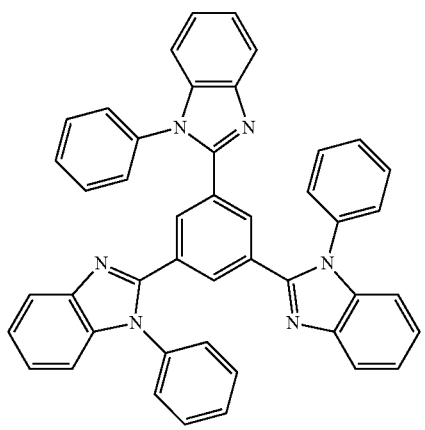

OM-1

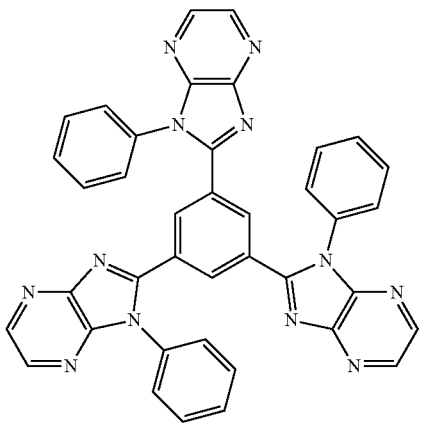

OM-3

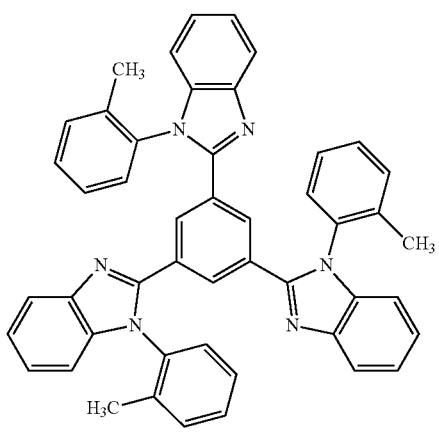

OM-4

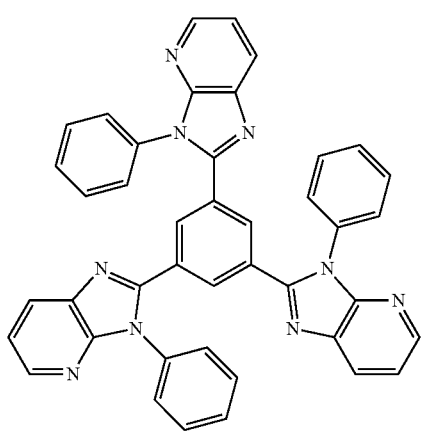

OM-2

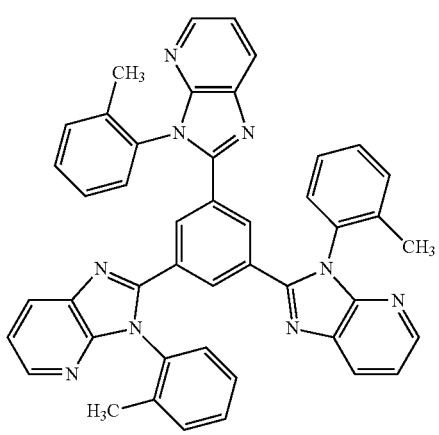

OM-5

OM-6
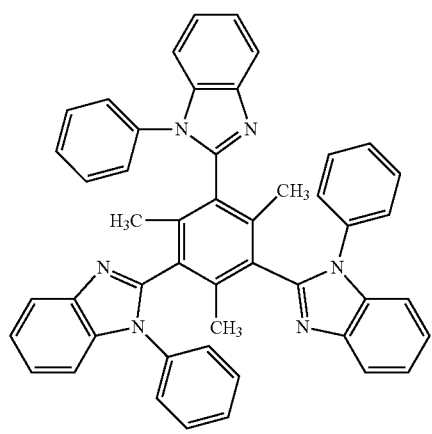
OM-7
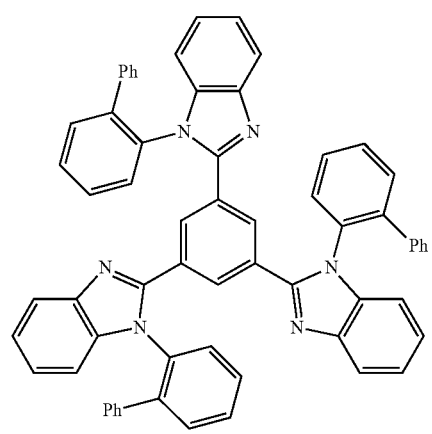
OM-8
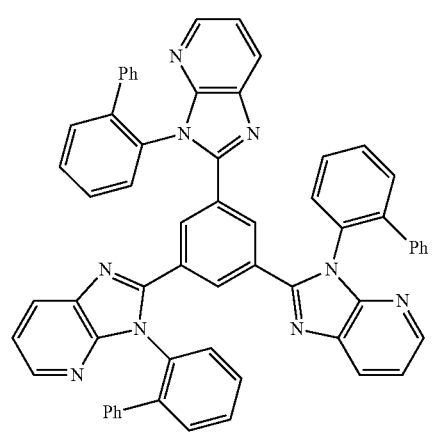
OM-9
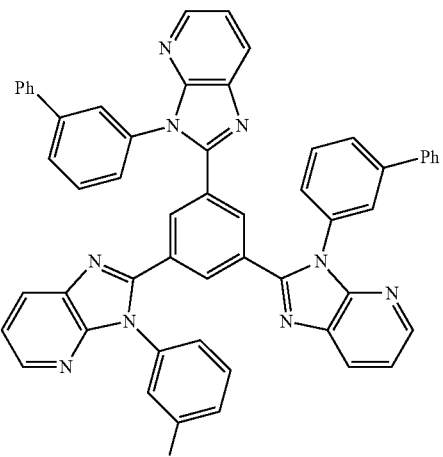
[Chem. 50]
OM-10
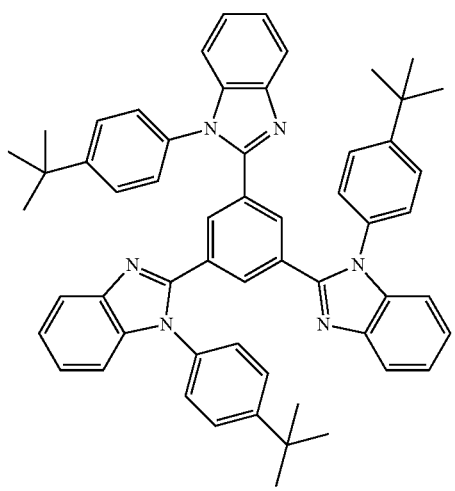
OM-11
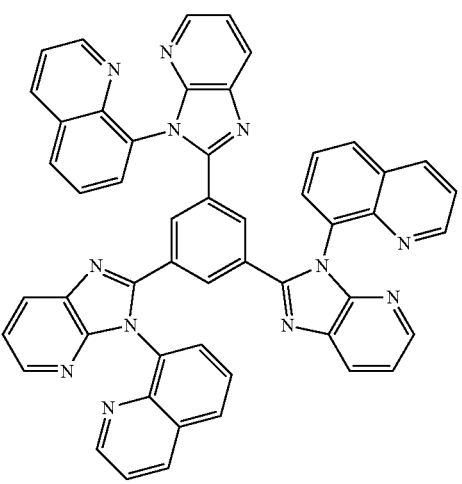

OM-12
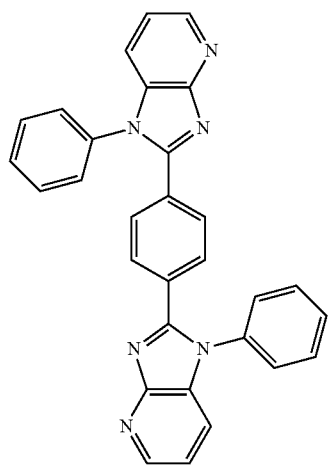
OM-13
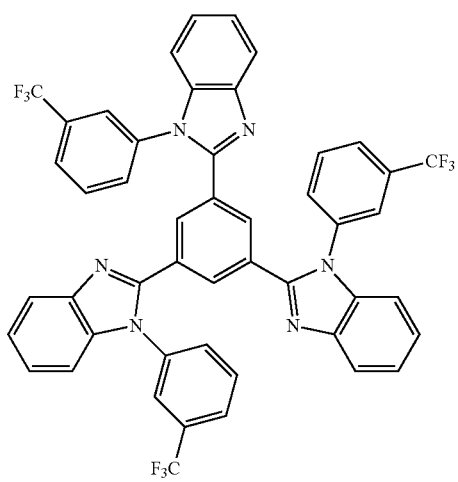
OM-14
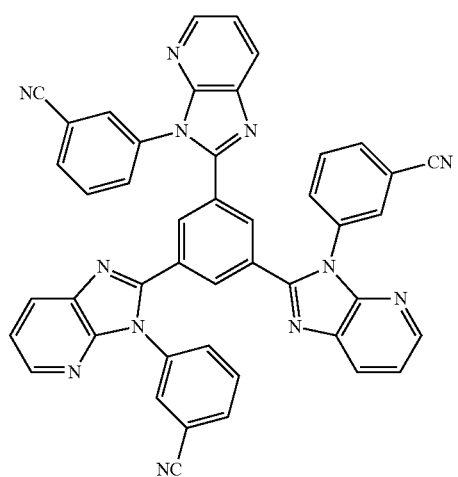
OM-15
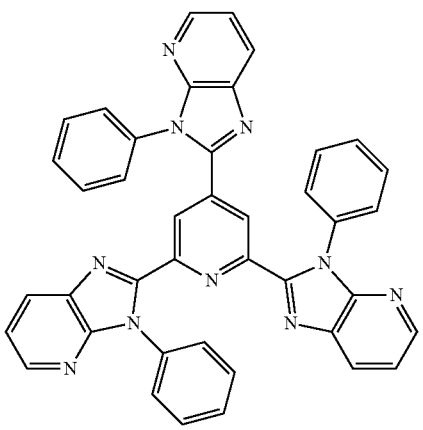
OM-16
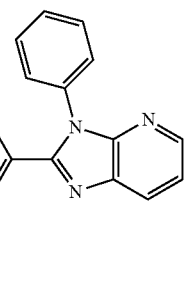
OM-17
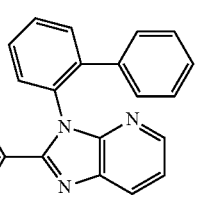
OM-18
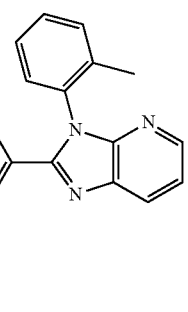

OM-19

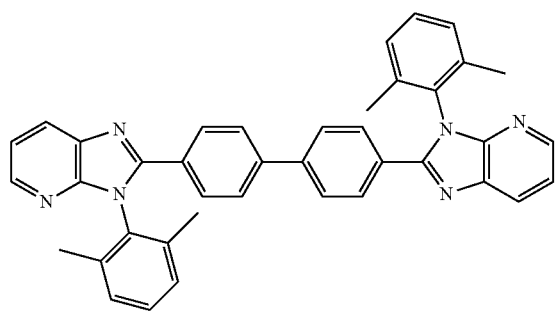

OM-20

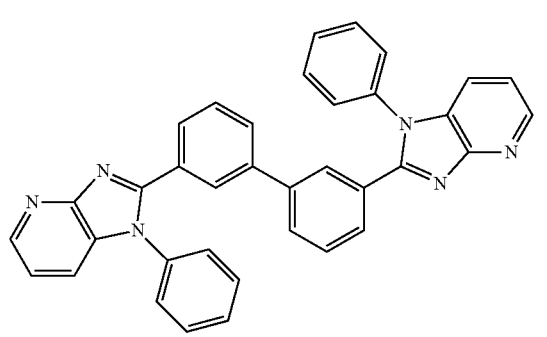

OM-21

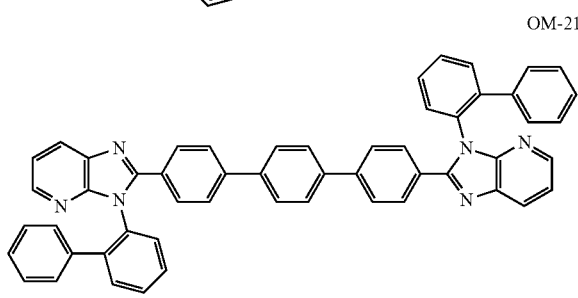

OM-22

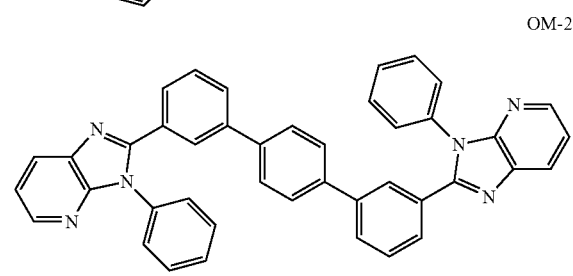

The compound represented by the general formula (O-1) can be synthesized by the method described in JP-A-2001-335776. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (O-1) is preferably contained in the organic layer between the light emitting layer and the cathode, however, it is more preferably contained in the layer on the cathode side adjacent to the light emitting layer.

The compound represented by the general formula (O-1) is contained in the amount of preferably from 70% by mass to 100% by mass, and more preferably from 85% by mass to 100% by mass, with respect to the total mass of the organic layer added.

The organic electroluminescent element of the present invention preferably includes at least one layer of organic layers between the light emitting layer and the cathode, and it is preferable that the organic layer contain at least one kind of compounds represented by the following general formula (P), from the viewpoint of efficiency or the driving voltage of an element. Hereinafter, the general formula (P) will be described.

[Chem. 51]

General Formula (P)

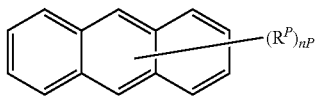

(In the general formula (P), $R^P$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the Substituent Group A as described above. nP represents an integer of 1 to 10, and in the case where there are a plurality of $R^P$s, these may be the same as or different from each other. At least one of $R^P$s is a substituent represented by the following general formulae (P-1) to (P-3).)

[Chem. 52]

General Formula (P-1)

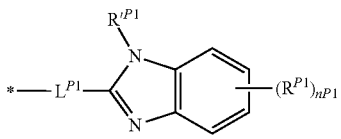

General Formula (P-2)

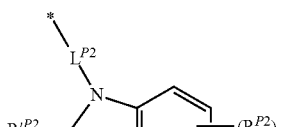

General Formula (P-3)

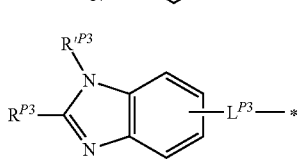

(In the general formulae (P-1) to (P-3), $R^{P1}$ to $R^{P3}$ and $R^{\prime P1}$ to $R^{\prime P3}$ each represent an alkyl group (preferably having 1 to 8 carbon atoms), an aryl group (preferably having 6 to 30 carbon atoms), or a heteroaryl group (preferably having 4 to 12 carbon atoms), which may have a substituent selected from the Substituent Group A as described above. $n^{P1}$ and $n^{P2}$ represents an integer of 0 to 4, and in the case where there are a plurality of $R^{P1}$ to $R^{P3}$ and $R^{\prime P1}$ to $R^{\prime P3}$, they may be the same as or different from each other. $L^{P1}$ to $L^{P3}$ represent any one of divalent linking groups consisting of a single bond, an aryl ring, and a heteroaryl ring. * represents a binding position with the anthracene ring of the general formula (P).)

A preferred substituent other than the substituents represented by (P-1) to (P-3) as $R^P$ is an aryl group, a more preferred substituent is any one of a phenyl group, a biphenyl group, a terphenyl group, and a naphthyl group, and a still more preferred substituent is a naphthyl group.

$R^{P1}$ to $R^{P3}$ and $R'^{P1}$ to $R'^{P3}$ are preferably any one of an aryl group and a heteroaryl group, more preferably an aryl group, still more preferably any one of a phenyl group, a biphenyl group, a terphenyl group, and a naphthyl group, and most preferably a phenyl group.

$L^{P1}$ to $L^{P3}$ are preferably any one of a single bond and a divalent linking group consisting of aryl rings, more preferably any one of a single bond, phenylene, biphenylene, terphenylene, and naphthylene, and still more preferably any one of a single bond, phenylene, and naphthylene.

Specific examples of the compound represented by the general formula (P) are shown below, but the present invention is not limited thereto.

[Chem. 53]

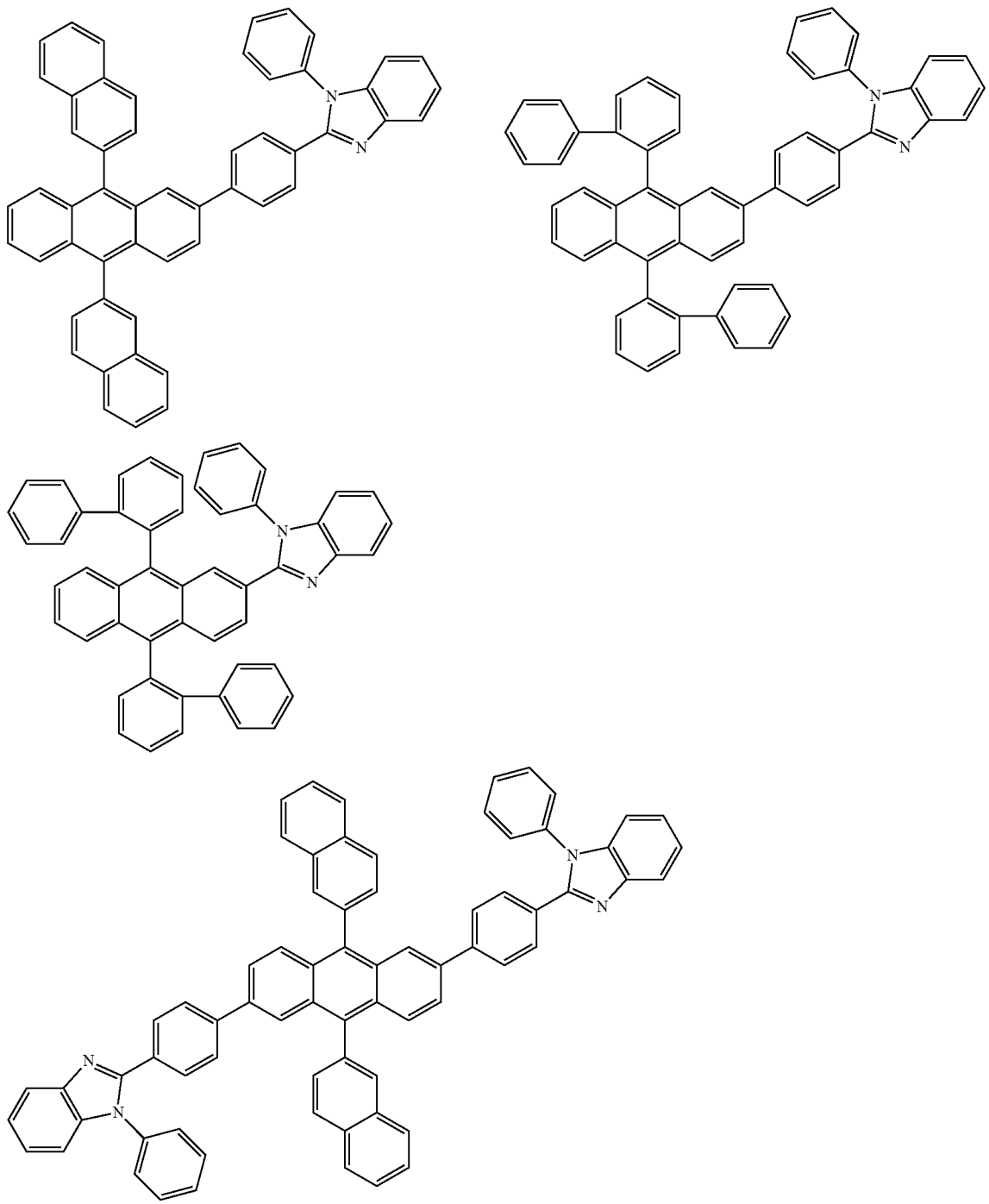

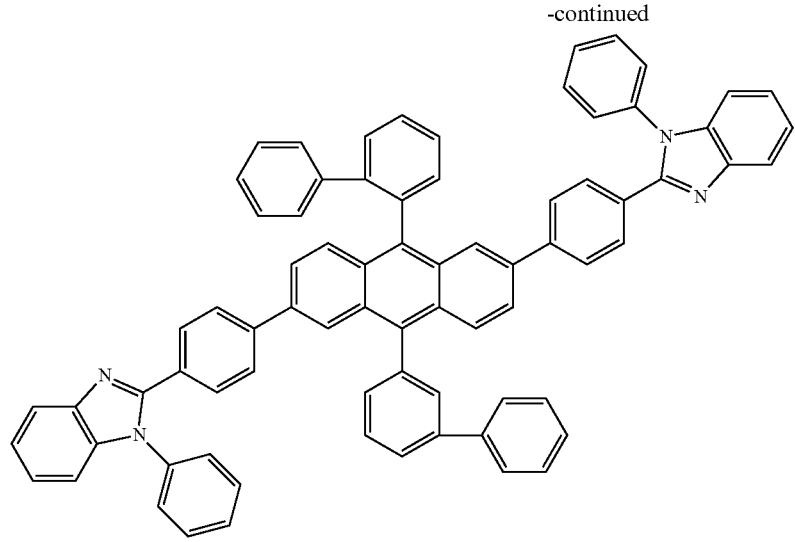
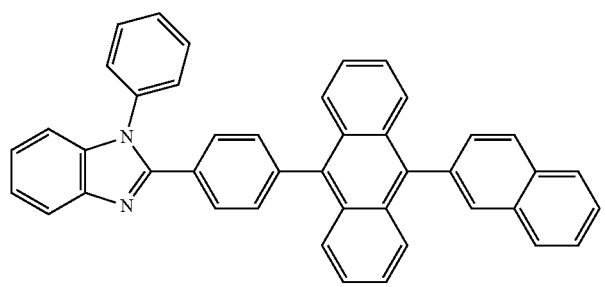
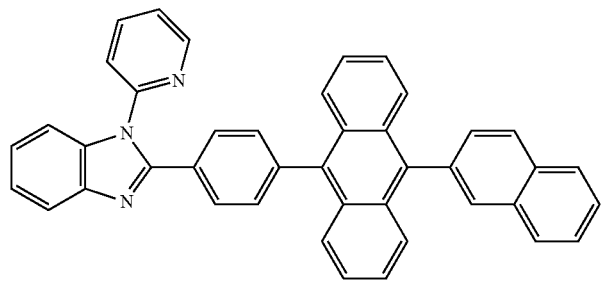
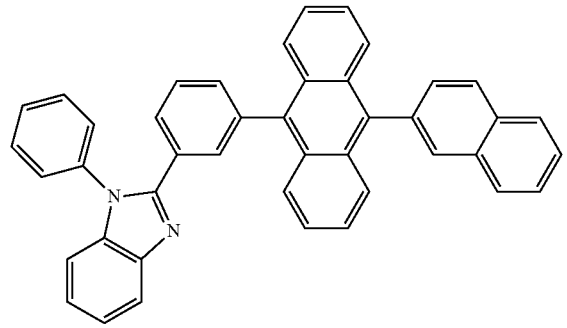
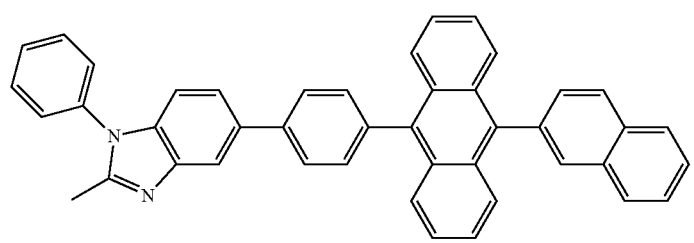

[Chem. 54]

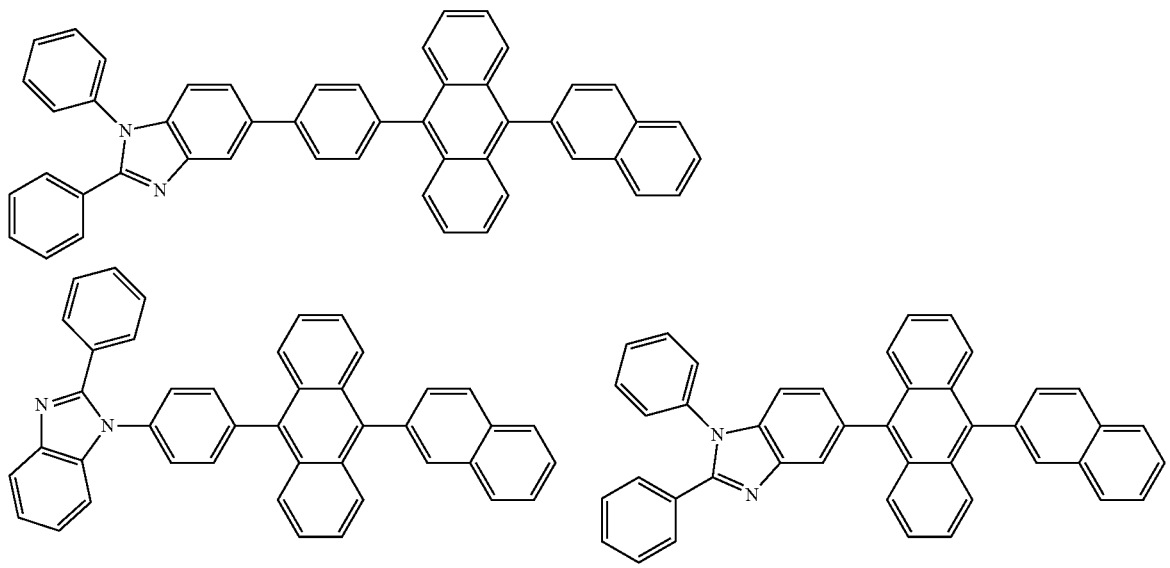

The compound represented by the general formula (P) can be synthesized by the method described in WO2003/060956, WO2004/080975, or the like. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (P) is preferably contained in the organic layer between the light emitting layer and the cathode, and more preferably contained in the layer adjacent to the cathode.

The compound represented by the general formula (P) is contained in the amount of preferably from 70% by mass to 100% by mass, and more preferably from 85% by mass to 100% by mass, with respect to the total mass of the organic layer added.

Preferred examples of the material other than the material used in the electron injecting layer or the electron transporting layer in the organic electroluminescent element of the present invention include silole compounds described in JP-A-9-194487 or the like, phosphineoxide compounds described in JP-A-2006-73581 or the like, nitrogen-containing aromatic 6-membered ring hetero compounds described in JP-A-2005-276801, JP-A-2006-225320, WO2005/085387, or the like, compounds having nitrogen-containing aromatic 6-membered hetero structures and carbazole structures, described in WO2003/080760, WO2005/085387, or the like, and aromatic hydrocarbon compounds described in US2009/0009065, WO2010/134350, JP-T-2010-535806, or the like (naphthalene compounds, anthracene compounds, triphenylene compounds, phenanthrene compounds, pyrene compounds, fluoranthene compounds, and the like).

<Protective Layer>

In the present invention, the entirety of the organic electroluminescent element may be protected by a protective layer.

For the protective layer, the detailed descriptions in paragraph Nos. [0169] to [0170] of JP-A-2008-270736 can also be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure.

For the sealing enclosure, the detailed description in paragraph No. [0171] of JP-A-2008-270736 can be applied to the present invention.

<Driving Method>

The organic electroluminescent element of the present invention can emit light by applying a direct current (it may contain an alternate current component, if necessary) voltage (typically from 2 volts to 15 volts) or a direct current between the anode and the cathode.

As a driving method of the organic electroluminescent element of the present invention, driving methods described in each of the publications of JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element of the present invention is preferably 7% or more, more preferably 10% or more, and still more preferably 12% or more.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by a light extraction efficiency. The light extraction efficiency in usual organic EL elements is about 20%, but by adjusting the shape of a substrate, the shape of an electrode, the thickness of an organic layer, the thickness of an inorganic layer, the refractive index of an organic layer, the refractive index of an inorganic layer, or the like, it is possible to increase the light extraction efficiency to 20% or more.

<Light Emitting Wavelength>

In the organic electroluminescent element of the present invention, the light emitting wavelength is not limited. For example, the organic electroluminescent element may be used in any one of red light emission, green light emission, and blue light emission among the three primary colors. Above all, for the organic electroluminescent element of the present invention, the light emitting wavelength is preferably from 400 nm to 700 nm from the viewpoint of the triplet lowest excited energy ($T_1$ energy) of the compound represented by the general formula (1).

<Use of Organic Electroluminescent Element of the Present Invention>

The organic electroluminescent element of the present invention can be suitably used for display elements, displays, backlights, electrophotography, illumination light sources, recording light sources, exposure light sources, readout light sources, signs, billboards, interior decorations, optical communications, and the like, and particularly preferably for devices driven in a region of high-intensity luminescence, such as a light emitting device, an illumination device, and a display device.

[Light Emitting Device]

The light emitting device of the present invention may include the organic electroluminescent element of the present invention.

Next, the light emitting device of the present invention will be described with reference to FIG. 2.

The light emitting device of the present invention is formed by using the organic electroluminescent element.

Figure 2:
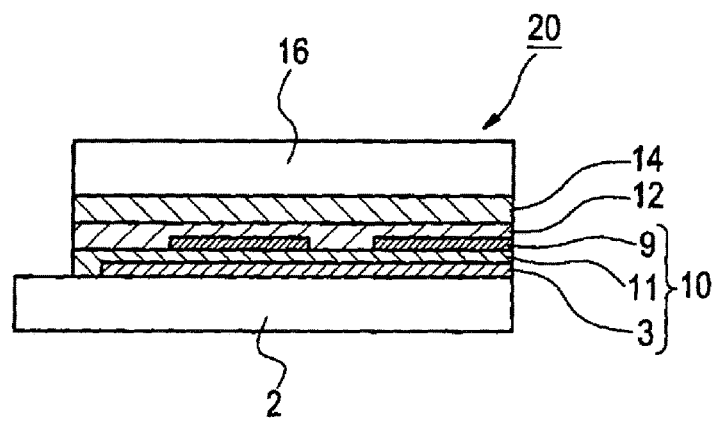
FIG. 2 is a schematic view showing one example of a light emitting device according to the present invention.

FIG. 2 is a cross-sectional view schematically showing one example of the light emitting device of the present invention. The light emitting device 20 in FIG. 2 includes a transparent substrate 2 (supporting substrate), an organic electroluminescent element 10, a sealing enclosure 16, and the like.

The organic electroluminescent element 10 is formed by laminating on the substrate 2 an anode 3 (first electrode), an organic layer 11, and a cathode 9 (second electrode) in this order. In addition, a protective layer 12 is laminated on the cathode 9, and the sealing enclosure 16 is further provided via an adhesive layer 14 on the protective layer 12. Incidentally, a part of each of the electrodes 3 and 9, a diaphragm, an insulating layer, and the like are omitted.

Here, a photocurable adhesive such as an epoxy resin, or a thermosetting adhesive can be used for the adhesive layer 14, and for example, a thermosetting adhesive sheet may also be used.

The light emitting device of the present invention is not particularly limited in its use, and it can be used as not only an illumination device but also a display device of a television set, a personal computer, a mobile phone, electronic paper, or the like.

[Illumination Device]

The illumination device of the present invention includes the organic electroluminescent element of the present invention.

Next, the illumination device of the present invention will be described with reference to FIG. 3.

Figure 3:
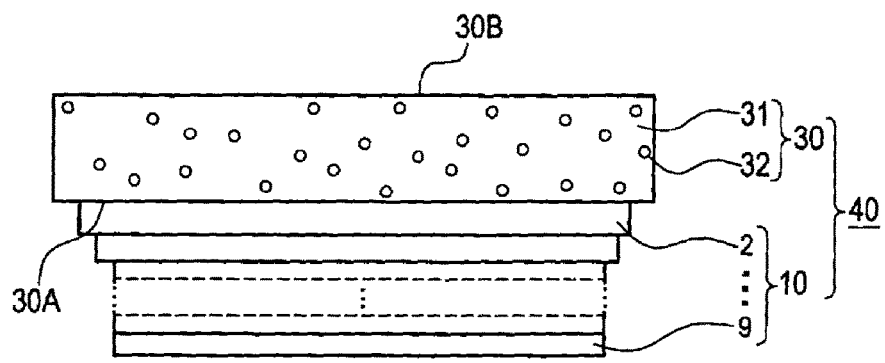
FIG. 3 is a schematic view showing one example of an illumination device according to the present invention.

FIG. 3 is a cross-sectional view schematically showing one example of the illumination device of the present invention. An illumination device 40 of the present invention includes, as shown in FIG. 3, the above-described organic EL element 10 and a light scattering member 30. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is incident on a light incident surface 30A of the scattering member 30, the incident light is scattered by the light scattering member 30 and the scattered light is output as illuminating light from a light output surface 30B.

[Display Device]

The display device of the present invention may include the organic electroluminescent element of the present invention.

The display device of the present invention may be used for, for example, a display device of a television set, a personal computer, a mobile phone, electronic paper, or the like.

EXAMPLES

Hereinafter, the present invention will be described in more detail with reference to Examples. The materials, use amounts, ratios, treatment details, treatment procedures, and the like shown in the following Examples can be appropriately modified in so far as the gist of the present invention is not deviated. Accordingly, the scope of the present invention is not limited to the specific examples shown below.

Example 1

<Synthesis of Material for Organic Electroluminescent Element Represented by General Formula (1)>

The compound represented by the general formula (1) can be synthesized by the method described in WO2009/073245, or a combination of other known reactions. Representative examples of the specific synthesis procedure of the compound represented by the general formula (1) will be described below.

(Synthesis Example 1) Synthesis of Compound 1

[Chem. 55]

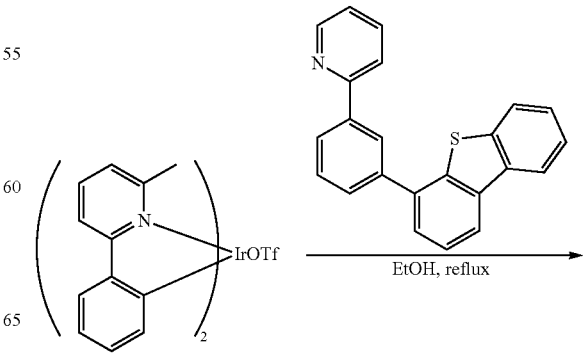

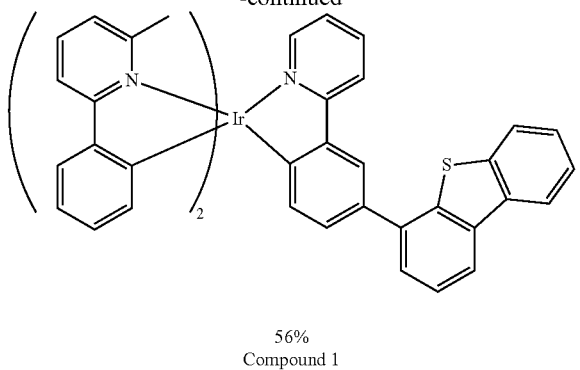

56%
Compound 1

According to the scheme, a compound 1 was synthesized. The starting raw material was synthesized with reference to WO2009/073245. Further, Tf represents a trifluoromethane-sulfonyl group (trifuryl group).

Figure 4:
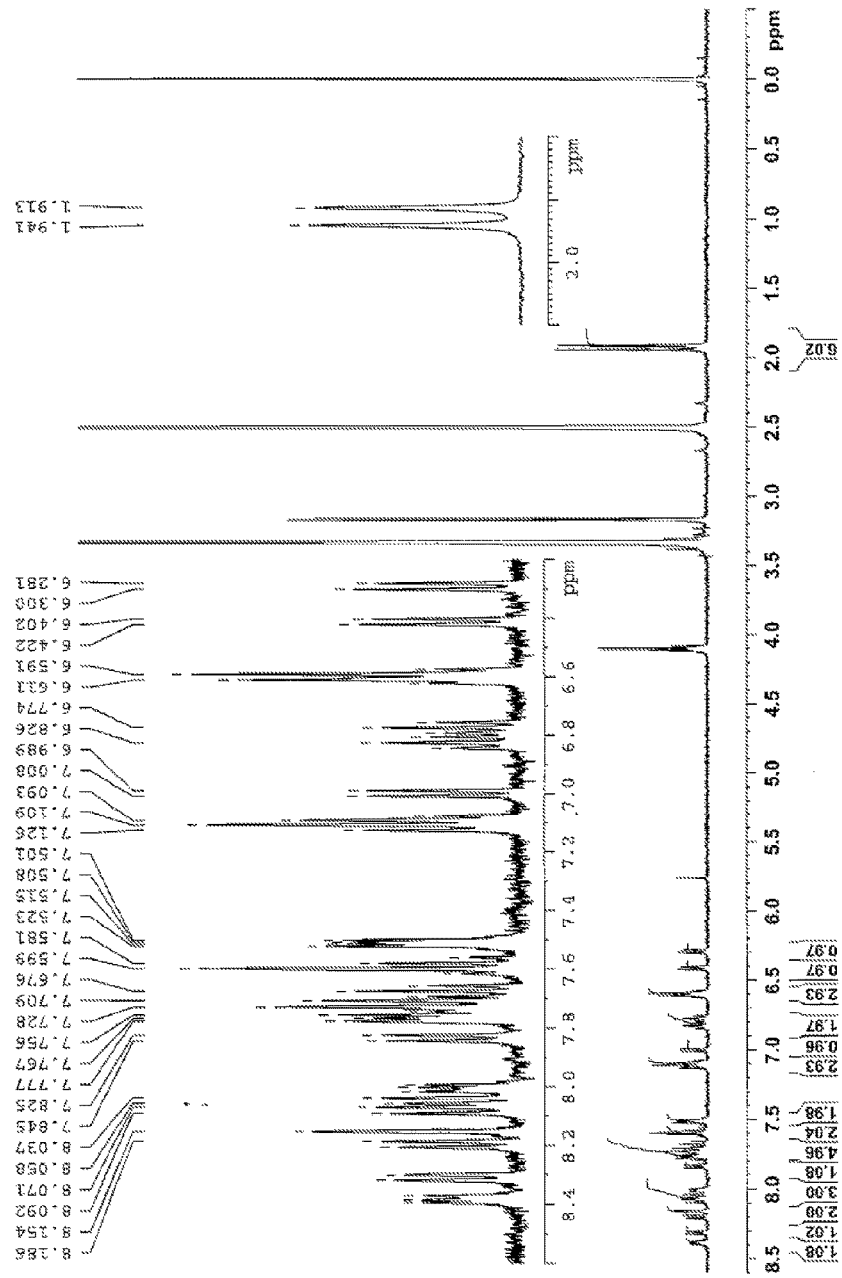
FIG. 4 is an NMR chart of one example of the material for an organic electroluminescent element of the present invention.

The ¹H-NMR data of the synthesized compound 1 are shown in FIG. 4.

NMR data of Compound 1

¹H NMR (400 MHz, in DMSO-$d_6$); δ (ppm)=8.39-8.37 (m, 1H), 8.31 (d, 1H), 8.20 (d, 1H), 8.15 (s, 1H), 8.09-7.99 (m, 3H), 7.83 (d, 1H), 7.78-7.66 (m, 5H), 7.62-7.56 (m, 2H), 7.52-7.50 (m, 2H), 7.13-7.7.08 (m, 3H), 6.99 (d, 1H), 6.85-6.76 (m, 2H), 6.62-6.57 (m, 3H), 6.41 (d, 1H), 6.29 (d, 1H), 1.94 (s, 3H), 1.91 (s, 3H) ppm.

The structures of the materials used for the fabrication of an organic electroluminescent element in each of Examples and Comparative Examples are shown below. Further, the comparative compound 1 is Ir(ppy)₃, the comparative compounds 2 and 3 are Compounds 5 and 6 described in WO2010/028151, respectively, the comparative compound 4 is Compound 7 described in WO2010/111175, and the comparative compound 5 is the compound described in JP-A-2010-229121.

[Chem. 56]

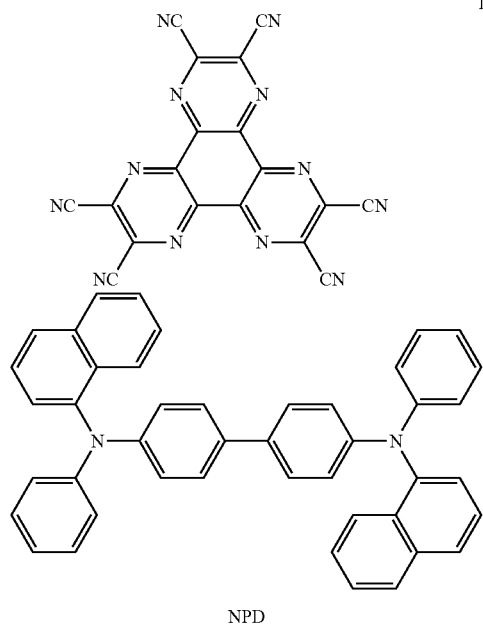

NPD

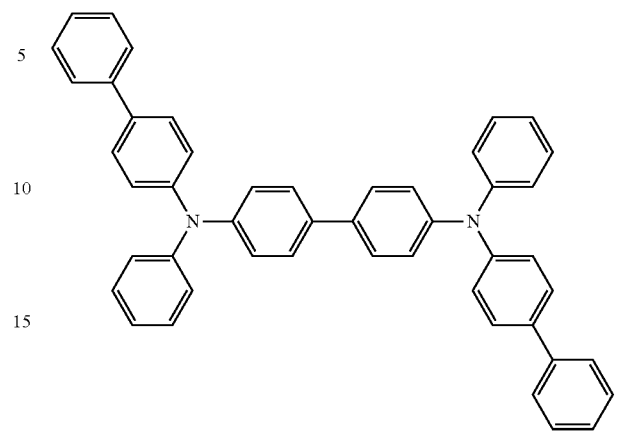

HTL-1

CBP

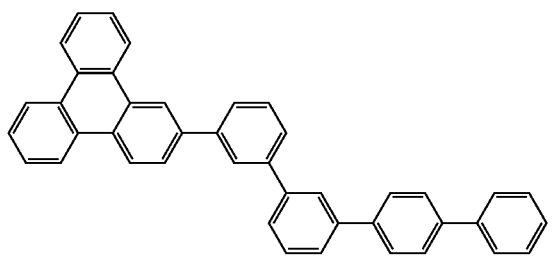

TpH-18

LG 101

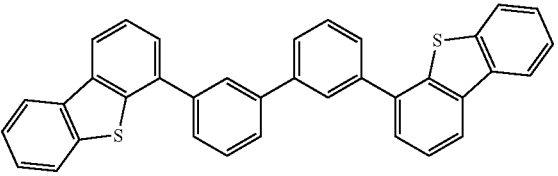

H-1

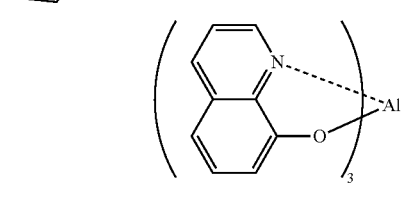

Alq

OM-8
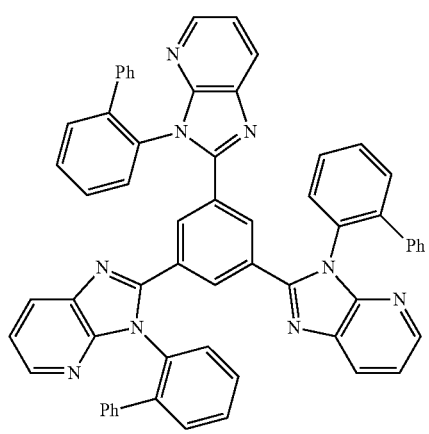
Comparative compound 4
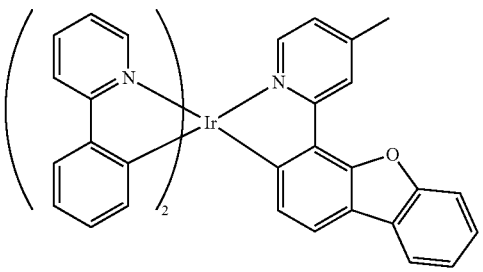
Comparative compound 1
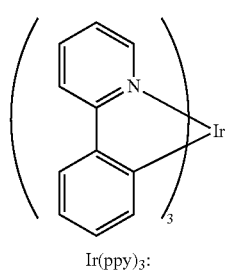
Ir(ppy)₃:
Comparative compound 5
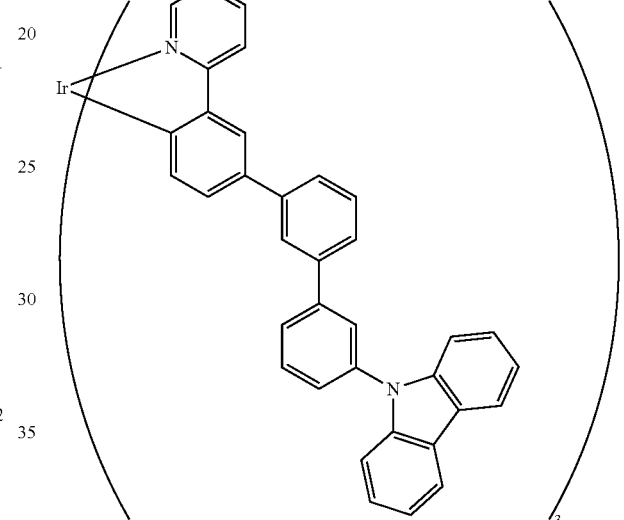
Comparative compound 2
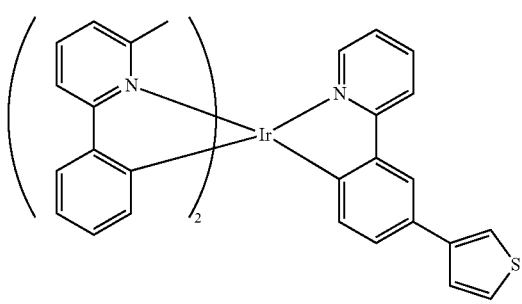
Comparative compound 6
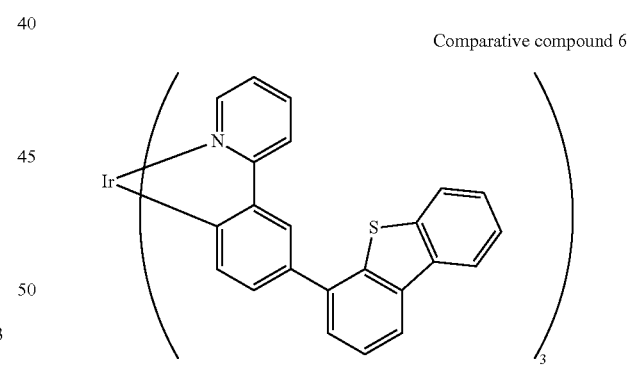
Comparative compound 3
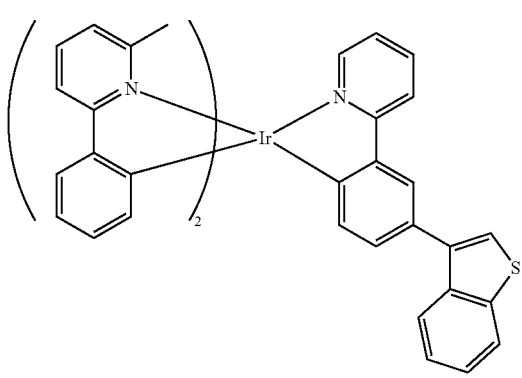
Compound 1
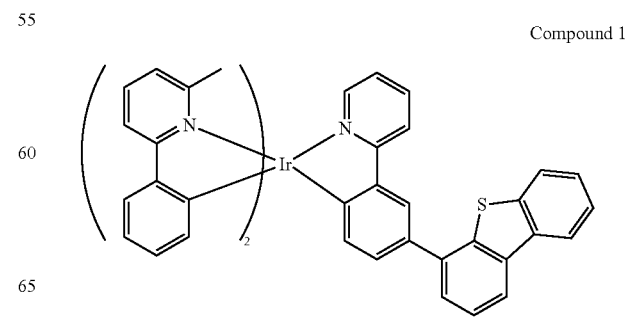

Compound 2

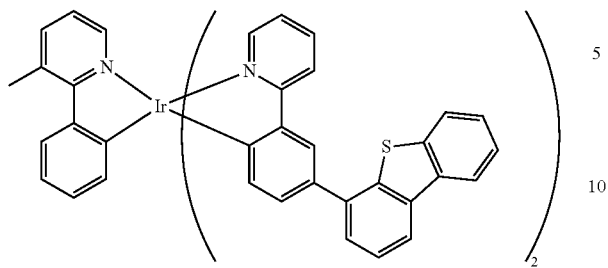

Compound 3

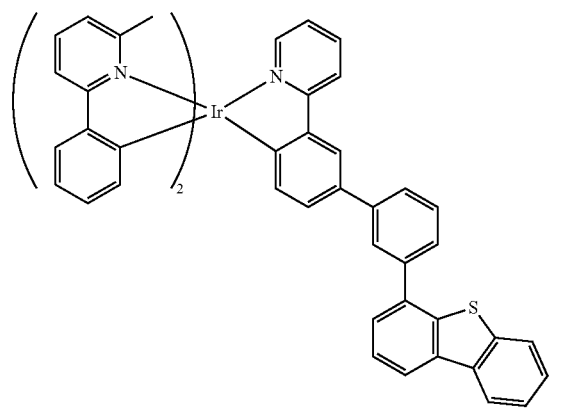

Compound 4

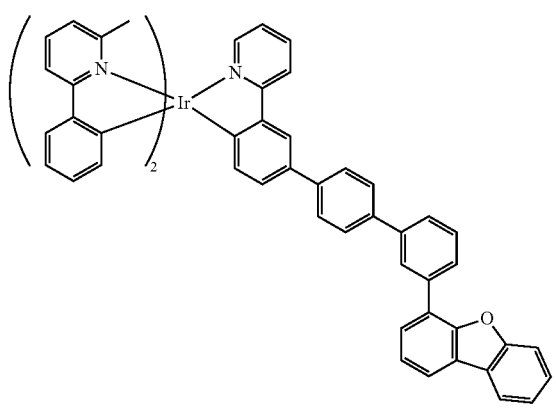

Compound 5

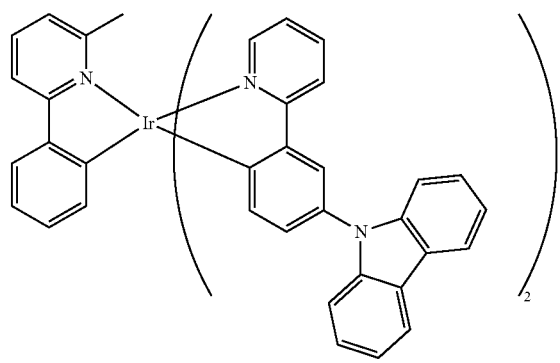

Compound 6

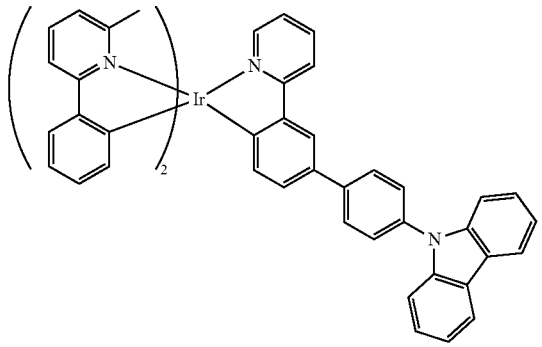

<Fabrication and Evaluation of Elements>

The materials used for the fabrication of elements were subjected to sublimation purification and it was found that the comparative compounds 5 and 6 could not be sublimed. The reason therefor is presumed to be that since the comparative compounds 5 and 6 have high molecular weights, the sublimation points become higher than the decomposition points of the compounds.

Comparative Example 1

(Fabrication of Anode)

A 0.5 mm-thick and 2.5 cm square glass substrate (manufactured by Geomatec Co., Ltd., surface resistance: 10Ω/□) having an ITO film thereon was put in a cleaning container. After ultrasonic cleaning in 2-propanol, the glass substrate was subjected to a UV-ozone treatment for 30 minutes. This was used as an anode (ITO film, transparent anode).

(Lamination of Organic Layers)

On the transparent anode (ITO film), the following organic compound layers were sequentially deposited by a vacuum deposition method. The structures of the compounds used in respective layers are also shown below.

On the anode, first to fifth organic layers were sequentially deposited using the following compounds by a vacuum deposition method. The structures of the compounds used in respective layers are shown below together.

First layer: LG101: film thickness of 10 nm
Second layer: NPD: film thickness of 30 nm
Third layer: CBP (host material) and comparative compound 1 (guest material) (mass ratio 85:15): film thickness of 30 nm
Fourth layer: TpH-18: film thickness of 10 nm
Fifth layer: Alq: film thickness of 40 nm

[Chem. 57]

First Layer

LG 101

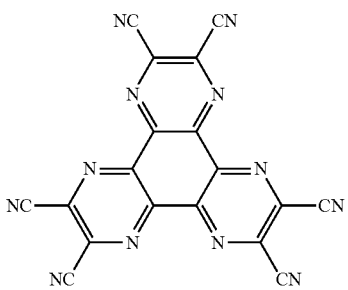

-continued

Second Layer

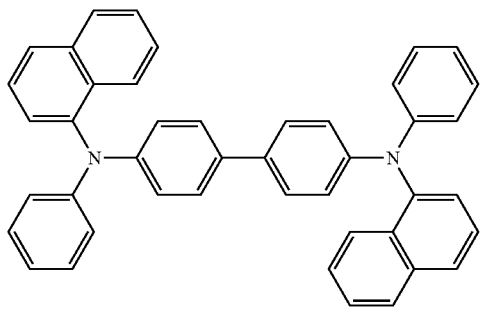

NPD

Third Layer

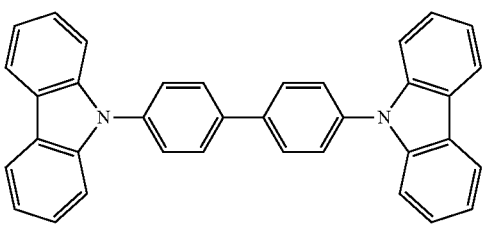

CBP

Comparative compound 1

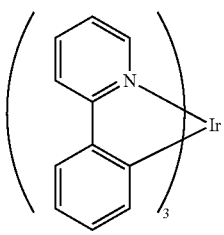

Fourth Layer

TpH-18

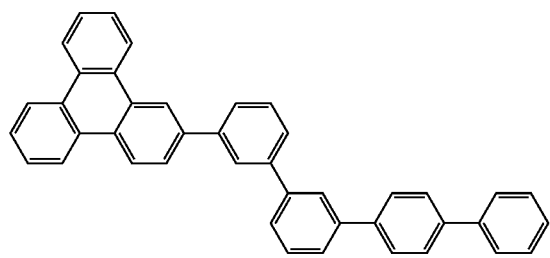

Fifth Layer

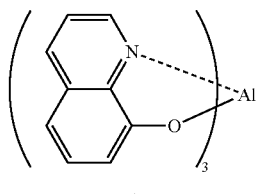

Alq (Fabrication of Cathode)

On the above lamination, 0.1 nm of lithium fluoride and 100 nm of metal aluminum were deposited in this order to form a cathode.

(Fabrication of Organic Electroluminescent Element)

A lamination which includes the five organic layers between the cathode and the anode was placed in a glove box purged with nitrogen gas without contact with atmospheric air, and sealed in a glass sealing can using an ultraviolet curable adhesive (XNR5516HV, manufactured by Nagase-Chiba, Ltd.) to obtain an organic electroluminescent element of Comparative Example 1.

(Evaluation of Organic Electroluminescent Element)

(a) Durability

A direct current voltage was applied to the organic electroluminescent element of Comparative Example 1 to allow the element to emit light continuously to give a luminance of 5000 cd/m$^2$ at room temperature, and the time period required for the luminance to go down to 4500 cd/m$^2$ was measured. This time period was used as an index of the durability of the organic electroluminescent element. For the organic electroluminescent element of Comparative Example 1, the durability and the driving voltage were evaluated by the following method, and the results are shown in Table 1.

Furthermore, in Table 1 shown below in the respective Examples and Comparative Examples as described later, the durability at a time of using the organic electroluminescent element of Comparative Example 1 was taken as 100, and the element having a relative value of the durability of less than 130 was rated as "D", the element having that of 130 or more and less than 145 was rated as "C", the element having that of 145 or more and less than 160 was rated as "B", and the element having that of 160 or more was rated as "A".

Here, the larger the number of durability is, is more preferred.

(b) Driving Voltage

A direct current voltage was applied to allow the element to emit light to give a luminance of 1000 cd/m$^2$. The voltage applied at this time was used as an index of the evaluation of the driving voltage. Further, for the organic electroluminescent element of Comparative Example 1, the driving voltage was evaluated by the following method and the results are shown Table 1. Furthermore, in respective Examples and Comparative Examples as described later, by taking the voltage of the organic electroluminescent element of Comparative Example 1 was taken as 100, the element having a relative value of the voltage of 100 or more was rated as "D", the element having that of 95 or more and less than 100 was rated as "C", the element having that of 90 or more and less than 95 was rated as "B", and the element having that of less than 90 was rated as "A" in Table 1 as described below.

Here, A smaller number of driving voltage is more preferred.

Example A1 and Comparative Examples 2 to 4

Organic electroluminescent elements in Examples A1 to A3 and Comparative Examples 2 to 4 were obtained in the same manner as in Comparative Example 1, except that the compounds 1, 4, and 6 of the present invention synthesized above or the comparative compounds 2 to 4 were used instead of the comparative compound 1 as a material for the third layer in the organic layers in Comparative Example 1.

The durability and the driving voltage of these organic electroluminescent elements were evaluated in the same manner as in Comparative Example 1, and the results are shown in Table 1 below.

TABLE 1

|  | Guest material | Durability | Driving voltage |
|---|---|---|---|
| Comparative Example 1 | Comparative compound 1 | — | — |
| Comparative Example 2 | Comparative compound 2 | D | B |
| Comparative Example 3 | Comparative compound 3 | D | D |
| Comparative Example 4 | Comparative compound 4 | D | C |
| Example A1 | Compound 1 | A | B |
| Example A2 | Compound 4 | B | B |
| Example A3 | Compound 6 | B | A |

Comparative Example 5

An organic electroluminescent element of Comparative Example was fabricated in the same manner as in Comparative Example 1, except that CBP used in the third layer was changed to TpH-18 in the organic layer of the organic electroluminescent element of Comparative Example 1. The configuration of the organic layers in Comparative Example 5 is shown below.

First layer: LG101: film thickness of 10 nm
Second layer: NPD: film thickness of 30 nm
Third layer: TpH-18 (host material) and comparative compound 1 (guest material) (mass ratio 85:15): film thickness of 30 nm
Fourth layer: TpH-18: film thickness of 10 nm
Fifth layer: Alq: film thickness of 40 nm The durability and the driving voltage of the organic electroluminescent element of Comparative Example 5 were evaluated in the same manner as in Comparative Example 1, and the results are shown in Table 2 below.

Example B1 and Comparative Examples 6 to 8

Organic electroluminescent elements of Examples B1 to B4 and Comparative Examples 6 to 8 were obtained in the same manner as in Comparative Example 5, except that the compounds 1, 2, 4, and 5 of the present invention synthesized above or the comparative compounds 2 to 4 were used instead of the comparative compound 1 as the material for the third layer in the organic layers in Comparative Example 5.

The durability and the driving voltage of these organic electroluminescent elements were evaluated in the same manner as in Comparative Example 1, and the results are shown in Table 2 below.

TABLE 2

|  | Guest material | Durability | Driving voltage |
|---|---|---|---|
| Comparative Example 5 | Comparative compound 1 | — | — |
| Comparative Example 6 | Comparative compound 2 | D | B |
| Comparative Example 7 | Comparative compound 3 | D | C |
| Comparative Example 8 | Comparative compound 4 | D | C |
| Example B1 | Compound 1 | A | B |
| Example B2 | Compound 2 | B | A |
| Example B3 | Compound 4 | A | B |
| Example B4 | Compound 5 | B | B |

Comparative Example 9

An element of Comparative Example 9 was fabricated in the same manner as in Comparative Example 5, except that NPD used in the second layer was changed to HTL-1, TpH-18 used in the fourth layer was changed to OM-8, and Alq used in the fifth layer was changed to OM-8 in the organic layer of the organic electroluminescent element of Comparative Example 5. The configuration of the organic layers in Comparative Example 9 is shown below.

First layer: LG101: film thickness of 10 nm
Second layer: HTL-1: film thickness of 30 nm
Third layer: TpH-18 (host material) and comparative compound 1 (guest material) (mass ratio 85:15): film thickness of 30 nm
Fourth layer: OM-8: film thickness of 10 nm
Fifth layer: OM-8: film thickness of 40 nm The durability and the driving voltage of the organic electroluminescent element of Comparative Example 9 were evaluated in the same manner as in Comparative Example 1, and the results are shown in Table 3 below.

Example C1 and Comparative Examples 10 to 12

Organic electroluminescent elements of Examples C1 to C3 and Comparative Examples 10 to 12 were each obtained in the same manner as in Comparative Example 9, except that the compounds 1, 3, and 6 of the present invention synthesized above or the comparative compounds 2 to 4 were used instead of the comparative compound 1 as the material for the third layer in the organic layers in Comparative Example 9.

The durability and the driving voltage of these organic electroluminescent elements were evaluated in the same manner as in Comparative Example 1, and the results are shown in Table 3 below.

TABLE 3

|  | Guest material | Durability | Driving voltage |
|---|---|---|---|
| Comparative Example 9 | Comparative compound 1 | — | — |
| Comparative Example 10 | Comparative compound 2 | D | B |
| Comparative Example 11 | Comparative compound 3 | D | D |
| Comparative Example 12 | Comparative compound 4 | D | C |
| Example C1 | Compound 1 | A | B |
| Example C2 | Compound 3 | B | B |
| Example C3 | Compound 6 | B | A |

Comparative Example 13

An element of Comparative Example 13 was fabricated in the same manner as in Comparative Example 9, except that TpH-17 used in the third layer was changed to H-1 in the organic layer of the organic electroluminescent element of Comparative Example 9. The configuration of the organic layers in Comparative Example 13 is shown below.

First layer: LG101: film thickness of 10 nm
Second layer: HTL-1: film thickness of 30 nm
Third layer: H-1 (host material) and comparative compound 1 (guest material) (mass ratio 85:15): film thickness of 30 nm
Fourth layer: OM-8: film thickness of 10 nm
Fifth layer: OM-8: film thickness of 40 nm The durability and the driving voltage of the organic electroluminescent element of Comparative Example 13 were evaluated in the same manner as in Comparative Example 1, and the results are shown in Table 4 below.

Example D1 and Comparative Examples 14 to 16

Organic electroluminescent elements of Examples D1 to D3 and Comparative Examples 14 to 16 were each obtained in the same manner as in Comparative Example 13, except that the compounds 1, 2, and 4 of the present invention synthesized above or the comparative compounds 2 to 4 were used instead of the comparative compound 1 as the material for the third layer in the organic layers in Comparative Example 13.

The durability and the driving voltage of these organic electroluminescent elements were evaluated in the same manner as in Comparative Example 1, and the results are shown in Table 4 below.

TABLE 4

|  | Guest material | Durability | Driving voltage |
|---|---|---|---|
| Comparative Example 13 | Comparative compound 1 | — | — |
| Comparative Example 14 | Comparative compound 2 | D | B |
| Comparative Example 15 | Comparative compound 3 | D | D |
| Comparative Example 16 | Comparative compound 4 | D | C |
| Example D1 | Compound 1 | A | A |
| Example D2 | Compound 2 | B | A |
| Example D3 | Compound 4 | A | B |

From the results of Tables 1 to 4, it could be seen that the organic electroluminescent element of the present invention, using the compound of the present invention, has excellent durability and driving voltage.

It could be seen that each of the comparative elements using the comparative compound 1 which is a representative iridium complex, has poor durability and driving voltage.

On the other hand, it could be seen that each of the comparative elements using the comparative compounds 2 and 3 described in WO2010/028151, having structures having no G in the general formula (1), has poor durability.

In addition, it could be seen that the organic electroluminescent element in each of Comparative Examples, using the comparative compound 4 having a structure having a fused ring with 3 or more rings but not satisfying the general formula (1) has poor durability.

On the other hand, the comparative compound 5 described in JP-A-2010-229121 has an increased molecular weight and thus an elevated sublimation temperature, from which it could be seen that there is no deposition titration.

Similarly, the comparative compound 6 having three ligands having dibenzothiophene has an increased molecular weight and thus an elevated sublimation temperature, from which it could be seen that there is no deposition titration.

REFERENCE SIGNS LIST

2: substrate
3: anode
4: hole injecting layer
5: hole transporting layer
6: light emitting layer
7: hole blocking layer
8: electron transporting layer
9: cathode
10: organic electroluminescent element
11: organic layer
12: protective layer
14: adhesive layer
16: sealing enclosure
20: light emitting device
30: light scattering member
31: transparent substrate
30A: light incident surface
30B: light output surface
32: fine particles
40: illumination device

The invention claimed is:
1. A compound represented by the following formula (3):

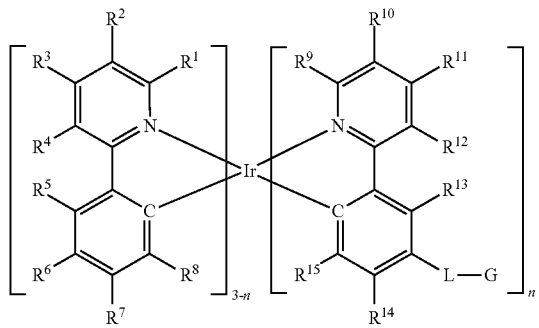

Formula (3)

wherein
n represents 1 or 2;
L represents a single bond or a linking group; and
wherein $R^1$ to $R^{15}$ each independently represent a hydrogen atom, an alkyl group, an aryl group, or a heteroaryl group, and $R^1$ to $R^{15}$ does not include a fused ring with 3 or more rings;
G represents a fused ring with 3 or more rings selected from the group consisting of:

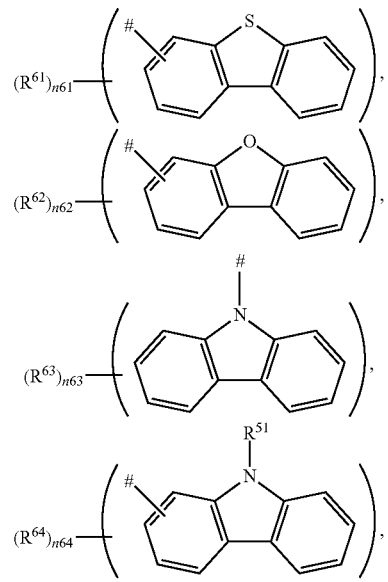

-continued

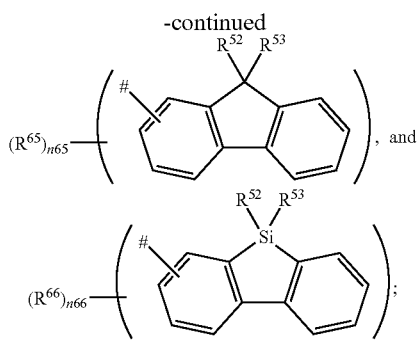
, and wherein $R^{51}$ to $R^{55}$ each independently represent an alkyl group or an aryl group, and #represents a binding position with L; $R^{61}$ to $R^{66}$ each independently represent a hydrogen atom or a substituent, and $n_{61}$ to $n_{66}$ each independently represent an integer of 0 to 8.

2. The compound according to claim 1, wherein L of the compound represented by the formula (3) is a single bond or a group selected from the following group $L^1$ of linking groups:

Group $L^1$ of Linking Groups

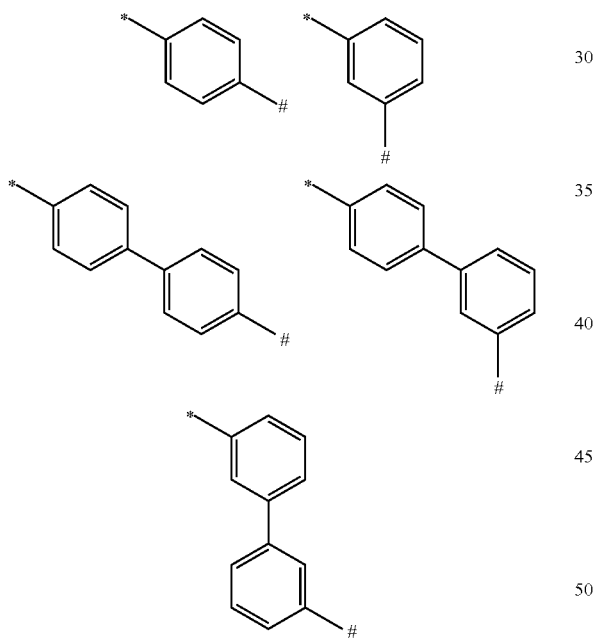

wherein * represents a binding position with a benzene ring of Formula (3) and # represents a binding position with G.

3. An organic electroluminescent element comprising:
a substrate;
a pair of electrodes including an anode and a cathode, disposed on the substrate; and
at least one organic layer including a light emitting layer, disposed between the electrodes,
wherein the at least one organic layer contains a compound represented by the following general formula (3):

General Formula (3)

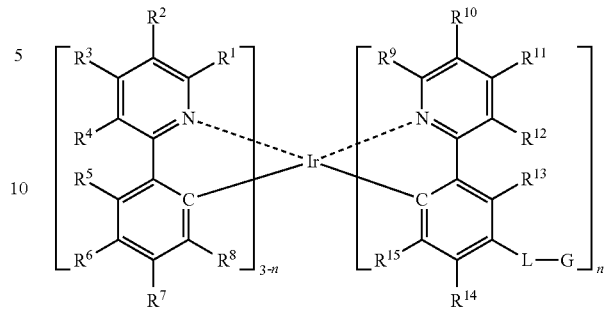

wherein $R^1$ to $R^{15}$ each independently represent a hydrogen atom, an alkyl group, an aryl group, or a heteroaryl group, and $R^1$ to $R^{15}$ does not include a fused ring with 3 or more rings; n represents 1 or 2; L represents a single bond or a linking group;
G represents a fused ring with 3 or more rings selected from the group consisting of:

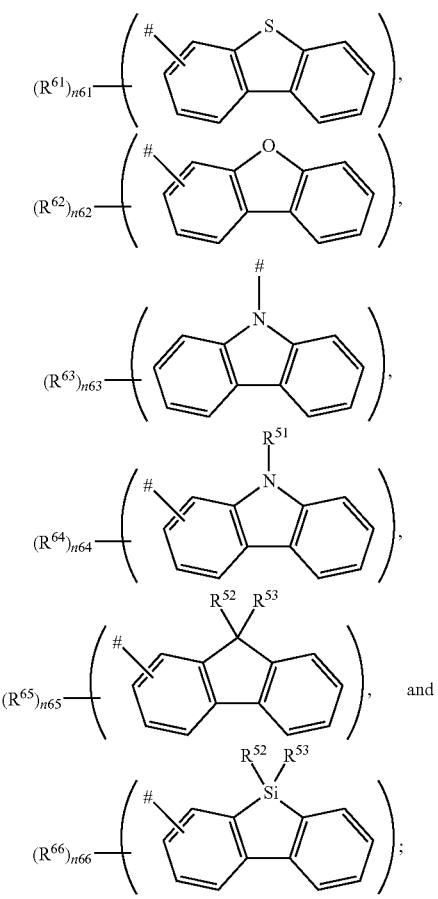

wherein $R^{51}$ to $R^{55}$ each independently represent an alkyl group or an aryl group, and #represents a binding position with L; $R^{61}$ to $R^{66}$ each independently represent a hydrogen atom or a substituent, and $n_{61}$ to $n_{66}$ each independently represent an integer of 0 to 8.

4. The organic electroluminescent element according to claim 3, wherein L of the compound represented by the general formula (3) is a single bond or a group selected from the following group L¹ of linking groups:

Group L¹ of Linking Groups

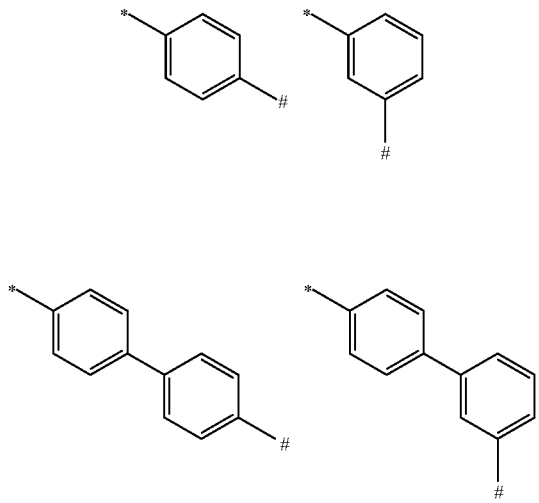

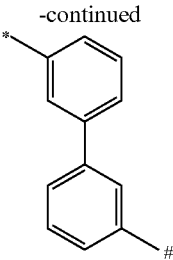

wherein * represents a binding position with a benzene ring of Formula (3) and #represents a binding position with G.

5. The organic electroluminescent element according to claim 3, wherein the compound represented by the general formula (3) is contained in the light emitting layer in the organic layer(s).

6. A light emitting device using the organic electroluminescent element according to claim 3.

7. A display device using the organic electroluminescent element according to claim 3.

8. An illumination device using the organic electroluminescent element according to claim 3.

* * * * *